United States Patent
Oehrlein et al.

(10) Patent No.: US 12,384,785 B2
(45) Date of Patent: Aug. 12, 2025

(54) PROCEDURE FOR THE FORMATION OF 2H-BENZOTRIAZOLE BODIES AND CONGENERS

(71) Applicant: BASF SE, Ludwigshafen am Rhein (DE)

(72) Inventors: Reinhold Oehrlein, Rheinfelden-Herten (DE); Gabriele Baisch, Binzen (DE)

(73) Assignee: BASF SE, Ludwigshafen am Rhein (DE)

( * ) Notice: Subject to any disclaimer, the term of this patent is extended or adjusted under 35 U.S.C. 154(b) by 1086 days.

(21) Appl. No.: 17/311,196

(22) PCT Filed: Dec. 2, 2019

(86) PCT No.: PCT/EP2019/083232
§ 371 (c)(1),
(2) Date: Jun. 4, 2021

(87) PCT Pub. No.: WO2020/114936
PCT Pub. Date: Jun. 11, 2020

(65) Prior Publication Data
US 2022/0017527 A1 Jan. 20, 2022

(30) Foreign Application Priority Data
Dec. 6, 2018 (EP) .................................... 18210785

(51) Int. Cl.
*C07D 487/04* (2006.01)
*C07D 249/20* (2006.01)
*C07D 471/04* (2006.01)

(52) U.S. Cl.
CPC ......... *C07D 487/04* (2013.01); *C07D 249/20* (2013.01); *C07D 471/04* (2013.01)

(58) Field of Classification Search
CPC ... C07D 487/04; C07D 249/20; C07D 471/04
See application file for complete search history.

(56) References Cited

U.S. PATENT DOCUMENTS

| | | | |
|---|---|---|---|
| 3,980,634 A | 9/1976 | Weaver | |
| 4,127,586 A * | 11/1978 | Rody | ...................... C09K 15/30 524/84 |
| 4,230,867 A | 10/1980 | Kintopf et al. | |
| 4,275,004 A | 6/1981 | Martin | |
| 4,347,180 A | 8/1982 | Winter et al. | |
| 5,125,074 A | 6/1992 | Labeaute et al. | |
| 2004/0019220 A1 | 1/2004 | Fischer et al. | |
| 2012/0058974 A1 | 3/2012 | Misske et al. | |
| 2017/0066711 A1 | 3/2017 | Lumb et al. | |

FOREIGN PATENT DOCUMENTS

| | | | |
|---|---|---|---|
| CH | 476744 | * | 8/1969 |
| CN | 102432613 A | * | 5/2012 |
| DE | 10001832 A1 | | 7/2000 |
| WO | 02/12202 A2 | | 2/2002 |
| WO | 2003/105538 A1 | | 12/2003 |
| WO | 2005/093007 A1 | | 10/2005 |
| WO | 2006/082145 A1 | | 8/2006 |
| WO | 2011/161105 A2 | | 12/2011 |

OTHER PUBLICATIONS

Kasumov et al., "Synthesis and ESR studies of redox reactivity of bis (3,5-di-tert-butyl-1,2-benzoquinone-2-monooximato)Cu(II)", Spectrochimica Acta Part A: Molecular and Biomolecular Spectroscopy, vol. 56, Issue 5, Apr. 2000, pp. 841-850.

Katritzky et al., "Syntheses of triazolo[6,7-d]phthalide and triazolo[6,7-d]dihydrocoumarin", Journal of Heterocyclic Chemistry, vol. 29, Issue 6, Oct./Nov. 1992, pp. 1519-1523.

Kržan et al., "Novel associations of ortho quinone monooximes: hydrogen bonded dimers of 4,6-di-tert-butyl-1,2-benzoquinone-2-monooxime", Acta Chimica Slovenica, vol. 48, Issue 2, 2001, pp. 229-239.

Liu et al., "A Practical and Scalable Synthesis of GTx-134, an IGF-1R Inhibitor", Journal of Heterocyclic Chemistry, vol. 53, Issue 5, Jun. 4, 2015, pp. 1430-1438.

Maruyama et al., "Studies on the Baudisch reaction. I. The synthesis of o-nitrosophenols", The Journal of Organic Chemistry, vol. 32, Issue 2, Aug. 1, 1967, pp. 2516-2520.

Shishkina et al., "Halonitrophthalimides and Phthalodinitriles Derived from Them", Russian Journal of General Chemistry, vol. 67, Issue 5, 1997, pp. 789-792.

Uyanik et al., "IBS-Catalyzed Regioselective Oxidation of Phenols to 1,2-Quinones with Oxone®", Molecules, vol. 17, Issue 7, Jul. 18, 2012, pp. 8604-8616.

Zincke et al., "Ueber Orthoamidoazoverbindungen des Xylols und Pseudocumols", Berichte der deutschen chemischen Gesellschaft, vol. 21, Issue 1, Jan.-Jun. 1888, pp. 540-548.

Bellotto et al., "Synthesis and Photochemical Properties of Oligo-ortho azobenzenes", Journal of Organic Chemistry, vol. 76, No. 23, Dec. 2, 2011, pp. 9826-9834.

Gou et al., "Synthesis and properties of multifunctional hindered amine light stabilizers", Heterocyclic Communications, vol. 20, No. 1, Jan. 1, 2014, pp. 15-20.

International Preliminary Report on Patentability received for PCT Patent Application No. PCT/EP2019/083232, mailed on Jun. 17, 2021, 9 pages.

International Search Report and Written Opinion received for PCT Patent Application No. PCT/EP2019/083232, mailed on Jan. 28, 2020, 11 pages.

* cited by examiner

*Primary Examiner* — Daniel R Carcanague
(74) *Attorney, Agent, or Firm* — Faegre Drinker Biddle & Reath LLP

(57) ABSTRACT

The present invention relates to a process for the preparation of 2H-benzotriazole compounds and congeners, novel 2H-benzotriazole compounds and congeners and their use as UV absorbers in coatings and bulk plastics.

18 Claims, 1 Drawing Sheet

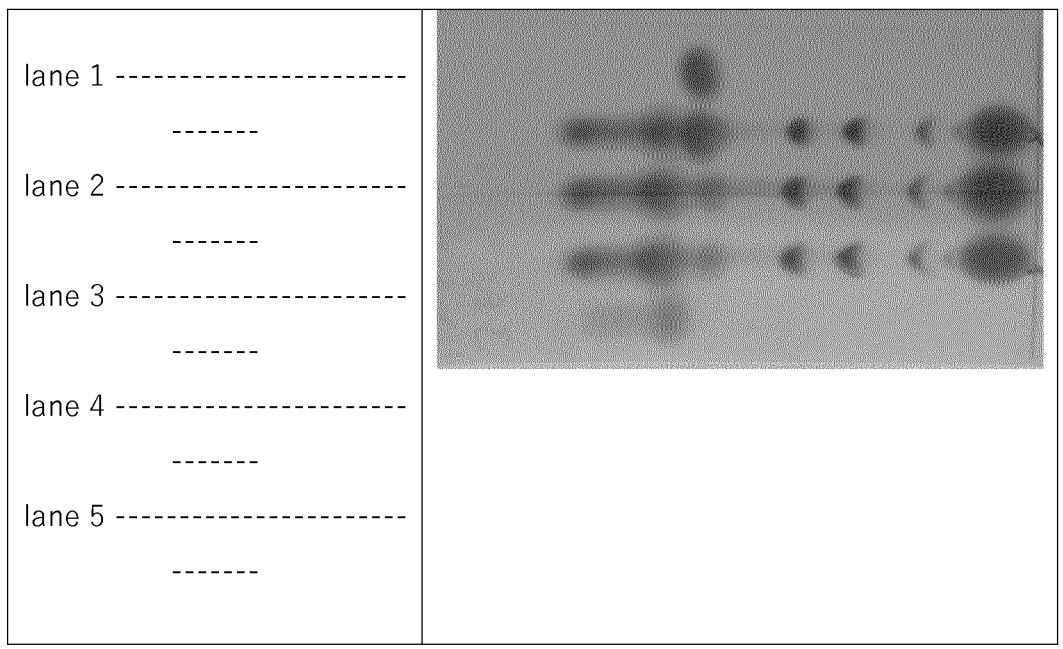

PROCEDURE FOR THE FORMATION OF 2H-BENZOTRIAZOLE BODIES AND CONGENERS

CROSS-REFERENCE TO RELATED APPLICATIONS

This application is a national stage application (under 35 U.S.C. § 371) of PCT/EP2019/083232, filed Dec. 2, 2019, which claims benefit of European Application No. 18210785.4, filed Dec. 6, 2018, both of which are incorporated herein by reference in their entirety.

The present invention relates to a process for the preparation of 2H-benzotriazole compounds and congeners, novel 2H-benzotriazole compounds and congeners, and their use as UV absorbers in coatings and bulk plastics. More specifically, the preparation process is highly efficient and broadly applicable. The novel process is also more sustainable compared to conventional procedures with respect to the formation of unwanted chemical waste and necessary energy input. The process also avoids current hazardous production conditions.

2H-Benzotriazoles are a well-known class of chemicals used to protect various organic coatings and varnishes from UV-degradation. Further, as described in WO 2005/093007 A1, benzotriazole compounds have been used as additives in light emitting layers as OLEDs.

According to WO 2006/082145 A1, a number of structurally different benzotriazole compounds have been applied in the automotive coatings industry. With respect to customer needs, the photochemical stability of such benzotriazole compounds is of great technical importance. Moreover, by varying the chemical structure of the benzotriazole body, the wavelength of their UV-absorbance can be fine-tuned which makes possible a highly customer specific application. As described in DE 100 01 832 A1, additional chemical groups linked to the benzotriazole body allow to design tailored compatibility to advanced coatings and varnish blends.

Conventionally, benzotriazole compounds are assembled by forming either a 1,2-halo- or 1,2-nitro-substituted diarylazo intermediate compound. The 1,2-halo-diarylazo intermediate compound is subsequently treated with an excess of azide at elevated temperature to replace the halogen and introduce the third nitrogen thereby ending up with the benzotriazole product (see for instance T. Zincke et al. Chem. Ber. 1887, 21, 540 and WO 2006/082145 A1).

Alternatively, the 1,2-nitro-diarylazo intermediate compound is cyclized to the desired benzotriazole product by reduction of the nitro group (see for instance U.S. Pat. Nos. 4,347,180 and 4,275,004). However, both approaches are hampered by the severe and corrosive conditions including concentrated sulfuric acid and nitric acid required to produce the hazardous diazonium salt precursor of the diarylazo intermediates. In addition, the route based on the reductive cyclization of the 1,2-nitro-diarylazo intermediate results in side products of the reduction of the nitro group which requires tedious and costly purification procedures. Furthermore, chemically sensitive functional groups do not survive these harsh reaction conditions.

Accordingly, there is a need for an improved, broadly applicable preparation process for 2H-benzotriazole compounds and congeners. This process should be suitable for industrial scale affording the desired compounds in high yields and high purity.

This present invention solves this objective by providing a novel, straight-forward synthetic route to 2H-benzotriazole compounds.

In a first aspect, the present invention is directed to a process for the preparation of a benzotriazole compound according to the general formula (I):

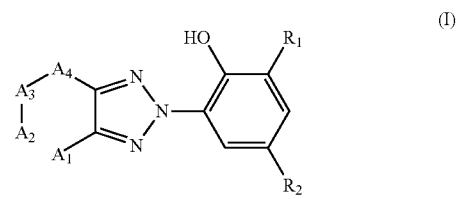

wherein $R_1$ is hydrogen, linear or branched $C_1$-$C_{24}$alkyl, linear or branched $C_2$-$C_{18}$alkenyl, $C_5$-$C_{12}$cycloalkyl, unsubstituted $C_7$-$C_{15}$phenylalkyl, $C_7$-$C_{15}$phenylalkyl with the phenyl moiety substituted once, twice, three times or four times with $C_1$-$C_4$alkyl, unsubstituted phenyl, phenyl substituted once, twice, three times or four times with $C_1$-$C_4$alkyl;

$R_2$ is, independently from $R_1$, linear or branched $C_1$-$C_{24}$alkyl, linear or branched $C_2$-$C_{18}$alkenyl, $C_5$-$C_{12}$cycloalkyl, unsubstituted $C_7$-$C_{15}$phenylalkyl, $C_7$-$C_{15}$phenylalkyl with the phenyl moiety substituted once, twice, three times or four times with $C_1$-$C_4$alkyl, unsubstituted phenyl, phenyl substituted once, twice, or three times with $C_1$-$C_4$alkyl, wherein alkyl is optionally substituted by one or more —OH, —OCO—$R_3$, —O$R_4$, —NCO, —NH$_2$ or combinations thereof, wherein $R_3$ is hydrogen, linear or branched $C_1$-$C_{16}$alkyl, $C_5$-$C_{12}$cycloalkyl, linear or branched $C_3$-$C_6$alkenyl, phenyl, naphthyl or $C_7$-$C_{15}$phenylalkyl and $R_4$ is hydrogen, linear or branched $C_1$-$C_{24}$ alkyl; —O$R_4$, —C(O)O$R_4$, —C(O)NH$R_4$ or —C(O)N$R_4R_4$; —S$R_5$, —NH$R_5$, or —N($R_5$)$_2$, wherein $R_5$ is $C_1$-$C_{20}$alkyl, $C_2$-$C_{20}$hydroxyalkyl; $C_3$-$C_{18}$alkenyl, $C_5$-$C_{12}$cycloalkyl, $C_7$-$C_{15}$phenylalkyl, unsubstituted phenyl, unsubstituted naphthyl, phenyl substituted once or twice with $C_1$-$C_4$alkyl, or naphthyl substituted once or twice with $C_1$-$C_4$alkyl;

—(CH$_2$)$_m$—CO—$X_1$—(Z)$_p$—Y—$R_6$, wherein $X_1$ is —O— or —N$R_7$—, Y is —O— or N$R_8$— or a direct bond, Z is $C_2$-$C_{12}$alkylene, $C_4$-$C_{12}$alkylene interrupted by one to three nitrogen atoms, oxygen atoms or combinations thereof, $C_3$-$C_{12}$alkylene, butenylene, butynylene, cyclohexylene or phenylene, wherein each of which may be additionally substituted by a hydroxyl group; or a group selected from the following list of structures:

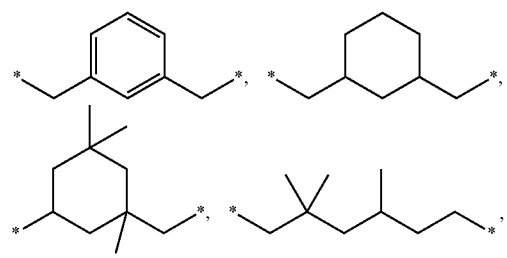

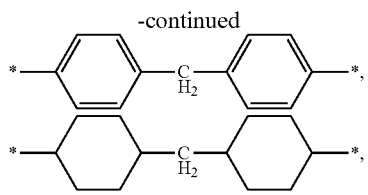

wherein * denotes a bond;
or when Y is a direct bond, Z can additionally also be a direct bond;
m is zero, 1 or 2;
p is 1, or p is also zero when X and Y are —N($R_7$)— and —N($R_8$)—, respectively,
$R_6$ is hydrogen, $C_1$-$C_{12}$alkyl, or —C(O)—C($R_9$)=C(H)$R_{10}$, or when Y is —N($R_8$)—, forms together with $R_8$ a group —C(O)—CH=CH—CO—, wherein
$R_9$ is hydrogen or methyl, and $R_{10}$ is hydrogen, methyl or —CO—$X_1$—$R_{11}$, wherein
$R_{11}$ is hydrogen or $C_1$-$C_{12}$alkyl,
$R_7$ and $R_8$ independently of each other are hydrogen, $C_1$-$C_{12}$alkyl, $C_3$-$C_{12}$alkyl interrupted by 1 to 3 oxygen atoms, cyclohexyl, unsubstituted $C_7$-$C_{15}$phenylalkyl, or $C_7$-$C_{15}$phenylalkyl with the phenyl moiety substituted once, twice, three times or four times with $C_1$-$C_4$alkyl and $R_7$ together with $R_8$ in case where Z is ethylene, also forms ethylene;
$A_1$, $A_2$, $A_3$ and $A_4$ are defined to form a saturated or unsaturated, alicyclic or heterocyclic, non-aromatic, aromatic or heteroaromatic ring in formula (I) by being, independently from each other, CH, $CH_2$, $CHR_{12}$, $CR_{12}$, $C(R_{12})_2$, COH, $COR_{12}$, $CCO_2H$, $CCO_2R_{12}$, $CNH_2$, $CNHR_{12}$, $CN(R_{12})_2$, N, $NR_{12}$, CO, $C(SO_2)R_{12}$, or C-Hal with Hal being F, Cl or Br, with $R_{12}$ being defined independently for $A_1$, $A_2$, $A_3$ and $A_4$ by $R_1$, $R_2$ or $R_1$ with one or more hydrogen atoms in $R_1$ being optionally replaced by halogen, like F, Cl or Br;
wherein $A_1$, $A_2$, $A_3$ and $A_4$ can be preferably defined to form a compound according to formula (II) having an additional ring defined by substituents $B_1$, $B_2$, $B_3$ and $B_4$,

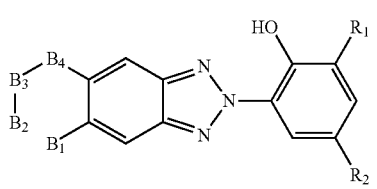

(II)

wherein $B_1$, $B_2$, $B_3$ and $B_4$ form an additional five-membered or six-membered, saturated or unsaturated, alicyclic or heterocyclic, non-aromatic, aromatic or heteroaromatic ring in formula (II) with $B_1$, $B_2$, $B_3$ and $B_4$ being, independently from each other, absent, CH, $CH_2$, $CHR_{12}$, $CR_{12}$, $C(R_{12})_2$, COH, $COR_{12}$, $CCO_2H$, $CCO_2R_{12}$, $CNH_2$, $CNHR_{12}$, $CN(R_{12})_2$, N, $NR_{12}$, or CO, with $R_{12}$ being defined independently for $B_1$, $B_2$, $B_3$ and $B_4$ by $R_1$, $R_2$ or $R_1$ with one or more hydrogen atoms in $R_1$ being optionally replaced by halogen, like F, Cl or Br,
the process comprising the step of converting the ortho-hydroxydiarylazo compound according to formula (III) to the benzotriazole compound according to formula (I) by oxidative ring closure in the presence of a metal salt,

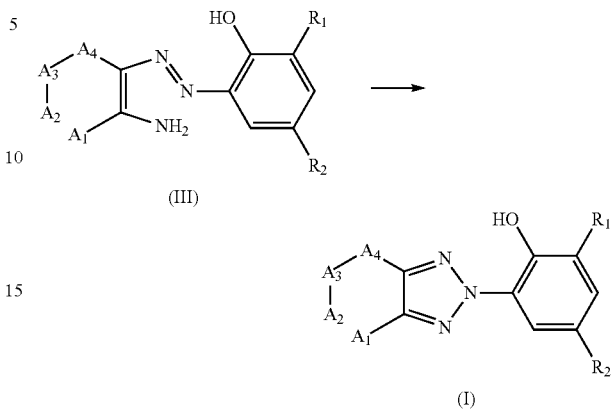

characterized in that the oxidation with metal salt is carried out at a molar ratio of metal salt to diarylazo compound (III) from 0.001 to 4.5, preferably from 0.005 to 1.5, more preferably from 0.01 to 1.0, and most preferably from 0.02 to 0.5.

In a preferred embodiment, the process comprises the novel preceding step of preparing the ortho-hydroxydiarylazo compound according to formula (III) by reacting a 1,2-phenylenediamine compound ((IV) with an ortho-nitrosophenol compound (V) in the presence of a Lewis acid to obtain the diarylazo compound according to formula (III).

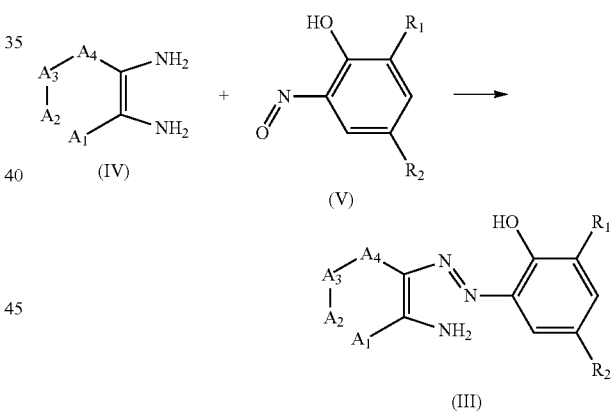

wherein the substitutents $A_1$, $A_2$, $A_3$, $A_4$, $R_1$ and $R_2$ are as defined in claim 1.

In another preferred embodiment, the additional step of preparing the ortho-hydroxydiarylazo compound according to formula (III) including reacting the 1,2-phenylenediamine compound (IV) with the ortho-nitrosophenol compound (V) is carried out in the presence of a Lewis acid selected from $B(OR)_3$, $BF_3$, $BF_3$—$OEt_2$, $Al(OR)_3$, $Al_2O_3$, LiOR, LiF, $Si(OR)_4$, and $Ti(OR)_4$, wherein R is linear or branched $C_1$-$C_{18}$alkyl, perfluoro-alkyl or phenyl, wherein phenyl is optionally substituted once, twice or three times with linear or branched $C_1$-$C_6$ alkyl or fluoride atom; $B(O(O)CR)_3$, $Al(O(O)CR)_3$, $LiO(O)CR$, or $Ti(O(O)CR)_4$, wherein R is linear or branched $C_1$-$C_{17}$alkyl, perfluoro-alkyl or phenyl, wherein phenyl is optionally substituted once, twice or three times with linear or branched $C_1$-$C_6$alkyl or fluoride, or mixtures thereof;

In another preferred embodiment, the Lewis acid is selected from $B(OR)_3$, and LiOR, wherein R is linear or branched $C_1$-$C_{18}$alkyl, perfluoro-alkyl or phenyl, wherein phenyl is optionally substituted once, twice or three times with linear or branched $C_1$-$C_6$ alkyl or fluoride atom; $B(O(O)CR)_3$, $Al(O(O)CR)_3$, and LiO(O)CR, wherein R is linear or branched $C_1$-$C_{17}$alkyl, perfluoro-alkyl or phenyl, wherein phenyl is optionally substituted once, twice or three times with linear or branched $C_1$-$C_6$alkyl or fluoride, more preferably from $B(OR)_3$, wherein R is linear or branched $C_1$-$C_{18}$alkyl or phenyl, wherein phenyl is optionally substituted once, twice or three times with linear or branched $C_1$-$C_6$ alkyl or fluoride atom; and $B(O(O)CR)_3$, wherein R is linear or branched $C_1$-$C_{17}$alkyl or phenyl, wherein phenyl is optionally substituted once, twice or three times with linear or branched $C_1$-$C_6$alkyl or fluoride.

In another preferred embodiment, the metal salt is selected from a transition metal salt comprising the cation $Cu^{1+/2+}$, $Mn^{(2+)-(7+)}$, $Fe^{2+/3+}$, $Ni^{2+/4+}$, $Ru^{3+}$ or $Co^{2+/3+}$, $Zn^{2+}$, preferably $Cu^{1+/2+}$ or $Fe^{2+/3+}$.

In another preferred embodiment, the oxidation with metal salt is carried out under atmospheric conditions.

In another preferred embodiment, the oxidation with a sub-stoichiometric amount of metal salt is carried out in the presence of an oxygen releasing agent like hydrogen peroxide and/or urea peroxide.

In another preferred embodiment, the oxidation with a sub-stoichiometric amount of metal salt is carried out in the presence of at least one atmosphere of air or oxygen.

In another preferred embodiment, the oxidation is carried out with a metal salt complexed by a ligand, wherein the ligand is preferably selected from $NR_3$, wherein R is H or linear or branched $C_1$-$C_{17}$alkyl, unsubstituted phenyl, or phenyl substituted once, twice or three times with linear or branched $C_1$-$C_6$alkyl, bidentate amines, like for instance $R_2N(CH_2)_nNR_2$, wherein R is linear or branched $C_1$-$C_{17}$alkyl, unsubstituted phenyl, phenyl substituted once, twice or three times with $C_1$-$C_6$alkyl, aromatic amines, like pyridine, pyrimidine, N-alkylimidazoles and the like.

In another preferred embodiment, the counterion in the metal salt is selected from $SO_4^{2-}$; $HSO_4^-$, O(O)CR, wherein R is linear or branched $C_1$-$C_{17}$alkyl, perfluoro-alkyl, unsubstituted phenyl, phenyl substituted once, twice or three times with linear or branched $C_1$-$C_6$alkyl, acetylacetonate (acac), $CN^-$, halides, and mixtures thereof.

In another preferred embodiment, in the compound according to formula (I),

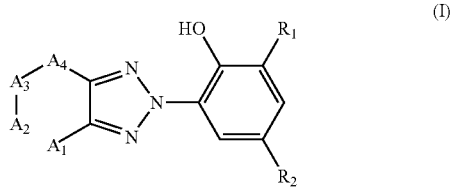

(I)

$R_1$ and $R_2$ are defined as in claim 1, and $A_1$, $A_2$, $A_3$ and $A_4$ form another six-membered aromatic ring with $A_1$, $A_2$, $A_3$ and $A_4$ being defined independently from each other by aromatic $=C(H)-$, aromatic $=C(R_{12})-$, aromatic $=C(OH)-$, aromatic $=C(OR_{12})-$, aromatic $=C(CO_2H)-$, aromatic $=C((SO_2)R_{12})-$, and aromatic $=C(CO_2R_{12})-$, wherein $R_{12}$ is defined independently for $A_1$, $A_2$, $A_3$ and $A_4$ by $R_1$, $R_2$ or $R_1$ with one or more hydrogen atoms in $R_1$ being optionally replaced by halogen, like F, Cl and Br.

In another preferred embodiment, the compound is selected from the following list of structures:

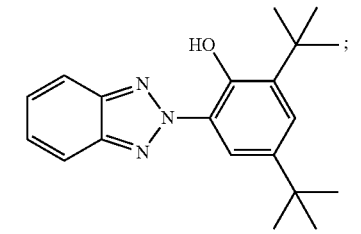

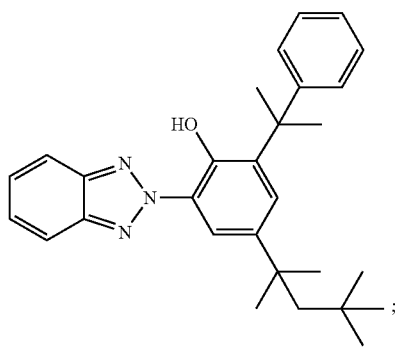

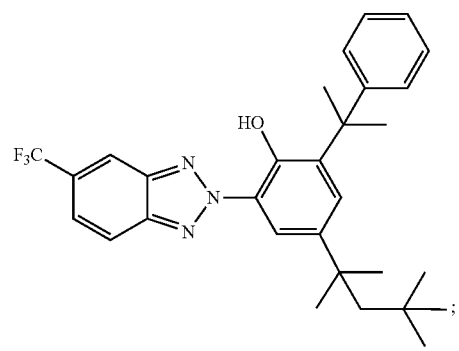

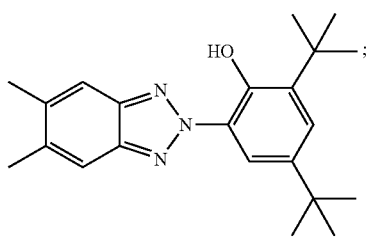

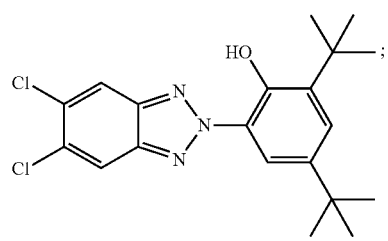

7
-continued
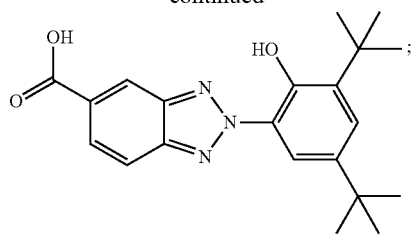
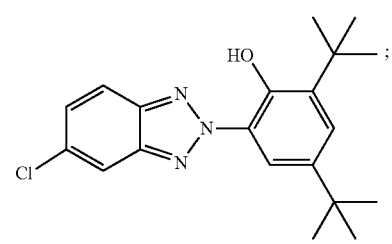
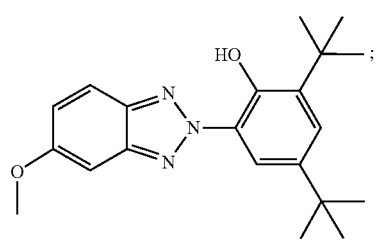
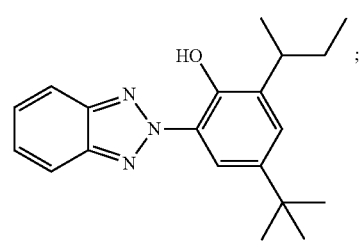
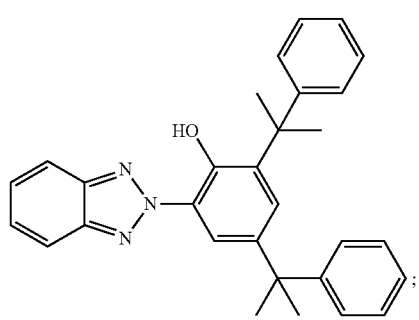
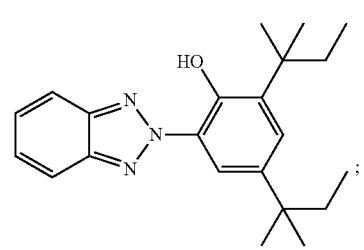
8
-continued
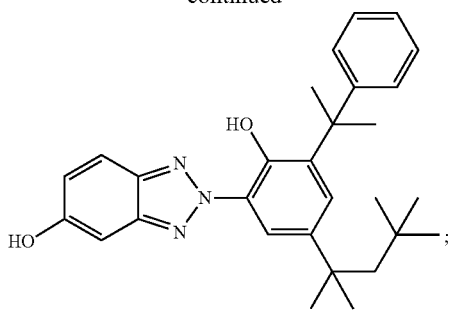
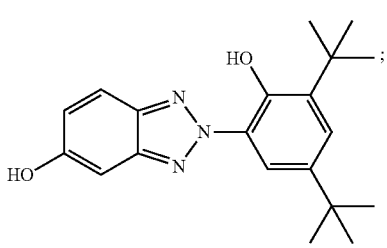
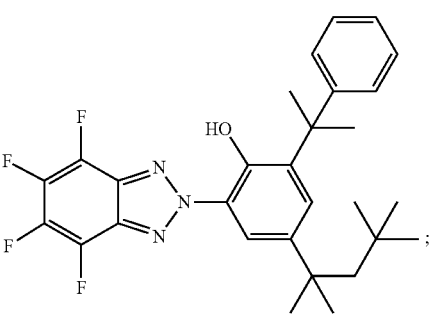
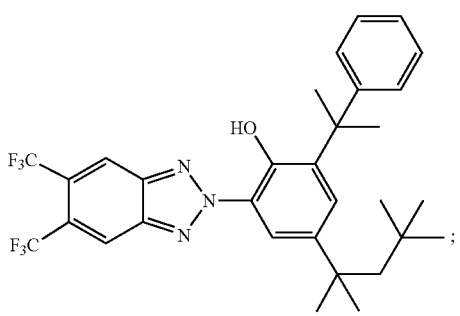
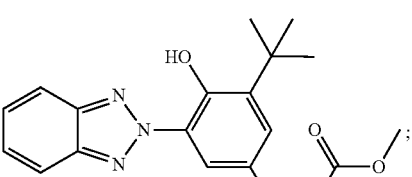
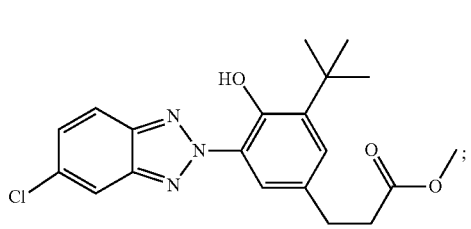

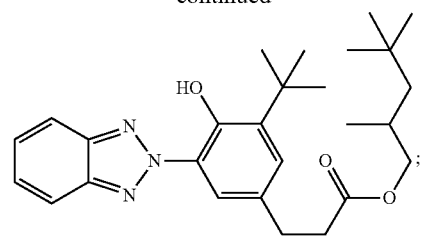

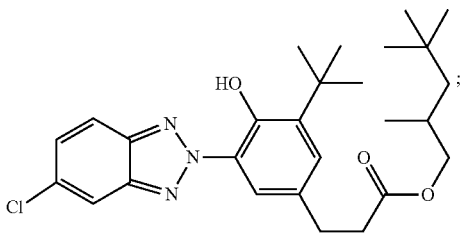

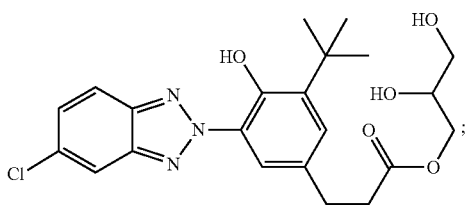

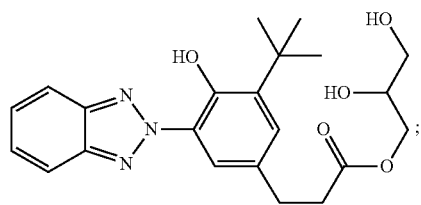

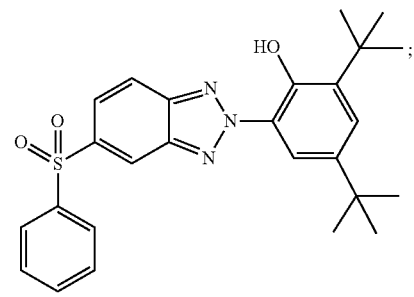

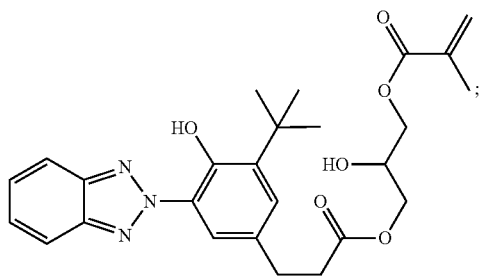

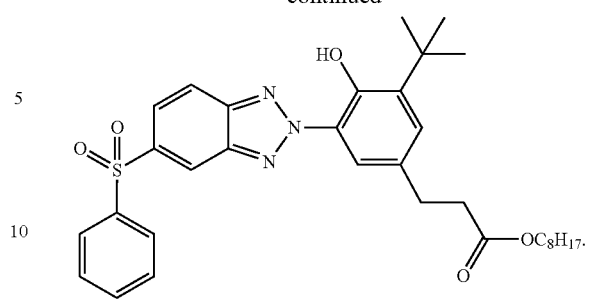

In another preferred embodiment, in the compound according to formula (I),

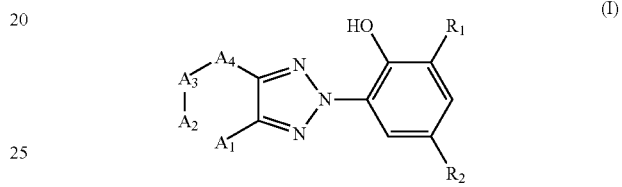

$R_1$ and $R_2$ are defined as in claim 1, and $A_1$, $A_2$, $A_3$ and $A_4$ form another six-membered heteroaromatic or non-aromatic, heterocyclic ring containing one or two additional nitrogen atoms in formula (I) with $A_1$, $A_2$, $A_3$ and $A_4$ being defined independently from each other by one or two aromatic nitrogen(s) =N—, or non-aromatic =N—$R_{12}$, together with non-aromatic —C(O)—, aromatic =C(H)—, aromatic =C($R_{12}$)—, aromatic =C(OH)—, aromatic =C(O$R_{12}$)—, aromatic =C(CO$_2$H)—, aromatic =C((SO$_2$)$R_{12}$)— and/or aromatic =C(CO$_2R_{12}$)—, wherein $R_{12}$ is defined independently for $A_1$, $A_2$, $A_3$ and $A_4$ by $R_1$, $R_2$ or $R_1$ with one or more hydrogen atoms in $R_1$ being optionally replaced by halogen, like F, Cl and Br.

In another preferred embodiment, the compound is selected from the following structures:

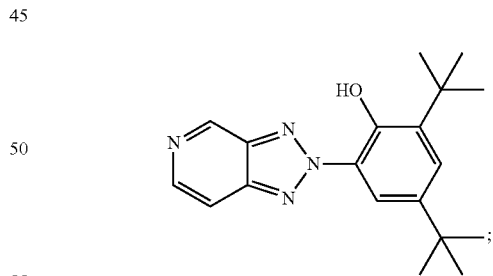

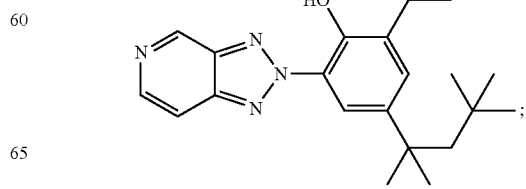

-continued

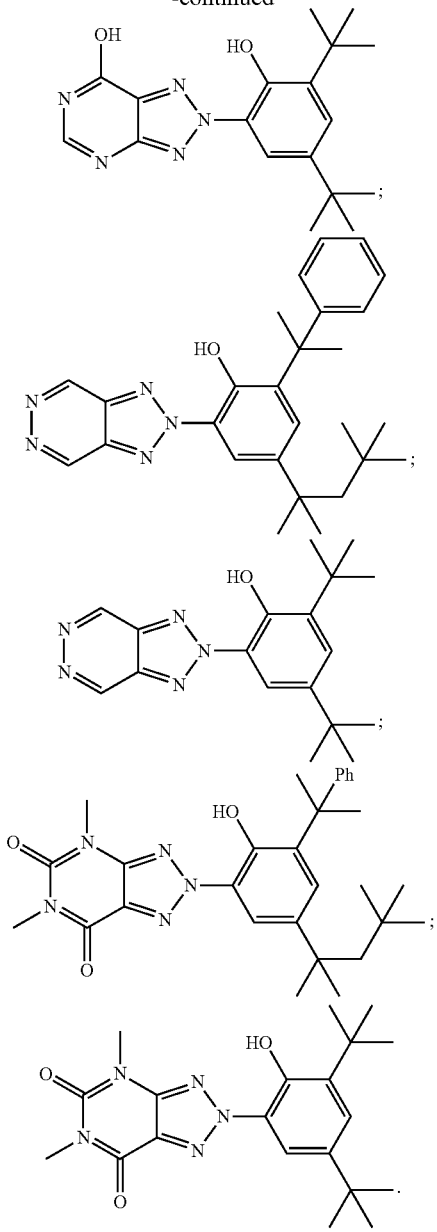

In another preferred embodiment, the compound according to formula (I) is defined by the following formula (II)

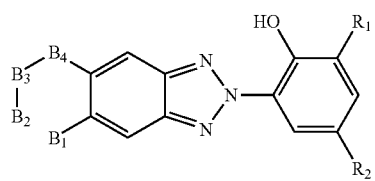

(II)

wherein $B_1$, $B_2$, $B_3$ and $B_4$ form an additional five- or six-membered, saturated or unsaturated, alicyclic or heterocyclic, non-aromatic, aromatic or heteroaromatic ring in formula (II) by $B_1$, $B_2$, $B_3$ and $B_4$ being, independently from each other, absent, CH, $CH_2$, $CHR_{12}$, $CR_{12}$, $C(R_{12})_2$, COH, $COR_{12}$, $CCO_2H$, $CCO_2R_{12}$, $CNH_2$, $CNHR_{12}$, $CN(R_{12})_2$, N, $NR_{12}$, or CO, with $R_{12}$ being defined independently for $B_1$, $B_2$, $B_3$ and $B_4$ by $R_1$, $R_2$ or $R_1$ with one or more hydrogen atoms in $R_1$ being optionally replaced by halogen, like F, Cl or Br.

In another preferred embodiment, the compound according to formula (II), is defined by the following formula (VI),

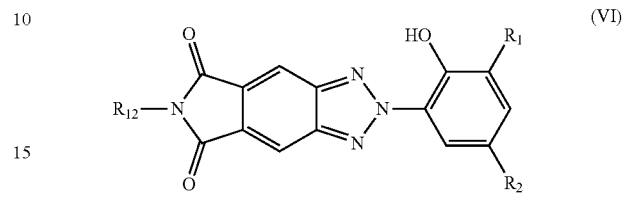

(VI)

wherein $R_1$ and $R_2$ are defined as in claim 1 and $R_{12}$ is defined by $R_1$, $R_2$ or $R_1$ with one or more hydrogen atoms in $R_1$ being optionally replaced by halogen, like F, Cl or Br.

In another preferred embodiment, the compound according to formula (II) or (VI) is selected from the following structures:

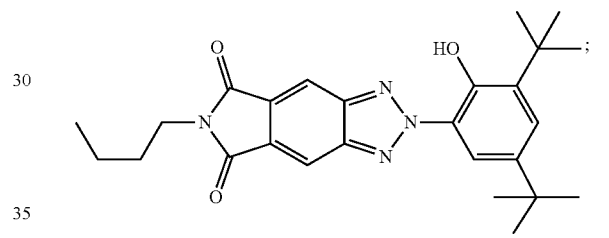

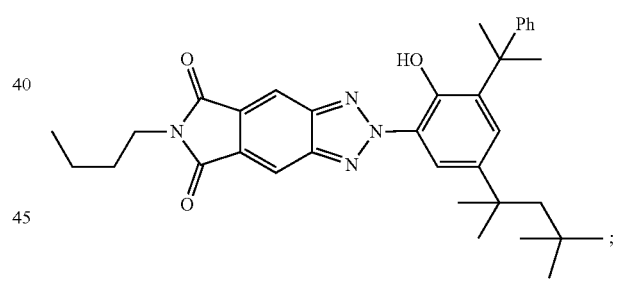

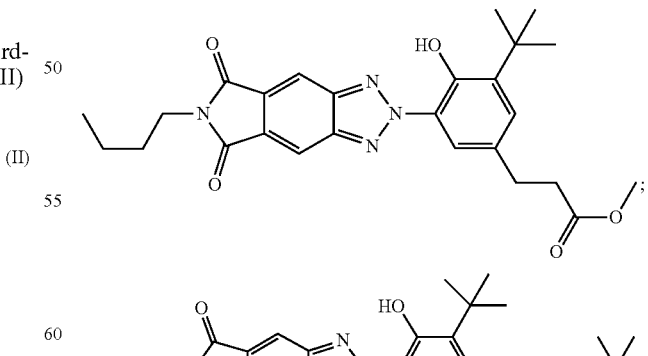

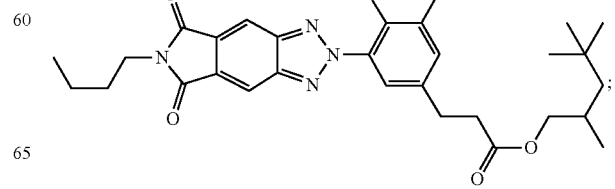

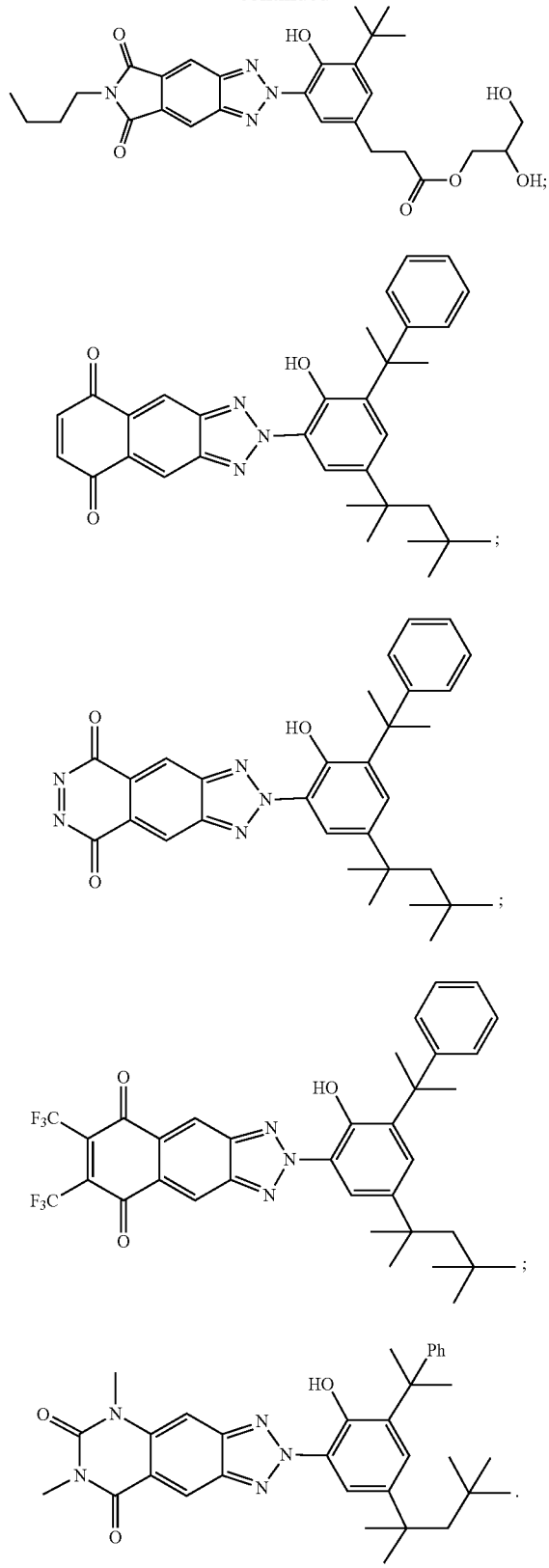

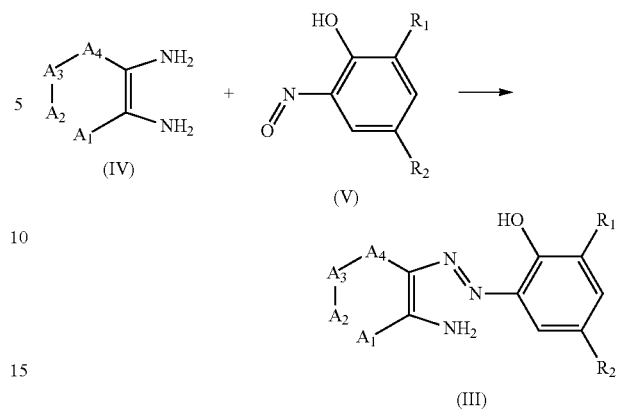

comprising the step of reacting the 1,2-phenylenediamine compound (IV) with an ortho-nitrosophenol compound (V) in the presence of a Lewis acid to obtain the diarylazo compound according to formula (III), wherein $R_1$, $R_2$, $A_1$, $A_2$, $A_3$, and $A_4$ are defined as in claim 1 and the Lewis acid is defined as in claims 2 to 4.

In another aspect, the present invention is also directed to a benzotriazole compound selected from the group of compounds consisting of the following compounds:

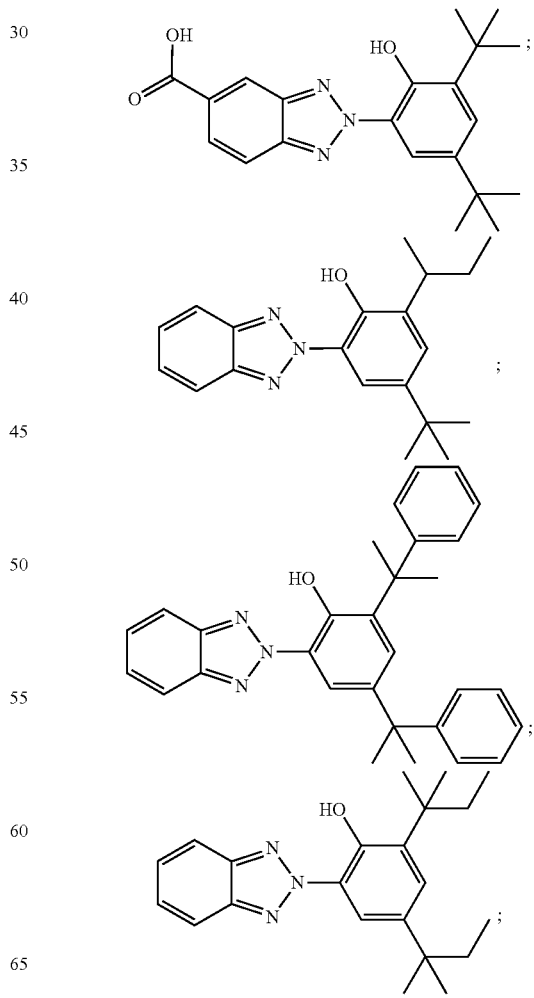

In another aspect, the present invention is also directed to a process for the preparation of the ortho-hydroxydiarylazo compound according to the general formula (III)

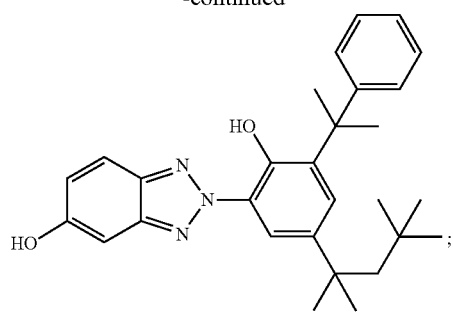
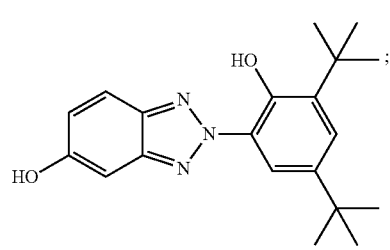
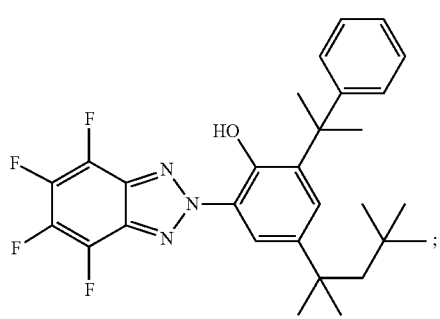
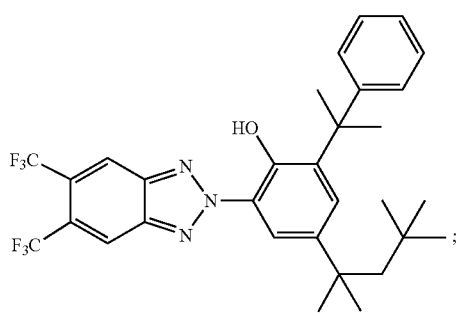
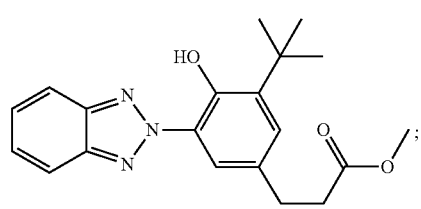
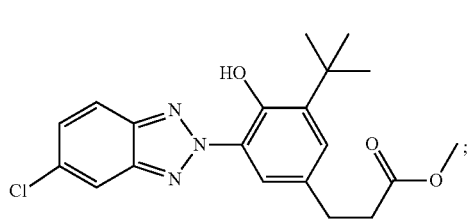
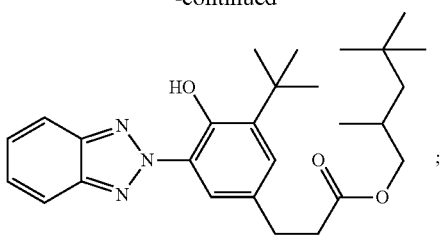
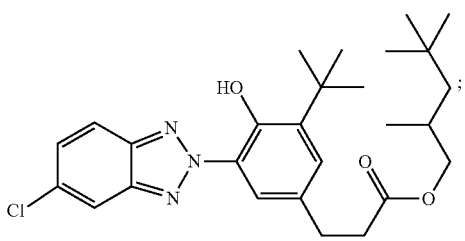
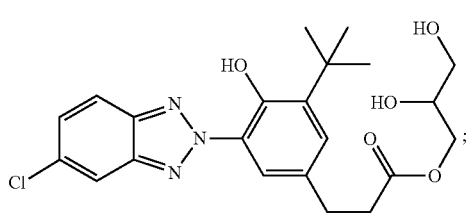
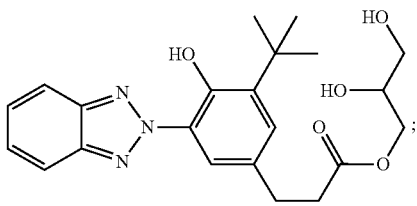
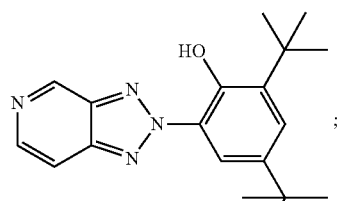
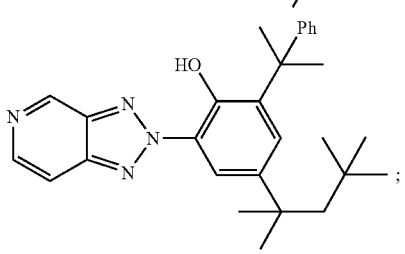
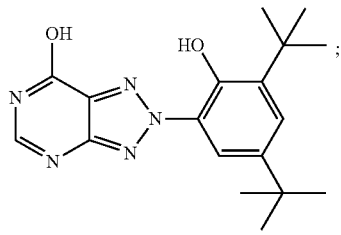

-continued
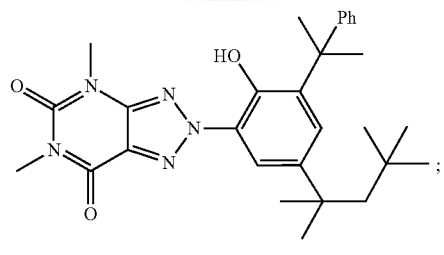
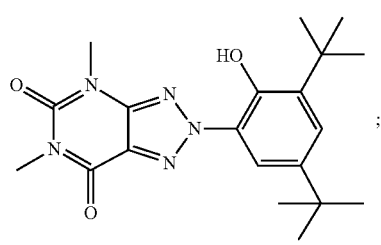
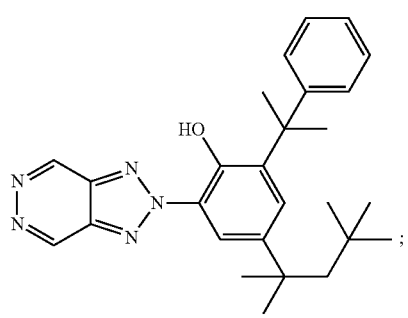
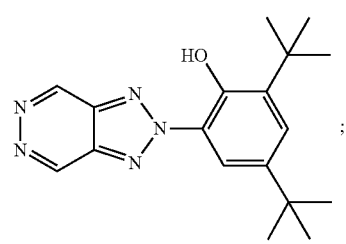
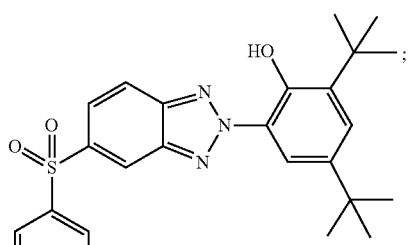
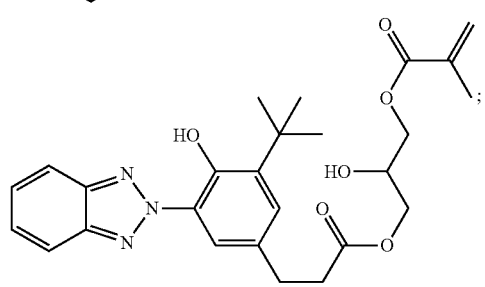
-continued
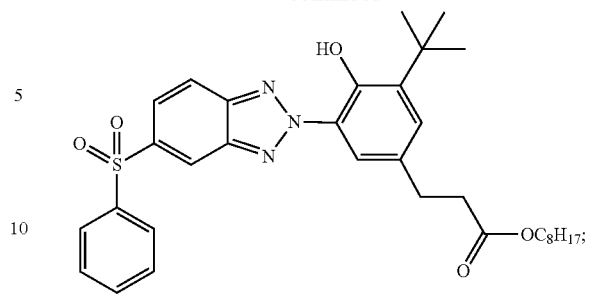
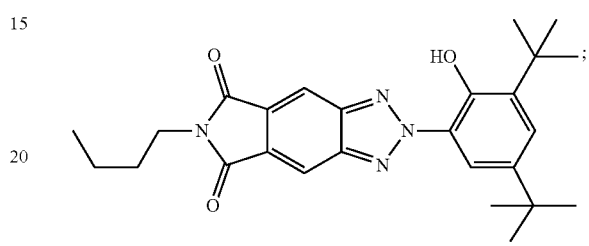
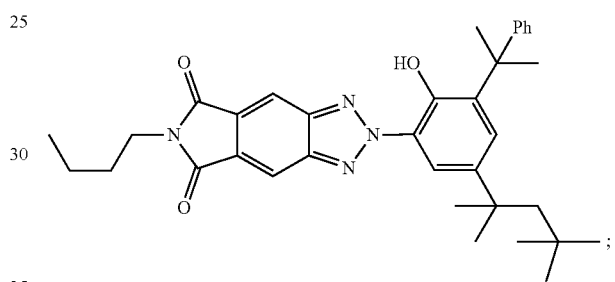
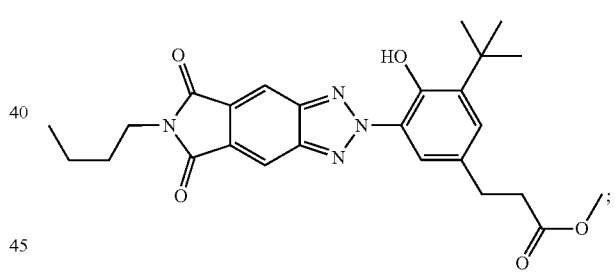
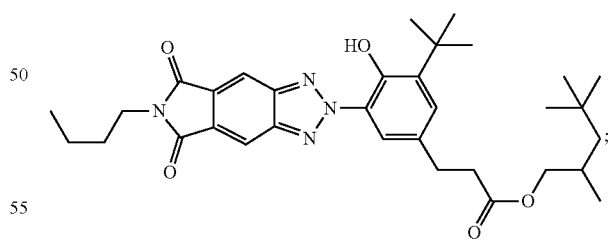
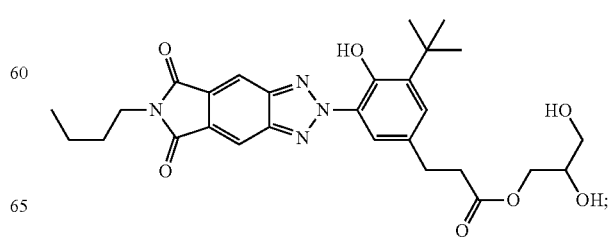

-continued

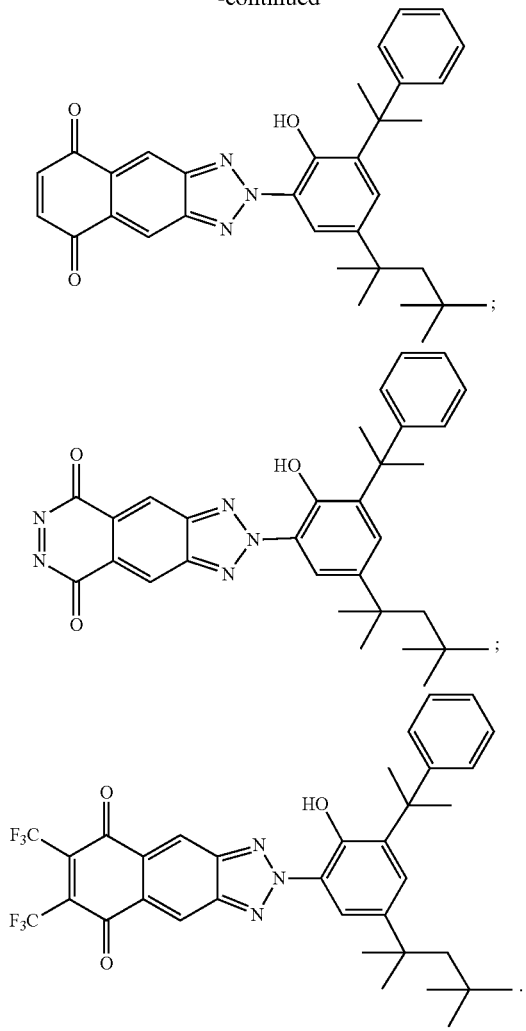

In another aspect, the present invention is also directed to the use of said benzotriazole compounds as ultraviolet (UV) absorber and/or visible light (VIS) absorber in a coating or bulk plastics.

In the following, the present invention is described in more detail.

Preparation of the 2H-Benzotriazole Product from an 1,2-Diarylazo-Aniline Compound In the prior art, benzotriazole compounds have been sometimes prepared from diazoanilines in the presence of very high excess of metal salts leading to oxidative cyclization to the benzotriazole core. However, this reaction is unsuitable for industrial scale while additionally posing environmental challenges. In addition, trace amounts of remnant metal salts in the products severely impair the intended technical use of the materials.

The inventors have modified now this process and found unexpectedly that the oxidative cyclization of an ortho-hydroxydiarylazo (or 1,2-diarylazo-aniline) compound to obtain the corresponding 2H-benzotriazole compound already occurs in catalytic, sub-stoichiometric amounts of metal salt (residues $R_1$, $R_2$, $A_1$, $A_2$, $A_3$ and $A_4$ are as defined in claim 1).

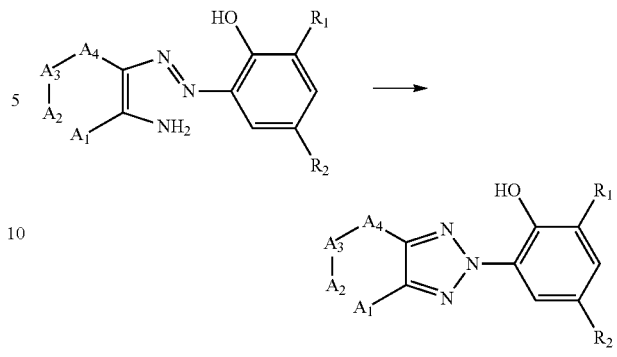

Even more surprisingly, this reaction can be carried out in a straight-forward manner, is broadly applicable to a variety of different structural modifications and the benzotriazole compound is in most cases obtained in very high yields thereby constituting an ideal approach for upscale to the industrial level. In fact, the inventors could demonstrate virtually quantitative conversion to the 2H-benzotriazole compound when catalytic amounts of metal salt were used.

Accordingly, the oxidation of the ortho-hydroxydiarylazo compound (III) to the benzotriazole compound according to formula (I) can be achieved in the presence of metal salt at a molar ratio of metal salt to diarylazo compound (II) from 0.001 to 4.5, preferably from 0.005 to 1.5, more preferably from 0.01 to 1.0, and most preferably from 0.02 to 0.5.

Preferred metal cations of the metal salt used for converting the diarylazo compound according to formula (II) to the benzotriazole compound according to formula (I) are transition metal salts. Preferred metal salts are metal salts comprising transition metal cations selected from $Cu^{1+/2+}$, $Mn^{(2+)-(7+)}$, $Fe^{2+/3+}$, $Ni^{2+/4+}$, $Ru^{3+}$, $Zn^{2+}$, $Co^{2+/3+}$, and mixtures thereof. More preferred are metal salts comprising transition metal cations selected from $Cu^{1+/2+}$, $Fe^{2+/3+}$, $Co^{2+/3+}$ and mixtures thereof, even more preferred are $Cu^{1+/2+}$ and $Fe^{2+/3+}$, and most preferred are metal salts comprising the transition metal cation $Cu^{1+/2+}$.

The selection of the counterion in the metal salt can also have a positive influence on the yield for converting the ortho-hydroxydiarylazo compound according to formula (III) to the benzotriazole compound according to formula (I) and alleviates removal of the metal salts during work-ups. The term counterion refers to the anion part of the metal salt. Preferred counterions in the metal salt generally facilitate good solubility in the solvent. Accordingly, preferred counterions include $SO_4^{2-}$, $HSO_4^-$, $O(O)CR$, wherein R is linear or branched $C_1$-$C_{17}$alkyl, unsubstituted phenyl, phenyl substituted once, twice or three times with linear or branched $C_1$-$C_6$alkyl; acetylacetonate (acac); $CN^-$; halides, and mixtures thereof.

More preferred counterions are $SO_4^{2-}$; $O(O)CR$, wherein R is linear or branched $C_1$-$C_{17}$alkyl, unsubstituted phenyl, phenyl substituted once, twice or three times with linear or branched $C_1$-$C_6$alkyl, acetylacetonate (acac), and mixtures thereof, while the most preferred counterion in the metal salt is $O(O)CR$, wherein R is linear or branched $C_1$-$C_{17}$alkyl, unsubstituted phenyl, or phenyl substituted once, twice or three times with linear or branched $C_1$-$C_6$alkyl.

The conversion of the ortho-hydroxydiarylazo compound according to formula (III) to the benzotriazole compound according to formula (I) in the presence of metal salts can be optionally carried out in the additional presence of complexing ligands. Preferred ligands include $NR_3$, wherein R is H or linear or branched $C_1$-$C_{17}$alkyl, unsubstituted phenyl, phenyl substituted once, twice or three times with linear or branched $C_1$-$C_6$alkyl; and aromatic amines, like pyridine, pyrimidine, N-alkylimidazoles and the like.

The ligands are preferably applied in slight excess, like for instance in an excess of 2 to 15 mol %, more preferably from 5 to 12 mol %, or even more preferably from 8 to 10% mol, relative to the metal cation of the metal salt.

The ligands can also be used as co-solvents in the reaction. Suitable ligands for use as co-solvents include pyridine, N-methyl imidazole or $NR_3$, wherein R is H or linear or branched $C_1$-$C_{17}$alkyl, ligands encompassing bidentate amines, like for instance $R_2N(CH_2)_nNR_2$, wherein R is linear or branched $C_1$-$C_6$alkyl, unsubstituted phenyl, phenyl substituted once, twice or three times with $C_1$-$C_6$alkyl, pyridine, pyrimidines, imidazoles, N—$(CH_2)_n$—N-imidazoles, wherein n is 2 to 3, and mixtures thereof. Most preferred ligands used as co-solvents are $NR_3$, wherein R is linear or branched $C_1$-$C_8$alkyl, pyridine, N-methyl imidazole, and mixtures thereof.

Depending on the educt solubilities and metal salt/ligand combinations, organic and/or hydroxylic solvents may be used as well as mixtures thereof. Preferred solvents include mixtures of ammonia, water and alcohol having the general structure R—OH, wherein R is linear or branched $C_1$-$C_{12}$alkyl, mixtures of pyridine and alcohol having the general formula R—OH, wherein R is linear or branched $C_1$-$C_{12}$alkyl, and mixtures of N-methyl-imidazole and alcohol having the general formula R—OH, wherein R is linear or branched $C_1$-$C_{12}$alkyl, whereas in all of these mixtures, the alcohol R—OH can be partially or completely replaced by THF, methyl-THF or dioxane. Even more preferred solvent combinations are: EtOH-water-$NH_3$ mixtures, $^i$PrOH-water-$NH_3$ mixtures, EtOH-pyridine mixtures, $^i$PropOH-pyridine mixtures, THF-pyridine mixtures, EtOH—N-methylimidazole mixtures, $^i$PropOH—N-methylimidazole mixtures, THF-methylimidazole mixtures, EtOH-$Et_3$N mixtures, $^i$PropOH-$Et_3$N mixtures, THF-$Et_3$N mixtures, methyl-THF-$Et_3$N mixtures, and methyl-THF-pyridine mixtures.

In some cases, the inventors have found that it is most preferred to perform the reductive cyclization to the benzotriazole compound under strictly anhydrous conditions. Accordingly, in these cases, it is most preferred to apply dry solvents and ligands and/or additives like molecular sieves are further added.

Regarding the reaction temperature for converting the ortho-hydroxydiarylazo (or 1,2-diarylazo-aniline) compound to the corresponding 2H-benzotriazole compound, a broad temperature range is applicable. Preferably, the reaction temperature should be in the range from 20° C. (room temperature) to 100° C., more preferably from 30° C. to 90° C., even more preferably from 40° C. to 80° C., and most preferably from 50° C. to 75° C.

Interestingly, the inventors have further found that atmospheric oxygen is normally already sufficient to complete the oxidative cyclization to the benzotriazole product when a catalytic amount of metal salt is present. However, it is possible and more preferred to accelerate the oxidation process by an enhanced level of oxygen in the reaction mixture. Accordingly, it is favorable to conduct the oxidation process at 1-2 atmospheres of oxygen, which is 101,325 kPa to 202.65 kPa, above the reaction surface.

It is also possible to add oxygen complexes (or oxygen releasing agents) to the reaction mixture, for instance, by adding soluble and easily dosable oxygen complexes, like hydrogen peroxide and/or urea hydrogen peroxide, or similar compounds.

Reacting the 1,2-Phenylene Diamine Compound with the 1,2-Nitrosophenol Compound

As described above, the benzotriazole compound according to formula (I) can be obtained in a straight-forward manner from the corresponding ortho-hydroxydiarylazo compound (III) in the presence of a catalytic amount of metal salt.

In contrast thereto, the precursor for the benzotriazole compound in this reaction, the ortho-hydroxydiarylazo compound (III), turned out to be more difficult to prepare since extending basic available procedures from the prior art were found by the inventors to be unsuitable for the ortho-hydroxy substituted diarylazo compounds according to general formula (III). For instance, according to the following very basic synthetic scheme, aniline is converted with nitrosobenzene to the corresponding diazocompound in the presence of acetic acid (see for instance: Houben-Weyl 1965, Band 10/3, 332-338):

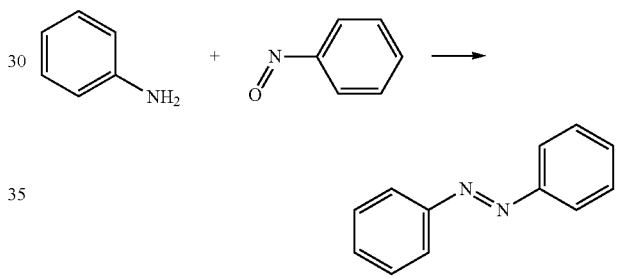

The inventors have also applied this approach for the synthesis of the ortho-hydroxydiarylazo compound (III) but compound (III) could not be obtained. The inventors have found in their studies that due to the ortho-hydroxy substitution of the nitroso compound, no ortho-hydroxydiarylazo compound (III) is obtained according to above's equation because due to the tautomerism of the ortho-hydroxy nitroso compound with the corresponding ortho-chinoxime, a double addition of the phenylene diamine precursor to the ortho-chinoxime occurs. Nonetheless, the present inventors have developed an alternative straight-forward approach making the ortho-hydroxydiarylazo compound (III) easily accessible by reacting the broadly available 1,2-phenylene diamine compound (IV) with an ortho-nitrosophenol compound (V) (residues $R_1$, $R_2$, $A_1$, $A_2$, $A_3$ and $A_4$ are as defined in claim 1).

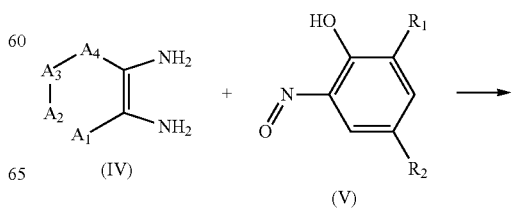

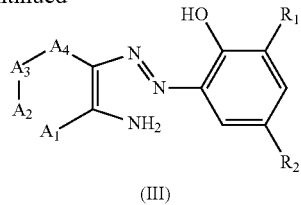

(III)

The 1,2-phenylenediamine compound (IV) and the ortho-nitrosophenol compound (V) are essential in this reaction step and the desired ortho-hydroxydiarylazo compound (III) could be finally obtained by applying the inventive reaction conditions. The inventive reaction can be carried out with high yield under mild reaction conditions and is broadly applicable. In this new approach, the 1,2-phenylenediamine compound (IV) and the ortho-nitrosophenol compound (V) are reacted in the presence of a carefully selected Lewis acid.

Without wishing to be bound by a certain theory, the additional presence of a mild Lewis acid helps to avoid the formation of those undesired products from reacting ortho-nitroso phenols with 1,2-phenylene diamines. The selected mild oxophilic Lewis acids are also selected to not complex the 1,2-phenylene diamine compound (IV). Instead, the reaction is directed towards the desired ortho-hydroxydiarylazo compounds (III) in very high yields, for many compounds in near quantative yields, whereas only surprisingly mild and straight-forward reaction conditions need to be applied.

Another important advantage is that the mild reaction conditions and the mild Lewis acid are compatible with many temperature- and acid-sensitive functional groups within the final desired benzotriazole system (I) thereby allowing to apply this reaction for the preparation of a wide range of structurally diverse benzotriazole compounds. For the first time, a preparative automatable process for obtaining benzotriazole compounds becomes possible giving rise to access large libraries of ortho-hydroxydiarylazo compounds of the general formula (III) via high-through-put screenings (HTS) which allows meeting customer requests desired for highly specialized applications. Intermediate compounds (III) can subsequently be cyclized oxidatively in the presence of metal salts as is described herein.

The aromatic system carrying the diamino functionality can be either electron rich or electron poor. In a preferred embodiment, the neighboring positions of the amino groups of the 1,2-phenylene diamine compound should be unsubstituted, i.e. occupied be hydrogen to achieve the highest yields. The 1,2-phenylene diamine compound may be commercially available or be synthesized by appropriate routes known by the skilled artist.

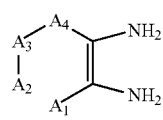

(IV)

Preferred 1,2-phenylene diamine compounds (IV) in the inventive process are defined by having $A_1$, $A_2$, $A_3$ and $A_4$ as follows: $A_1$, $A_2$, $A_3$ and $A_4$ form a saturated or unsaturated, alicyclic or heterocyclic, non-aromatic, aromatic or heteroaromatic ring in formula (IV) by being, independently from each other, CH, $CH_2$, $CHR_{12}$, $CR_{12}$, $C(R_{12})_2$, COH, $COR_{12}$, $CCO_2H$, $CCO_2R_{12}$, $CNH_2$, $CNHR_{12}$, $CN(R_{12})_2$, $C(SO_2)R_{12}$, N, $NR_{12}$, CO, or C-Hal with Hal being F, Cl or Br, with $R_{12}$ being defined independently for $A_1$, $A_2$, $A_3$ and $A_4$ by $R_1$, $R_2$ or $R_1$ with one or more hydrogen atoms in $R_1$ being optionally replaced by halogen, like F, Cl or Br.

Residue $R_1$ is hydrogen, linear or branched $C_1$-$C_{24}$alkyl, linear or branched $C_2$-$C_{18}$alkenyl, $C_5$-$C_{12}$cycloalkyl, unsubstituted $C_7$-$C_{15}$phenylalkyl, $C_7$-$C_{15}$phenylalkyl with the phenyl moiety substituted once, twice, three times or four times with $C_1$-$C_4$alkyl, unsubstituted phenyl, phenyl substituted once, twice, three times or four times with $C_1$-$C_4$alkyl.

Residue $R_2$ is, independently from $R_1$, linear or branched $C_1$-$C_{24}$alkyl, linear or branched $C_2$-$C_{18}$alkenyl, $C_5$-$C_{12}$cycloalkyl, unsubstituted $C_7$-$C_{15}$phenylalkyl, $C_7$-$C_{15}$phenylalkyl with the phenyl moiety substituted once, twice, three times or four times with $C_1$-$C_4$alkyl, unsubstituted phenyl, phenyl substituted once, twice, or three times with $C_1$-$C_4$alkyl, wherein alkyl is optionally substituted by one or more —OH, —OCO—$R_3$, —$OR_4$, —NCO, —$NH_2$ or combinations thereof, wherein $R_3$ is hydrogen, linear or branched $C_1$-$C_{16}$alkyl, $C_5$-$C_{12}$cycloalkyl, linear or branched $C_3$-$C_6$alkenyl, phenyl, naphthyl or $C_7$-$C_{15}$phenylalkyl and $R_4$ is hydrogen, linear or branched $C_1$-$C_{24}$ alkyl;
—$OR_4$, —C(O)$OR_4$, —C(O)$NHR_4$ or —C(O)$NR_4R_4$;
—$SR_5$, —$NHR_5$, or —N$(R_5)_2$, wherein $R_5$ is $C_1$-$C_{20}$alkyl, $C_2$-$C_{20}$hydroxyalkyl; $C_3$-$C_{18}$alkenyl, $C_5$-$C_{12}$cycloalkyl, $C_7$-$C_{15}$phenylalkyl, unsubstituted phenyl, unsubstituted naphthyl, phenyl substituted once or twice with $C_1$-$C_4$alkyl, or naphthyl substituted once or twice with $C_1$-$C_4$alkyl;
—(CH$_2$)$_m$—CO—$X_1$—(Z)$_p$—Y—$R_6$, wherein $X_1$ is —O— or —$NR_7$—, Y is —O— or $NR_8$— or a direct bond, Z is $C_2$-$C_{12}$alkylene, $C_1$-$C_{12}$alkylene interrupted by one to three nitrogen atoms, oxygen atoms or combinations thereof, $C_3$-$C_{12}$alkylene, butenylene, butynylene, cyclohexylene or phenylene, wherein each of which may be additionally substituted by a hydroxyl group; or a group selected from the following list of structures:

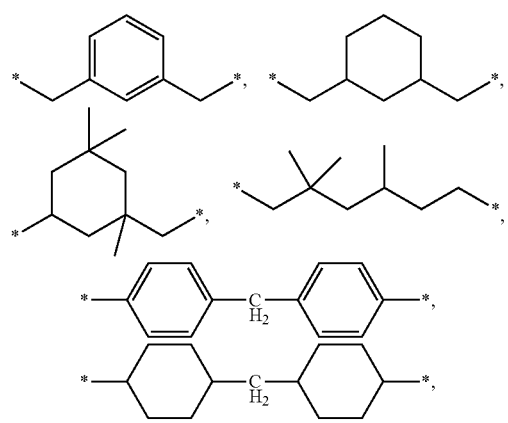

wherein * denotes a bond;
or when Y is a direct bond, Z can additionally also be a direct bond;
m is zero, 1 or 2;
p is 1, or p is also zero when X and Y are —N(R$_7$)— and —N(R$_8$)—, respectively,
R$_6$ is hydrogen, $C_1$-$C_{12}$alkyl, or —C(O)—C(R$_9$)=C(H) R$_{10}$, or when Y is —N(R$_8$)—, forms together with R$_8$ a group —C(O)—CH=CH—CO—, wherein $R_9$ is hydrogen or methyl, and $R_{10}$ is hydrogen, methyl or —CO—$X_1$—$R_{11}$, wherein $R_{11}$ is hydrogen or $C_1$-$C_{12}$alkyl, $R_7$ and $R_8$ independently of each other are hydrogen, $C_1$-$C_{12}$alkyl, $C_3$-$C_{12}$alkyl interrupted by 1 to 3 oxygen atoms, cyclohexyl, unsubstituted $C_7$-$C_{15}$phenylalkyl, or $C_7$-$C_{15}$phenylalkyl with the phenyl moiety substituted once, twice, three times or four times with $C_1$-$C_4$alkyl and $R_7$ together with $R_8$ in case where Z is ethylene, also forms ethylene.

In a preferred embodiment, $A_1$, $A_2$, $A_3$ and $A_4$ can be preferably defined to form a compound according to formula (IVa) having an additional ring defined by substituents $B_1$, $B_2$, $B_3$ and $B_4$,

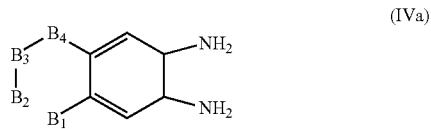

(IVa)

wherein $B_1$, $B_2$, $B_3$ and $B_4$ form an additional five-membered or six-membered, saturated or unsaturated, alicylic or heterocyclic, non-aromatic, aromatic or heteroaromatic ring in formula (IVa) by $B_2$, $B_3$ and $B_4$ being, independently from each other, absent, CH, CH$_2$, CHR$_{12}$, CR$_{12}$, C(R$_{12}$)$_2$, COH, COR$_{12}$, CCO$_2$H, CCO$_2$R$_{12}$, CNH$_2$, CNHR$_{12}$, CN(R$_{12}$)$_2$, N, NR$_{12}$, or CO, with R$_{12}$ being defined independently for $B_1$, $B_2$, $B_3$ and $B_4$ by $R_1$, $R_2$ or $R_1$ with one or more hydrogen atoms in $R_1$ being optionally replaced by halogen, like F, Cl or Br, wherein $R_1$ and $R_2$ are as defined above.

In another preferred embodiment, the 1,2-phenylene diamine is defined by the compounds having the formula (IV),

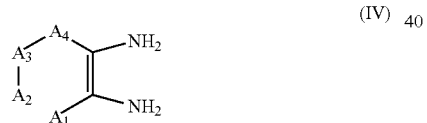

(IV)

wherein $R_1$ and $R_2$ are defined as above, and $A_1$, $A_2$, $A_3$ and $A_4$ form another six-membered aromatic ring with $A_1$, $A_2$, $A_3$ and $A_4$ being defined independently from each other by aromatic =C(H)—, aromatic =C(R$_{12}$)—, aromatic =C(OH)—, aromatic =C(OR$_{12}$)—, aromatic =C(CO$_2$H)—, aromatic =C((SO$_2$)R$_{12}$)— and aromatic =C(CO$_2$R$_{12}$)—, wherein R$_{12}$ is defined independently for $A_1$, $A_2$, $A_3$ and $A_4$ by $R_1$, $R_2$ or $R_1$ with one or more hydrogen atoms in $R_1$ being optionally replaced by halogen, like F, Cl and Br.

In another preferred embodiment, the 1,2-phenylene diamine is defined by the compounds having the formula (IV),

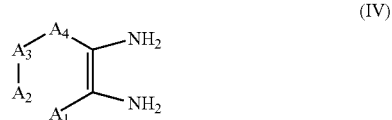

(IV)

wherein $R_1$ and $R_2$ are defined as above, and $A_1$, $A_2$, $A_3$ and $A_4$ form a six-membered heteroaromatic ring containing one or two additional nitrogen atoms in formula (I) with $A_1$, $A_2$, $A_3$ and $A_4$ being defined independently from each other by one or two aromatic nitrogen(s) =N—, together with aromatic =C(H)—, aromatic =C(R$_{12}$)—, aromatic =C(OH)—, aromatic =C(OR$_{12}$)—, aromatic =C(CO$_2$H)—, aromatic =C((SO$_2$)R$_{12}$)— and aromatic =C(CO$_2$R$_{12}$)—, wherein R$_{12}$ is defined independently for $A_1$, $A_2$, $A_3$ and $A_4$ by $R_1$, $R_2$ or $R_1$ with one or more hydrogen atoms in $R_1$ being optionally replaced by halogen, like F, Cl and Br.

In another preferred embodiment, the 1,2-phenylene diamine is defined by the compounds having the formula (IVa)

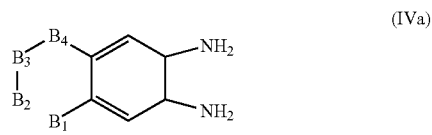

(IVa)

wherein $B_1$, $B_2$. $B_3$ and $B_4$ form an additional five- or six-membered, saturated or unsaturated, alicylic or heterocyclic, non-aromatic, aromatic or heteroaromatic ring in formula (IVa) by $B_1$, $B_2$, $B_3$ and $B_4$ being, independently from each other, absent, CH, CH$_2$, CHR$_{12}$, CR$_{12}$, C(R$_{12}$)$_2$, COH, COR$_{12}$, CCO$_2$H, CCO$_2$R$_{12}$, CNH$_2$, CNHR$_{12}$, CN(R$_{12}$)$_2$, N, NR$_{12}$, or CO, with R$_{12}$ being defined independently for $B_1$, $B_2$, $B_3$ and $B_4$ by $R_1$, $R_2$ or $R_1$ with one or more hydrogen atoms in $R_1$ being optionally replaced by halogen, like F, Cl or Br.

In another preferred embodiment, the 1,2-phenylene diamine is defined by the compounds having the formula (IVb)

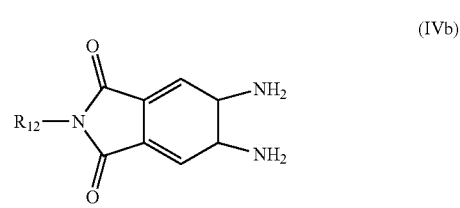

(IVb)

wherein $R_1$ and $R_2$ are defined as above and $R_{12}$ is defined by $R_4$, $R_2$ or $R_1$ with one or more hydrogen atoms in $R_1$ being optionally replaced by halogen, like F, Cl or Br.

Since all reactions are performed in organic media, it is preferred that the 1,2-phenylene diamine compound is soluble in an appropriate inert organic solvent, like for instance alkyl or aryl ethers, cyclic ethers, like tetrahydrofuran, 2-methyltetrahydrofuran, dioxane or chlorinated organic solvents, like dichloromethane, dichloroethane, chlorobenzene, isomeric mixtures of di- or tri-chlorobenzenes, alkyl- or arylnitriles, toluene, xylene and aliphatic solvents, like hexane, heptane, octane, and longer chain linear or branched alkyls or mixtures of the mentioned solvents.

Regarding the second reactant of the inventive process, the ortho-nitrosophenol, the same considerations apply.

Preferred ortho-nitrosophenol compounds (V) according to the present invention have the following formula (V), wherein $R_1$ and $R_2$ are defined as above.

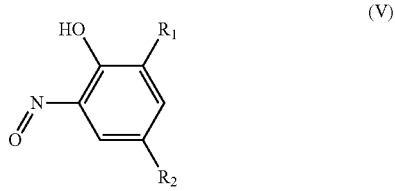

(V)

The ortho-nitrosophenol compound (V) may be commercially available or can also be conveniently prepared by known protocols from appropriately substituted ortho-chinones and hydroxylamine, like it is described elsewhere (see for instance A. Krzan, Acta Chim. Slov. 2001, 48, 229). Alternatively, the ortho-nitrosophenol is generally accessible by the so-called Baudisch-reaction starting from phenol compounds (see for instance K. Maruyama et al. JOC 1967, 32, 2516, or U.S. Pat. No. 5,250,741) or as described elsewhere (see for instance Ya. I. Shipnel et al. Zhurnal Organ, Khimii 1977, 13(5), 1030).

The reaction of the 1,2-phenylene diamine compound (IV) with the 1,2-nitrosophenol compound (V) is preferably carried out in the solvents already mentioned above. Accordingly, solvents that can be preferably used include linear or branched dialkyl ethers, aryl ethers, or more preferably, cyclic ethers, like tetrahydrofuran, methyl tetrahydrofuran, dioxane, or mixtures thereof.

When carrying out the reaction, both reactants, the 1,2-phenylene diamine compound and the ortho-nitrosophenol, can be mixed before addition of the Lewis acid. Alternatively, the ortho-nitrosophenol, or the corresponding oxime compound, which is tautomeric to the ortho-nitrosophenol, is first treated with the Lewis acid in the absence of the 1,2-phenylene diamine compound to first form the active complex followed by the addition of the 1,2-phenylene diamine compound.

It is possible that at least one of the 1,2-phenylene diamine compound and the ortho-nitrosophenol compound is used in the inventive process in an excess from 5 to 50 mol %, more preferably from 10 to 40 mol %, and even more preferably from 20 to 30 mol %, relative to the other reactant. However, it is preferred that both reactants are used in equimolar amounts, or at least near equimolar amounts. In other words, the relative amount of the 1,2-phenylene diamine compound to the ortho-nitrosophenol compound is from 1.05:1 to 1:1.05, more preferably from 1.02:1 to 1:1.02, and most preferably from 1.1:1 to 1:1.1, based on the molar ratio of the 1,2-phenylene diamine compound and the ortho-nitrosophenol compound used when carrying out this inventive process step.

The reaction temperature applied in this process can be selected from room temperature to reflux temperature of the selected solvent(s). A preferred reaction temperature is in the range of 40° C. to 120° C., more preferably from 60° C. to 110° C., and most preferably from 75° C. to 100° C.

Regarding the concentration of the 1,2-phenylene diamine compound and the ortho-nitrosophenol compound, or in other words, the amount of solvent to be applied in the reaction of said two compounds, it is important that the reaction is carried out in sufficient dilution to guarantee a complete dissolution of the 1,2-phenylene diamine compound and the ortho-nitrosophenol compound.

It is especially preferred that the reaction of the 1,2-phenylene diamine compound with the ortho-nitrosphenol compound is carried out in the presence of a suitable Lewis acid. The Lewis acid is preferably applied in an amount of 0.2 to 4.0 equivalents with respect to 1,2-phenylene diamine compound and the ortho-nitrosophenol compound. In case that the 1,2-phenylene diamine compound and the ortho-nitrosophenol compound are not used in equimolar amounts, the amount of Lewis acid to be used is calculated relative to the amount of the ortho-nitrosophenol compound. More preferably, the Lewis acid is applied in an amount of 0.5 to 3.0 equivalents, or more even preferably from 1.0 to 2.0 equivalents.

The following Lewis acids are preferably included for the reaction of the 1,2-phenylene diamine compound and the ortho-nitrosophenol compound: $B(OR)_3$, $Al(OR)_3$, $LiOR$, $Si(OR)_4$, and $Ti(OR)_4$, wherein R is linear or branched $C_1$-$C_{18}$alkyl, perfluoro-alkyl or phenyl, wherein phenyl is optionally substituted once, twice or three times with linear or branched $C_1$-$C_6$ alkyl or fluoride atom; $B(O(O)CR)_3$, $Al(O(O)CR)_3$, $LiO(O)CR$, or $Ti(O(O)CR)_4$, wherein R is linear or branched $C_1$-$C_{17}$alkyl, perfluoro-alkyl or phenyl, wherein phenyl is optionally substituted once, twice or three times with linear or branched $C_1$-$C_6$alkyl or fluoride; additional suitable Lewis acid compounds are $BF_3$, $BF_3$—$OEt_2$, $Al_2O_3$, like commercial $Al_2O_3$ being either in neutral, basic or acidic forms, e.g. available by VWR-Chemicals; LiF, or mixtures of said Lewis acids.

Especially preferred Lewis acids include: $B(OR)_3$ and $LiOR$, wherein R is linear or branched $C_1$-$C_{18}$alkyl, perfluoro-alkyl or phenyl, wherein phenyl is optionally substituted once, twice or three times with linear or branched $C_1$-$C_6$ alkyl or fluoride atom; $B(O(O)CR)_3$ and $LiO(O)CR$, wherein R is linear or branched $C_1$-$C_{17}$alkyl, perfluoro-alkyl or phenyl, wherein phenyl is optionally substituted once, twice or three times with linear or branched $C_1$-$C_6$alkyl or fluoride; $Al_2O_3$, like commercial $Al_2O_3$ either in neutral, basic or acidic forms e.g. available by VWR-Chemicals.

Most preferred Lewis acids include $B(OR)_3$, wherein R is linear or branched $C_1$-$C_{18}$alkyl or phenyl, wherein phenyl is optionally substituted once, twice or three times with linear or branched $C_1$-$C_6$ alkyl or fluoride atom, and $B(O(O)CR)_3$, wherein R is linear or branched $C_1$-$C_{17}$alkyl or phenyl, wherein phenyl is optionally substituted once, twice or three times with linear or branched $C_1$-$C_6$alkyl or fluoride.

The structure and molecular weight of the residue R in the Lewis acids may be generally chosen according to the solubility of the Lewis acid in the reaction medium and/or according to the reaction temperature at which the Lewis acid should not boil out of the reaction medium.

The novel synthetic path is exemplified below, however, is not restricted to the examples given, as is knowledgeable to the skilled person in the art.

In another aspect, the present invention is also directed to a process for the preparation of the ortho-hydroxydiarylazo compound according to the general formula (III)

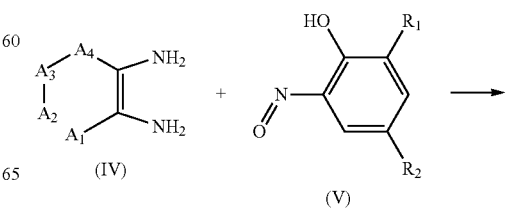

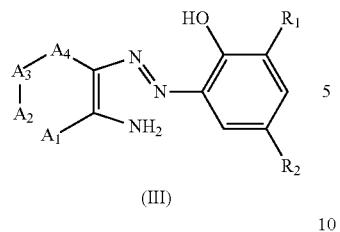

(III)

comprising the step of reacting the 1,2-phenylenediamine compound (IV), or preferably (IVa) or (IVb), with an ortho-nitrosophenol compound (V) in the presence of a Lewis acid to obtain the diarylazo compound according to formula (III), wherein $R_1$, $R_2$, $A_1$, $A_2$, $A_3$, and $A_4$ are defined as above and the Lewis acid as also defined above.

In another aspect, the present invention is also directed to a benzotriazole compound selected from the following group of compounds:

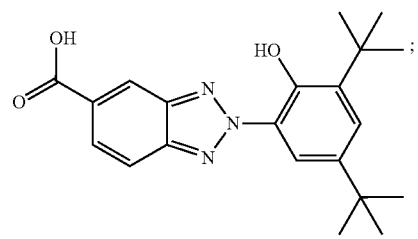

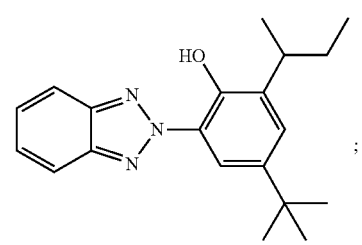

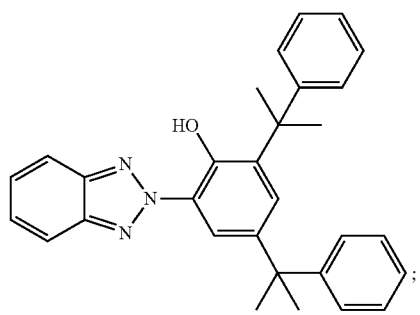

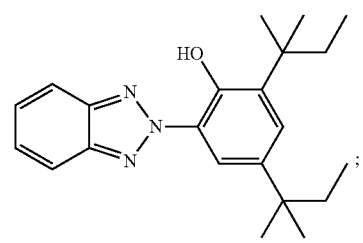

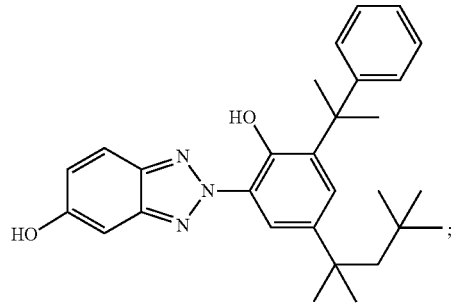

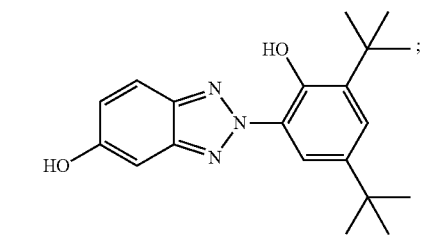

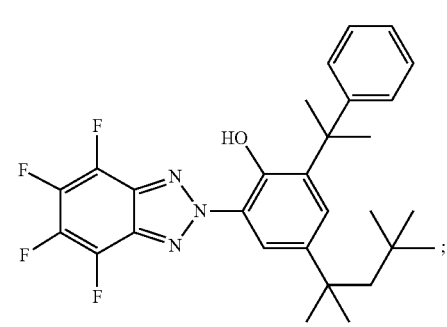

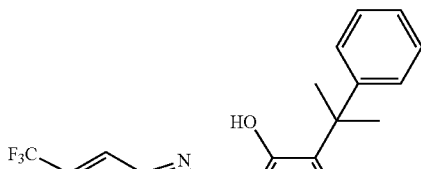

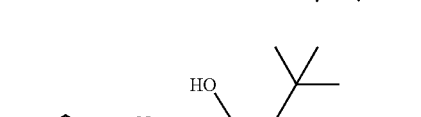

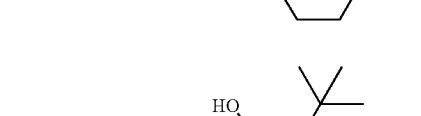

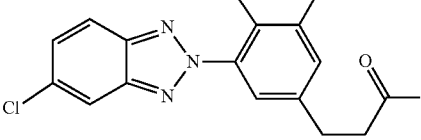

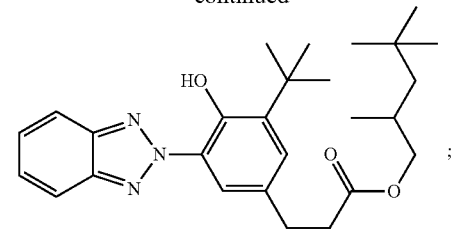
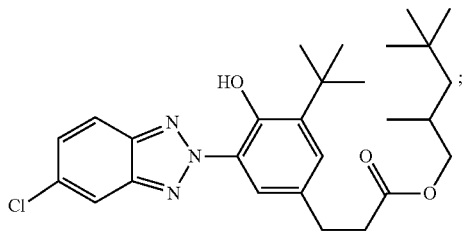
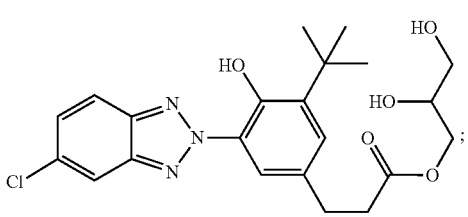
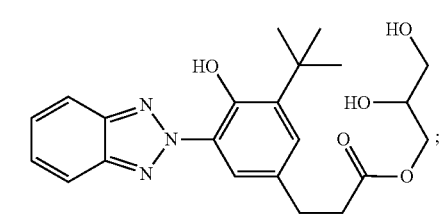
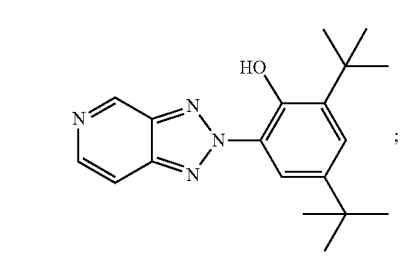
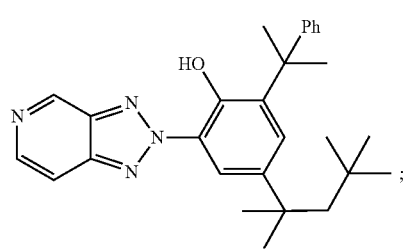
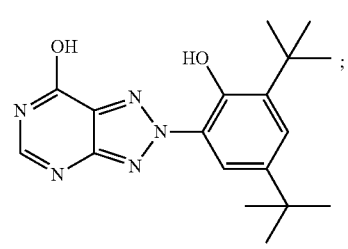
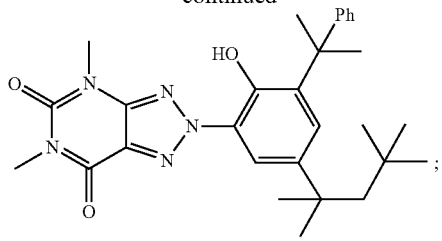
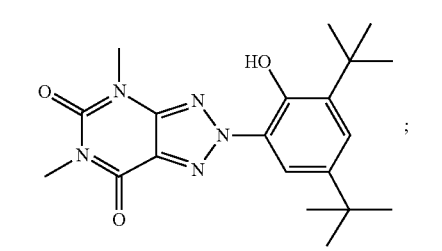
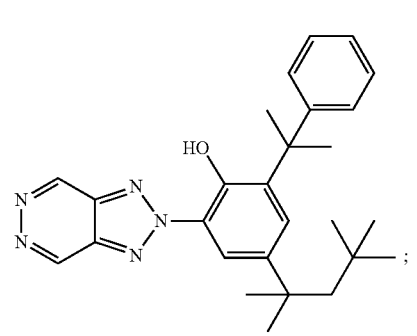
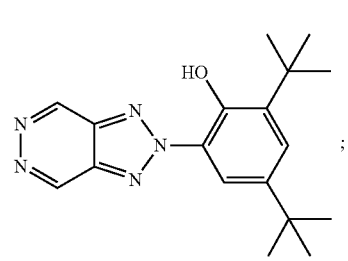
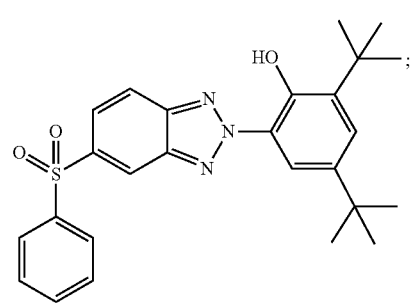
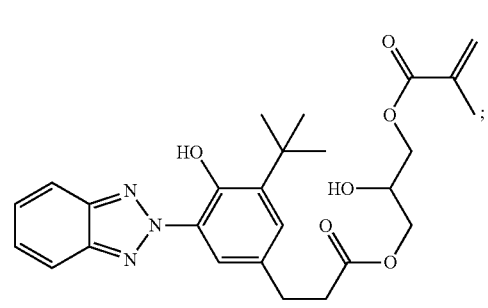

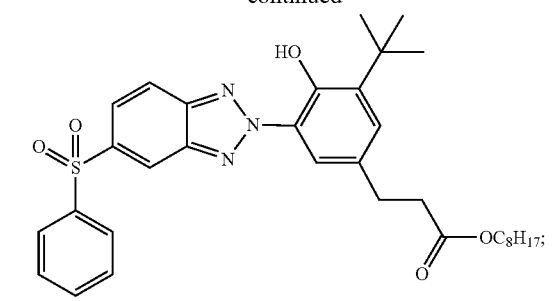
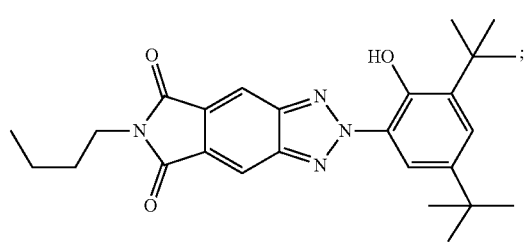
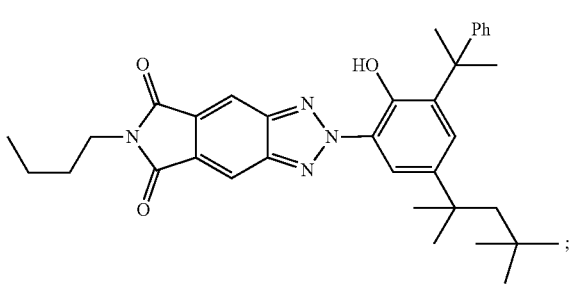
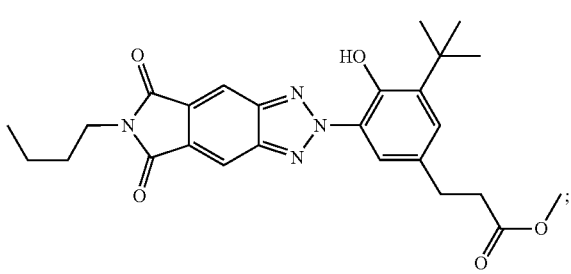
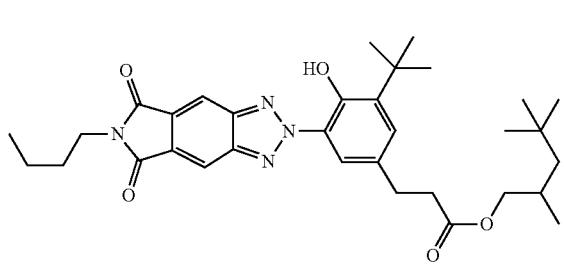
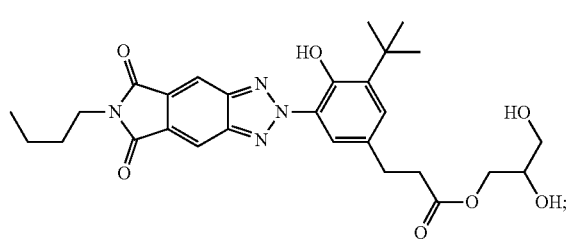

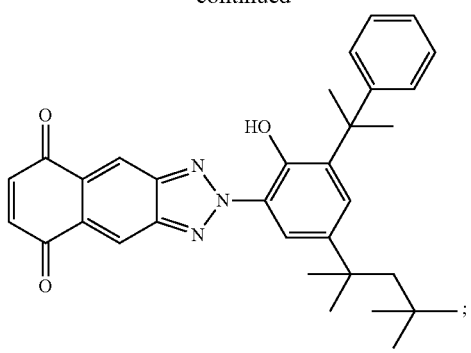
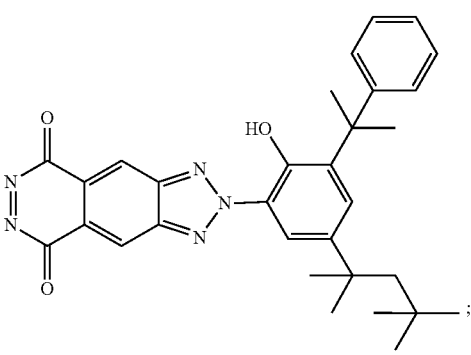
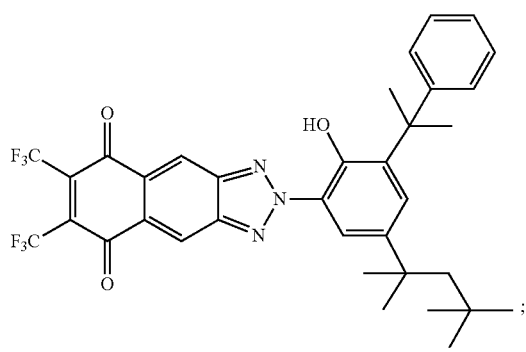
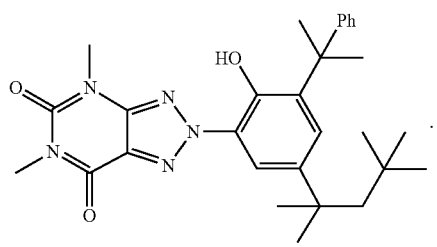

In another aspect, the present invention is also directed to a use of the benzotriazole compound of the present invention as ultraviolet (UV) absorber and/or visible light (VIS) absorber in a coating or bulk plastics. A visible light absorber is also known as an UV protectant. The skilled person will be familiar with the general meaning of terms like UV absorber and UV protectant.

Preferred compounds to be used as UV absorber and/or visible light absorber or UV protectant include the following group of compounds:

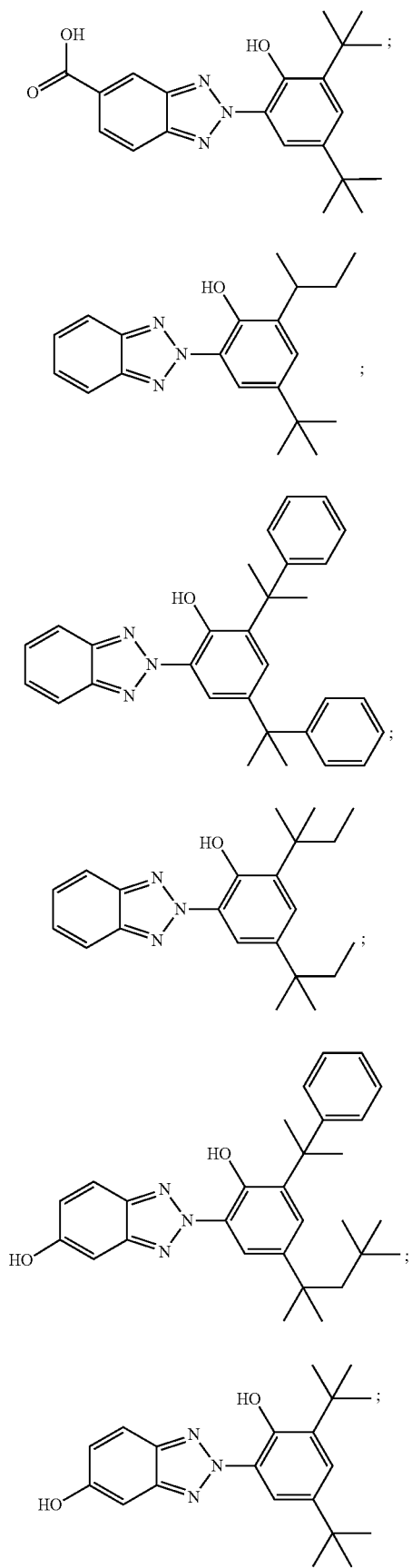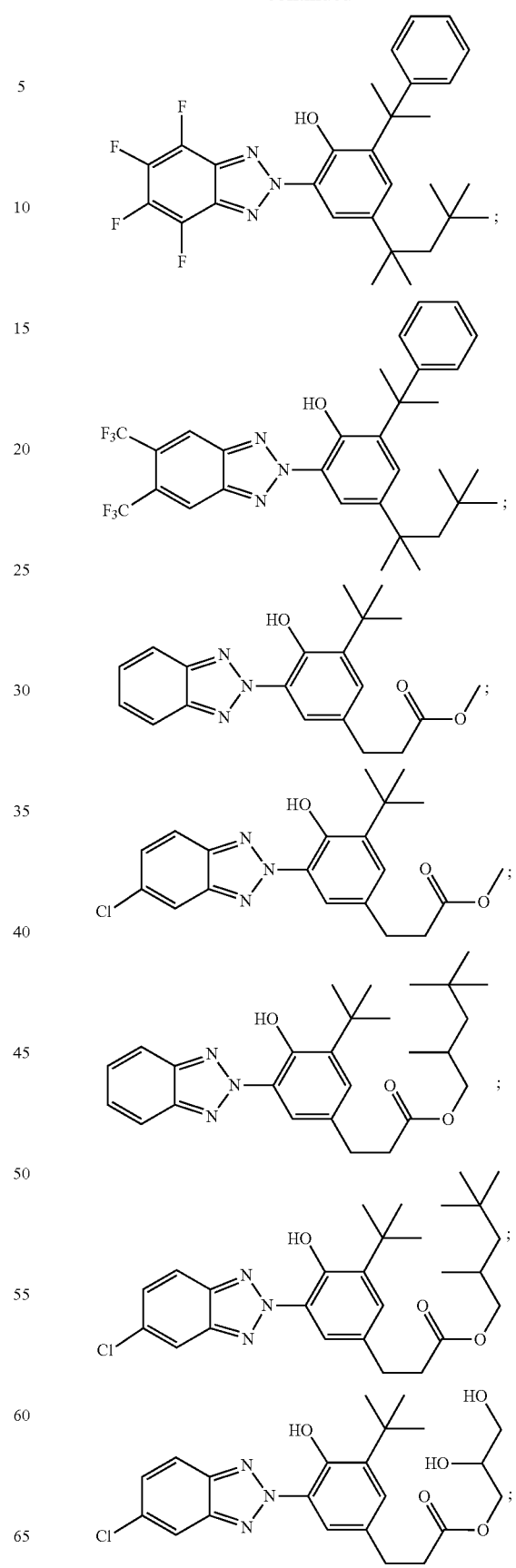

-continued
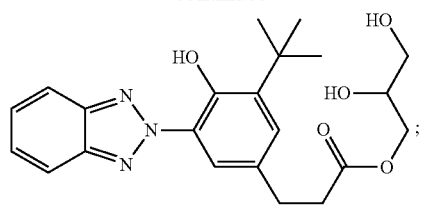
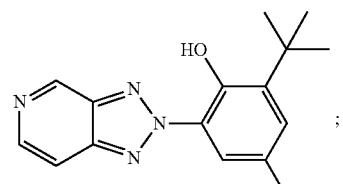
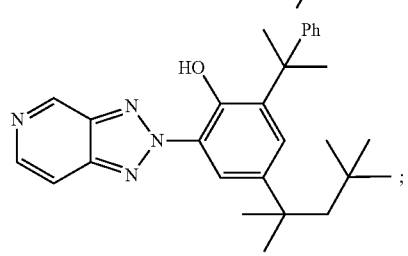
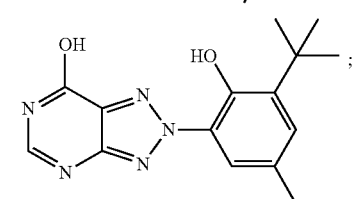
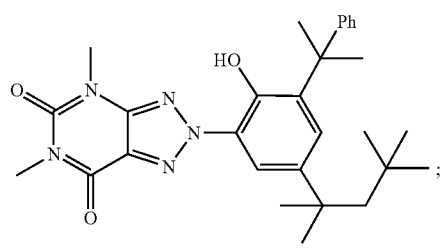
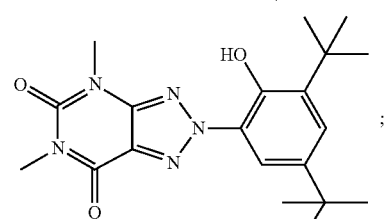
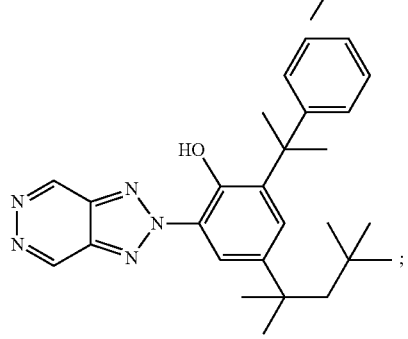
-continued
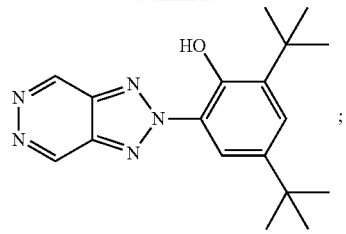
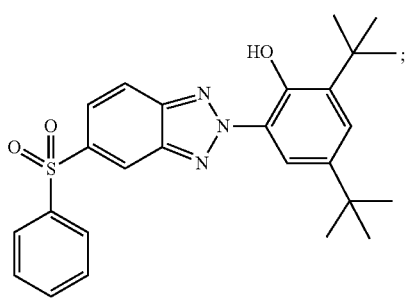
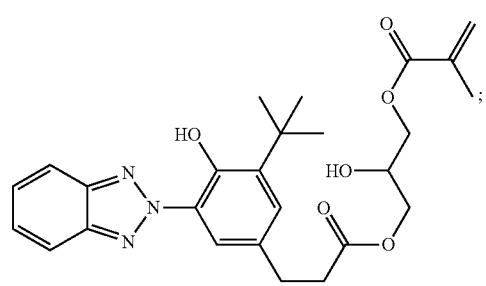
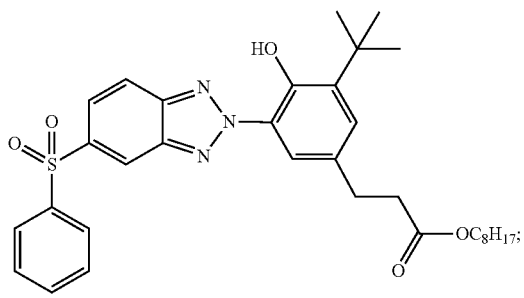
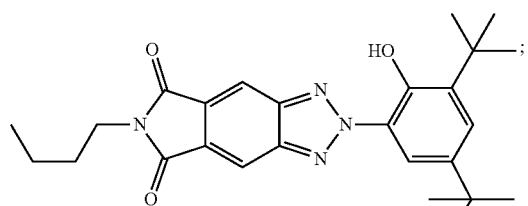
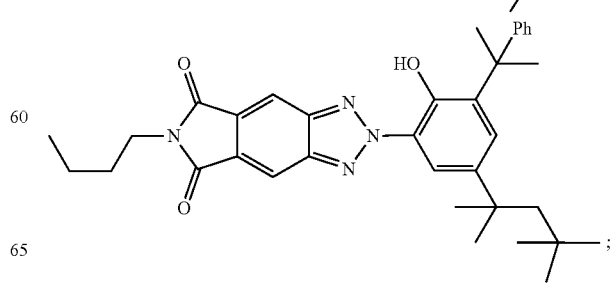

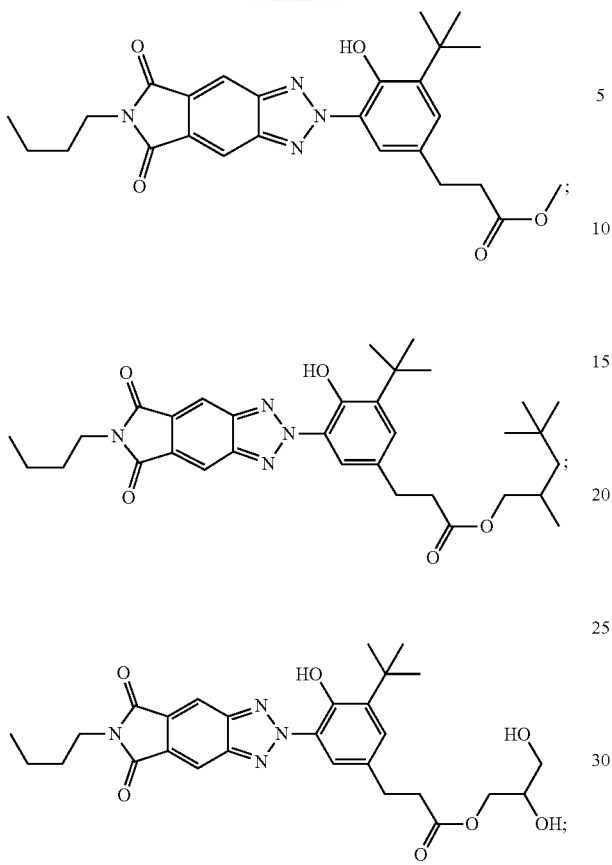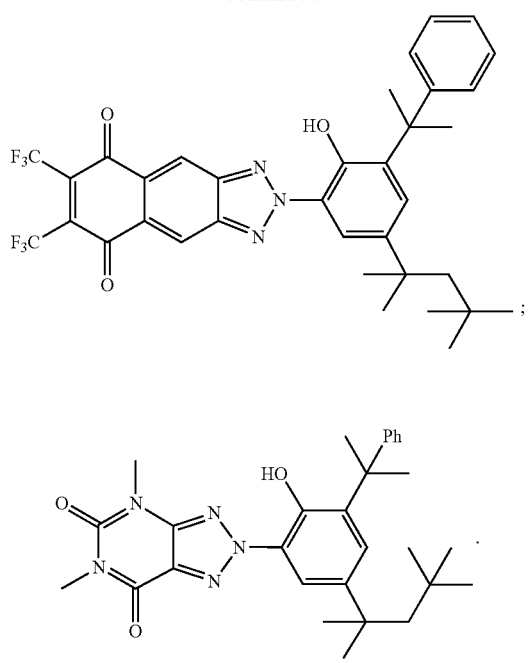
The present invention will be described in further detail by the examples provided below.
EXAMPLES
Preparative examples are given according the sequence outlined in scheme 4 for the claimed key steps II and III.
Example 1
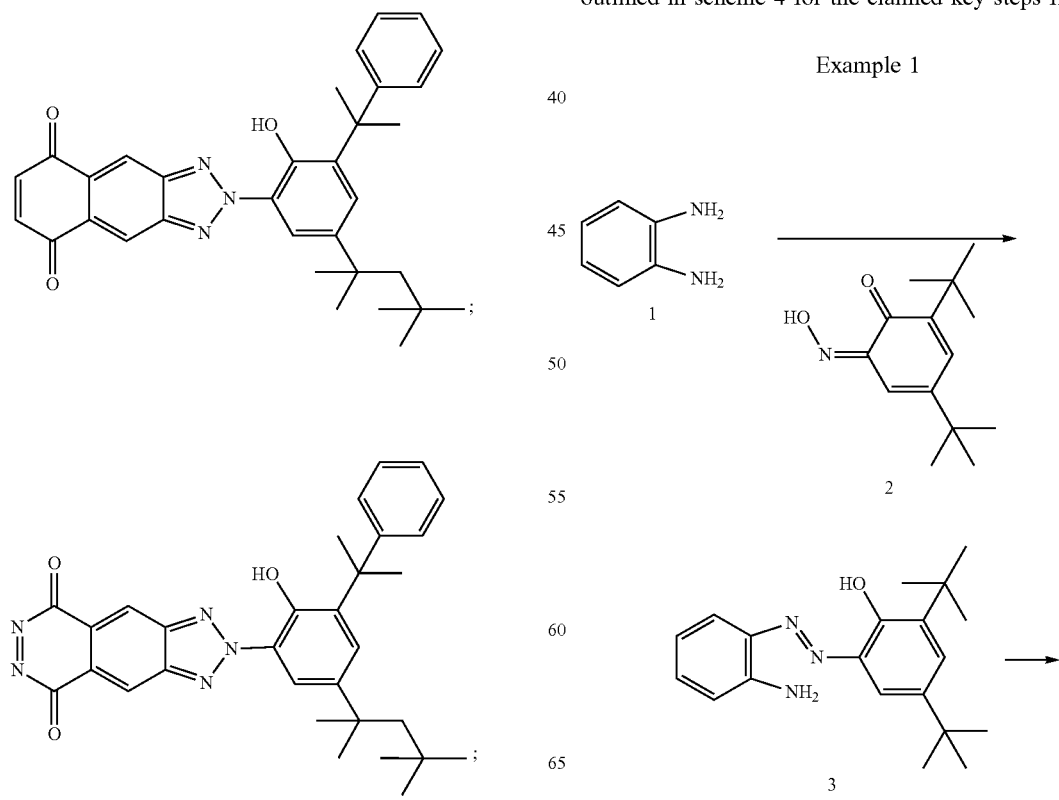

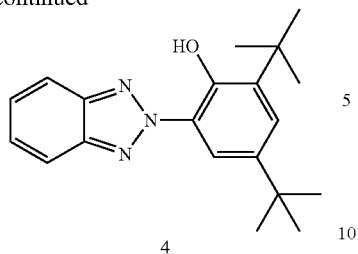

4

In a dry argon atmosphere 0.100 g of oxime 2, 0.075 g of 1,2-phenylene diamine 1 and 0.200 ml triethyl-borate (B(OEt)$_3$) are dissolved in 4 ml dry THF and heated for 24 h at 60° C. After a TLC shows consumption of starting oxime the mixture is evaporated to dryness and the resulting residue purified by column chromatography (eluent: hexane-ethyl acetate: 10-1 vol/vol) to give 0.132 g (96%) of the diazo-amine intermediate 3.

$^1$H-NMR (CDCl$_3$; 300.13 MHz) in ppm (internal TMS-referenced): 1.40 (s, 9H); 1.50 (s, 9H); 6.06 (s broad NH$_2$); 6.78 (dd, 1H); 6.85 (dt, 1H); 7.21 (dt, 1H); 7.41 (d, 1H); 7.63 (d, 1H); 7.72 (dd, 1H); 13.52 (s broad OH).

$^{13}$C-NMR (CDCl$_3$; 75.47 MHz) in ppm (internal TMS-referenced): 29.51; 31.49; 34.27; 35.29; 117.32; 117.58; 125.77; 127.00; 129.10; 131.49; 134.39; 136.46; 137.76; 141.20; 141.56; 149.88.

Comparative Example

Performing this reaction without the addition of B(OEt)$_3$ or performing the reactions in protic solvents, e.g. alcohols, results in the production of a series of side-products with only negligible amounts of compound 3. The TLC analysis of the coupling reaction of diamine 1 and oxime 2 is shown in FIG. 1. This TLC control further illustrates the critical role of the Lewis acid according to the present invention for the formation of the intermediate compound 3 according to general formula (III) (lane 1: crude product mixture obtained in the presence of B(OEt)$_3$; lane 2: product mixture with added reference compound 3; lanes 3 and 4: crude product mixture as obtained in the absence of B(OEt)$_3$; lane 5: starting oxime 2).

A mixture of 0.050 g of intermediate 3 and 0.190 g of CuSO$_4$, dissolved in 0.250 ml water is dissolved in 3.00 ml ethanol, containing 0.50 ml of 28% ammonia solution and heated to reflux in air until intermediate 3 is consumed. The mixture is then evaporated to dryness and taken up in ethyl acetate and subsequently extracted with EDTA-solution and brine and dried over sodium sulfate. Filtration and evaporation leaves a residue which is purified over silica gel (eluent: hexane-ethyl acetate: 10-0.5 vol/vol) giving 0.043 g (86%) of benzotriazole 4.

$^1$H-NMR (CDCl$_3$; 300.13 MHz) in ppm (internal TMS-referenced): 1.42 (s, 9H); 1.50 (s, 9H); 7.45 (d, 1H); 7.49 (m, 2H); 7.96 (m, 2H); 8.32 (d, 1H); 11.56 (broad s, OH).

$^{13}$C-NMR (CDCl$_3$; 75.47 MHz) in ppm (internal TMS-referenced): 29.72; 31.37; 34.60; 35.71; 116.19; 117.58; 125.11; 125.22; 127.42; 138.62; 141.68; 142.65; 146.74.

Example 2

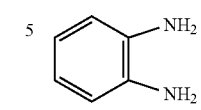

1

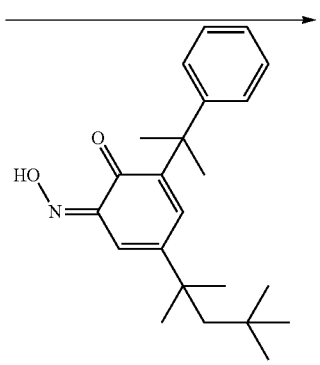

5

6

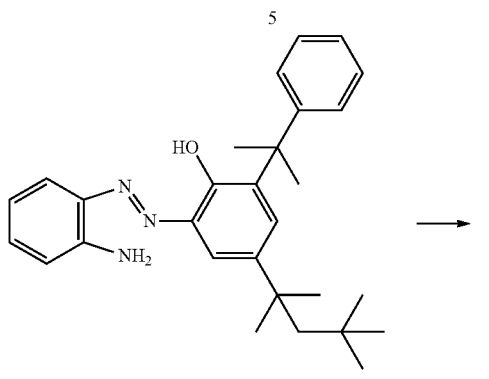

7

In a dry argon atmosphere 0.150 g of oxime 5, 0.070 g of 1,2-phenylene diamine 1 and 0.150 ml triethyl-borate are dissolved in 4 ml dry THF and heated for 24 h at 60° C. After a TLC shows consumption of starting oxime the mixture is evaporated to dryness and the resulting residue purified by column chromatography (eluent: hexane-ethyl acetate: 10-1 vol/vol) to give 0.171 g (92%) of the diazo-amine intermediate 6.

$^1$H-NMR (CDCl$_3$; 300.13 MHz) in ppm (internal TMS-referenced): 0.87 (s, 9H); 1.51 (s, 6H); 1.83 (s, 6H); 1.84 (s, 2H); 6.02 (broad s, NH$_2$); 6.73 (dd, 1H); 6.79 (dt, 1H); 7.17 (dt, 1H); 7.22 (m, 1H); 7.31 (m, 4H); 7.58 (d, 1H); 7.60 (dd, 1H); 7.68 (d, 1H); 13.00 (broad s OH).

$^{13}$C-NMR (CDCl$_3$; 75.47 MHz) in ppm (internal TMS-referenced): 29.05; 29.73; 31.81; 32.50; 38.15; 42.43; 56.92; 117.24; 117.47; 125.21; 125.63; 126.94; 125.92; 128.47; 129.37; 131.47; 134.37; 136.67; 136.81; 138.82; 141.47; 149.07; 150.65.

Replacing the B(OEt)₃ by 2.5 g of basic Al₂O₃ and the THF by 2 ml of xylene and heating this mixture to 140° C. for 48 h gives after the usual work-up 0.089 mg of diazo compound 6 and 0.300 g of starting oxime 5.

According the procedure given for the preparation of compound 4 in example 1, triazole 7 is obtained from 0.007 g (0.016 mmol) of intermediate amine 6 and 0.020 g (0.122 mmol) CuSO₄ in 100% (0.007 g). In this comparative example, 7.73 equivalents of copper salt are used.

¹H-NMR (CDCl₃; 300.13 MHz) in ppm (internal TMS-referenced): 0.88 (s, 9H); 1.57 (s, 6H); 1.89 (s, 6H); 1.91 (s, 2H); 7.23 (m, 1H); 7.34 (m, 4H); 7.45 (m, 2H); 7.68 (d, 2H); 7.88 (m, 2H); 8.41 (d, 1H); 11.49 (s broad 1H).

¹³C-NMR (CDCl₃; 75.47 MHz) in ppm (internal TMS-referenced): 29.79; 31.92; 32.00; 32.52; 38.49; 42.82; 57.01; 117.30; 117.51; 125.22; 125.32; 125.52; 126.53; 127.39; 127.94; 137.80; 140.40; 142.61; 146.06; 150.84.

More favorably, triazole 7 is obtained according the conditions listed in Table 1. As is has been observed, base-sensitive functional groups, e.g. cyclic amides or esters in various desired benzotriazole compounds, do not survive the conditions applied for the oxidative cyclization given in example 1 for the synthesis of the benzotriazole body without significant degradation.

TABLE 1

Yield for the ring closure reaction of the amine 6 to the benzotriazole compound 7 depending on the amount of catalyst

| run | Cu-salts | Conditions* | 7 [%] |
|---|---|---|---|
| 1 | 4.1 eq Cu(OAc)₂ | 2 ml pyr-5 ml THF, 70° C, mol sieves | 50 |
| 2 | 1.0 eq Cu(OAc)₂ | 2 ml pyr-5 ml THF, 70° C | 100 |
| 3 | 0.5 eq Cu(OAc)₂ | 2 ml pyr-5 ml THF, 70° C | 100 |
| 4** | 0.02 eq Cu(OAc)₂ | 2 ml pyr-10 ml THF, 70° C | 100 |
| 5 | 1.0 eq Cu(OAc)₂ | 5 eq TMEDA***- 5 ml THF, 70° C | 100 |
| 6 | 1.0 eq Cu(acac)₂ | 2.5 eq TMEDA***- 1 ml pyr-5 ml THF, 70° C, | 48 |
| 7 | 1.0 eq Cu(OAc)₂ | 5.0 eq MIA****- 5 ml THF, 70° C | 100 |

*0.050 g of amine 6 is used, refluxed until educt is consumed;
**0.200 g of amine 6 is reacted;
***N,N,N,N-tetramethylethylenediamine;
**** methylimidazole;

Example 3

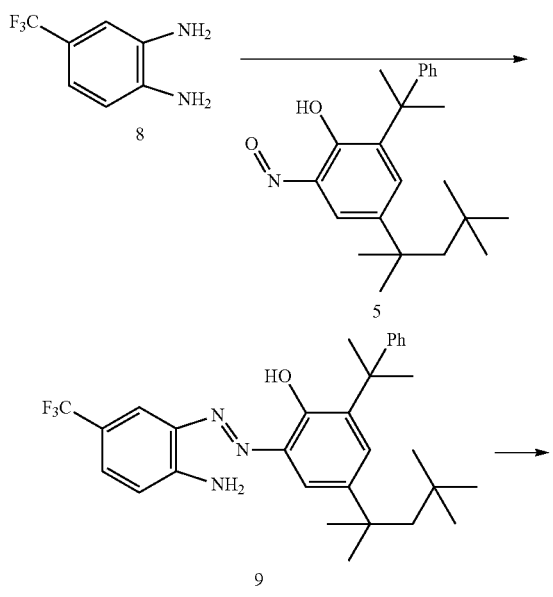

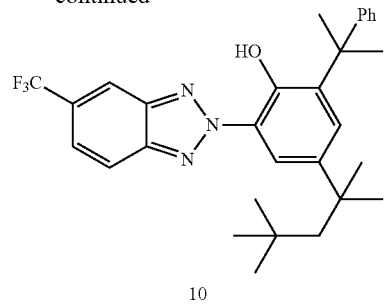

According to the procedure given for the preparation of compound 3 in example 1, diamine 8 (0.164 g) is treated with 0.328 g of oxime 5 and 0.300 ml B(OEt)₃ to yield 0.329 g (70%) of compound 9 as a mixture of two stereo isomers (78/22). The isomers are subsequently combined and cyclized in the following procedure.

¹H-NMR (CDCl₃; 300.13 MHz) in ppm (internal TMS-referenced): for main isomer: 0.85 (s, 9H); 1.50 (s, 6H); 1.84 (s, 6H); 1.87 (s, 2H); 5.56 (broad s, NH₂); 6.75 (d, 1H); 7.23 (m, 1H); 7.33 (m, 4H); 7.37 (dd, 1H); 7.66 (d, 1H); 7.69 (d, 1H); 7.87 d, 1H); 12.55 (broad OH).

¹³C-NMR (CDCl₃; 75.47 MHz) in ppm (internal TMS-referenced): for main isomer: 29.68; 31.83; 31.98; 32.50; 38.19; 42.44; 56.88; 117.44; 119.95; 122.10; 125.33; 125.58:127.00; 127.58; 128.00; 129.35; 133.90; 136.60; 137.10; 140.28; 143.15; 149.16; 150.48.

¹⁹F-NMR (CDCl3; 282.41 MHz): −61.44 main isomer; −63.14 minor isomer.

According to the procedure given in example 2 for the cyclization of compound 6 run 2, 0.300 g of azo-amine 9 (mixture of isomers) are cyclized to yield 0.270 g (91%) of benzotriazole 10.

¹H-NMR (CDCl₃; 300.13 MHz) in ppm (internal TMS-referenced): 0.83 (s, 9H); 1.46 (s, 6H); 1.84 (s, 6H); 1.88 (s, 2H); 7.21 (m, 1H); 7.30 (m, 4H); 7.64 (dd, 1H); 7.69 (d, 1H); 7.99 (d 1H); 8.25 (broad s, 1H); 8.37 (d, 1H); 11.13 (broad s, OH).

¹³C-NMR (CDCl₃; 75.47 MHz) in ppm (internal TMS-referenced): 29.71; 31.77; 31.96; 32.48; 28.48; 42.82; 56.93; 116.16; 117.46; 118.72; 121.99; 123.54; 125.05; 125.26; 125.47; 127.33; 127.93; 138.12; 140.77; 141.52; 143.02; 146.24; 150.60.

Example 4

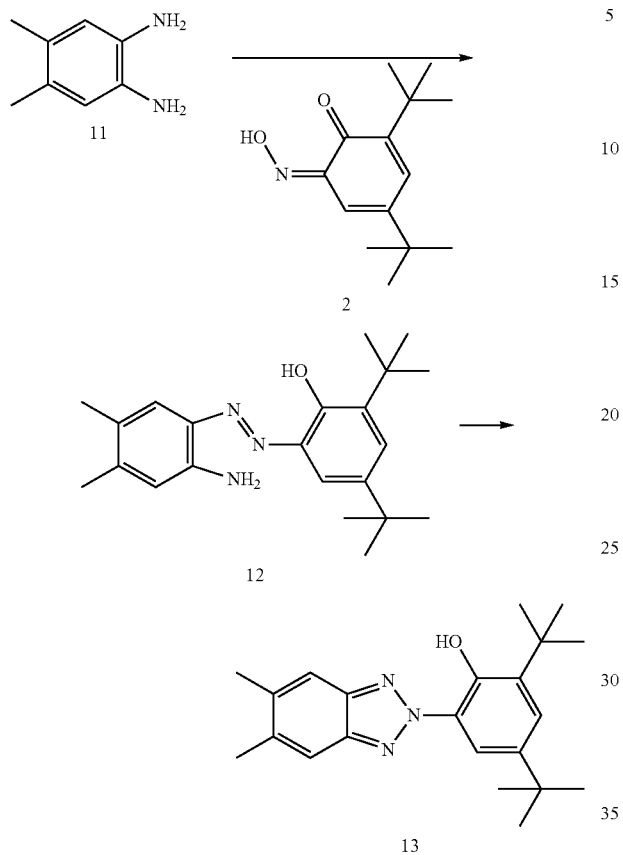

Example 5

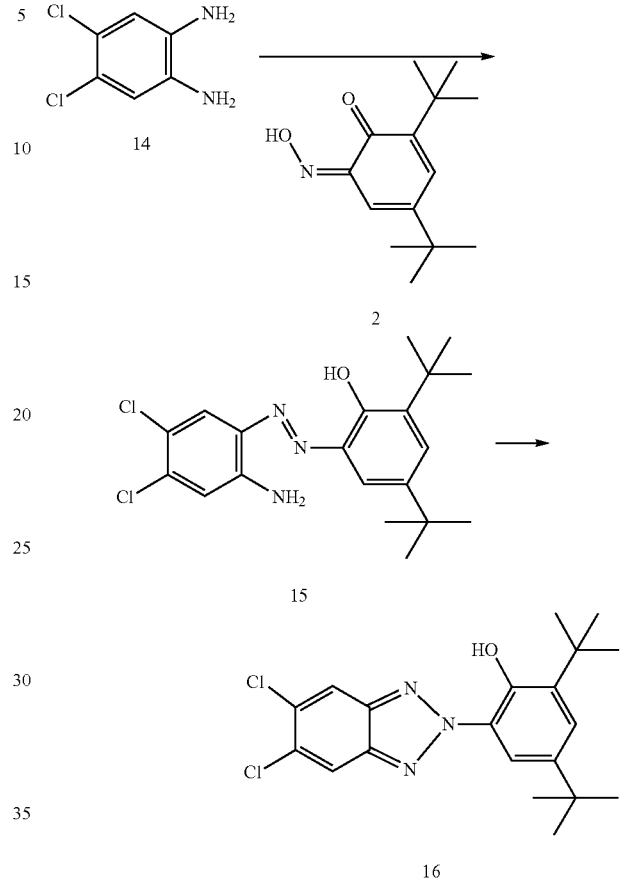

According to the procedure given for the preparation of compound 3 in example 1, diamine 11 (0.250 g) is treated with 0.430 g of oxime 2 and 0.620 ml B(OEt)$_3$ to yield 0.460 g (71%) of compound 12.

$^1$H-NMR (CDCl$_3$; 300.13 MHz) in ppm (internal TMS-referenced): 1.38 (s, 9H); 1.52 (s, 9H); 2.25 (s, 3H); 2.26 (s, 3H); 5.55 (broad, NH$_2$); 6.76 (s, 1H); 7.38 (d, 1H); 7.50 (s, 1H); 7.65 (d, 1H); 12.95 (broad OH).

$^{13}$C-NMR (CDCl$_3$; 75.47 MHz) in ppm (internal TMS-referenced): 18.71; 19.96; 29.51; 31.49; 34.28; 35.26; 119.53; 119.97; 125.29; 126.89; 127.96; 128.74; 133.99; 136.57; 137.59; 141.19; 141.43; 150.02.

According the procedure given in example 2 for the cyclization of compound 6 run 3, 0.460 g of azo-amine 12 are cyclized to yield 0.282 g (62%) of benzotriazole 13.

$^1$H-NMR (CDCl$_3$; 300.13 MHz) in ppm (internal TMS-referenced): 1.43 (s, 9H); 1.55 (s, 9H); 2.46 (s, 6H); 7.43 (d (1H); 7.68 (s, 2H); 8.29 (d, 1H); 11.14 (broad OH).

$^{13}$C-NMR (CDCl$_3$; 75.47 MHz) in ppm (internal TMS-referenced): 20.98; 29.61; 31.54; 34.58; 35.66; 115.93; 116.05; 124.57; 125.34; 138.10; 138.42; 141.52; 142.07; 146.48.

According the procedure given for the preparation of compound 3 in example 1, diamine 14 (0.250 g) is treated with 0.330 g of oxime 2 and 0.480 ml B(OEt)$_3$ to yield 0.420 g (76%) of compound 15.

$^1$H-NMR (CDCl$_3$; 300.13 MHz) in ppm (internal TMS-referenced): 1.39 (s, 9H); 1.44 (s, 9H); 4.90 (broad s, NH$_2$); 7.05 (broad d, 1H); 7.45 (d, 1H); 7.64 (d, 1H); 7.82 (s, 1H); 12.99 (broad s, OH).

$^{13}$C-NMR (CDCl$_3$; 75.47 MHz) in ppm (internal TMS-referenced): 29.44; 31.40; 34.31; 35.28; 119.35; 122.98; 125.35; 127.57 (2 C); 128.61 (2 C); 135.00; 136.75; 137.93; 141.81; 150.23.

According the procedure given in example 2 for the cyclization of compound 6 run 3, 0.390 g of azo-amine 15 are cyclized to yield 0.267 g (69%) of benzotriazole 16.

$^1$H-NMR (CDCl$_3$; 300.13 MHz) in ppm (internal TMS-referenced): 1.42 (s, 9H); 1.54 (s, 9H); 7.48 (d, 1H); 8.11 (s, 2H); 8.27 (d, 1H); 11.12 (OH).

$^{13}$C-NMR (CDCl$_3$; 75.47 MHz) in ppm (internal TMS-referenced): 29.56; 31.46; 34.61; 35.73; 116.24; 118.39; 124.92; 125.87; 132.40; 138.90; 141.51; 142.03; 146.78.

Example 6

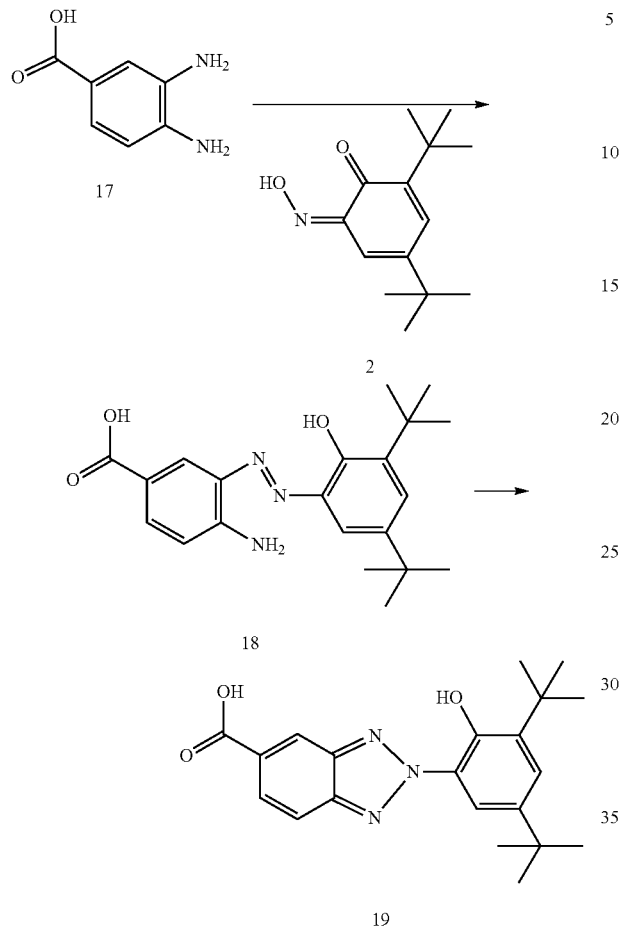

According to the procedure given for the preparation of compound 3 in example 1, diamine 17 (0.200 g) is treated with 0.310 g of oxime 2 and 0.440 ml B(OEt)₃ to yield 0.235 g (49%) of compound 18.

¹H-NMR (CDCl₃; 300.13 MHz) in ppm (internal TMS-referenced): 1.38 (s, 9H); 1.49 (s, 9H); 4.21 (broad NH₂); 6.83 (broad d, 1H); 7.46 (d, 1H); 7.65 (d, 1H); 7.88 (d, 1H); 8.44 (s, 1H); 12.97 (OH).

¹³C-NMR (CDCl₃—CD₃OD 75.47 MHz) in ppm (internal TMS-referenced): 33.28; 35.25; 38.10; 39.13; 120.72; 122.70; 129.34; 131.30; 136.49 (2 C); 136.82; 140.18; 141.70; 145.31; 149.43; 152.99; 172.69.

According the procedure given in example 2 for the cyclization of compound 6 run 3, 0.200 g of azo-amine 18 are cyclized to yield 0.125 g (63%) of benzotriazole 19.

¹H-NMR (CDCl₃—CD₃OD; 300.13 MHz) in ppm (internal TMS-referenced): 1.38 (s, 9H); 1.49 (s, 9H); 7.44 (d, 1H); 7.95 (d, 1H); 8.12 (d, 1H); 8.28 (d, 1H); 8.73 (d, 1H).

¹³C-NMR (CDCl₃—CD₃OD 75.47 MHz) in ppm (internal TMS-referenced): 29.48; 31.39; 34.54; 35.66; 116.29; 117.34; 121.31; 124.99; 125.74; 127.75; 129.66; 138.74; 141.94; 142.19; 144.51; 146.71; 168.12.

Example 7

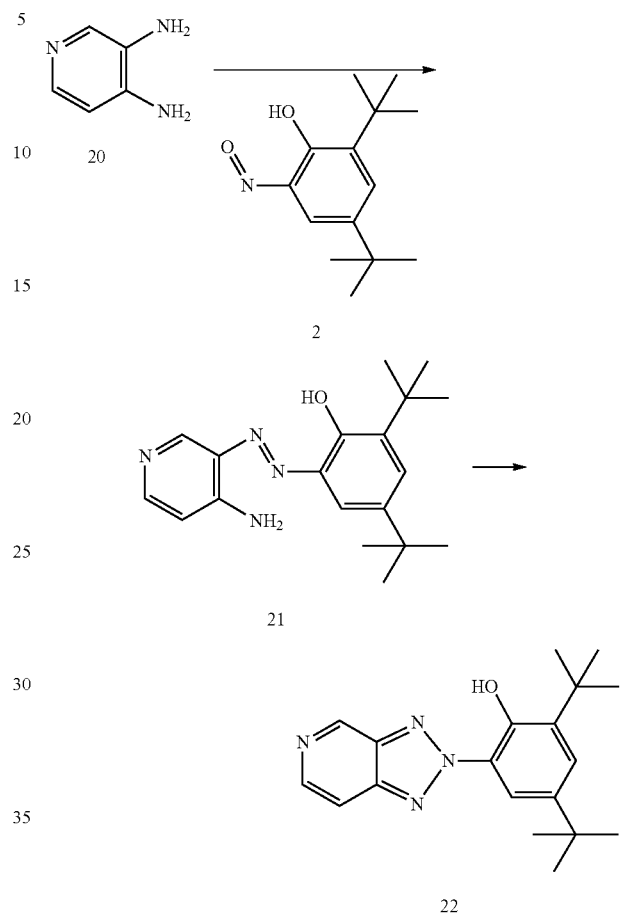

According to the procedure given for the preparation of compound 3 in example 1, diamine (0.690 g) is treated with 1.000 g of oxime 2 and 1.50 ml B(OEt)₃ to yield 1.100 g (80%) of compound 21.

¹H-NMR (CDCl₃; 300.13 MHz) in ppm (internal TMS-referenced): 1.39 (s, 9H); 1.50 (s, 9H); 6.66 (d, 1H); 6.93 (broad NH₂); 7.44 (d, 1H); 7.58 (d, 1H); 8.14 (broad d, 1H); 8.80 (s, 1H); 13.23 (OH).

¹³C-NMR (CDCl₃; 75.47 MHz) in ppm (internal TMS-referenced): 29.48; 31.45; 34.26; 35.34; 111.57; 126.09; 127.82; 131.02; 136.35; 138.13; 141.49; 146.06; 149.31; 149.76; 152.73.

According the procedure given in example 2 for the cyclization of compound 6 run 1—but refluxed for only 7 h—0.110 g of azo-amine 21 are cyclized to yield 0.100 g (92%) of benzotriazole 22.

¹H-NMR (CDCl₃; 300.13 MHz) in ppm (internal TMS-referenced): 1.42 (s, 9H); 1.54 (s, 9H); 7.52 (d, 1H); 7.82 (d, 1H); 8.33 (d, 1H); 8.57 (broad 1H); 9.57 (broad 1H); 11.41 (OH).

¹³C-NMR (CDCl₃; 75.47 MHz) in ppm (internal TMS-referenced): 29.56; 31.45; 34.61; 35.76; 111.02; 116.61; 124.86; 126.48; 139.08; 142.15; 143.41; 144.29 (2 C); 144.83; 147.26.

Example 8

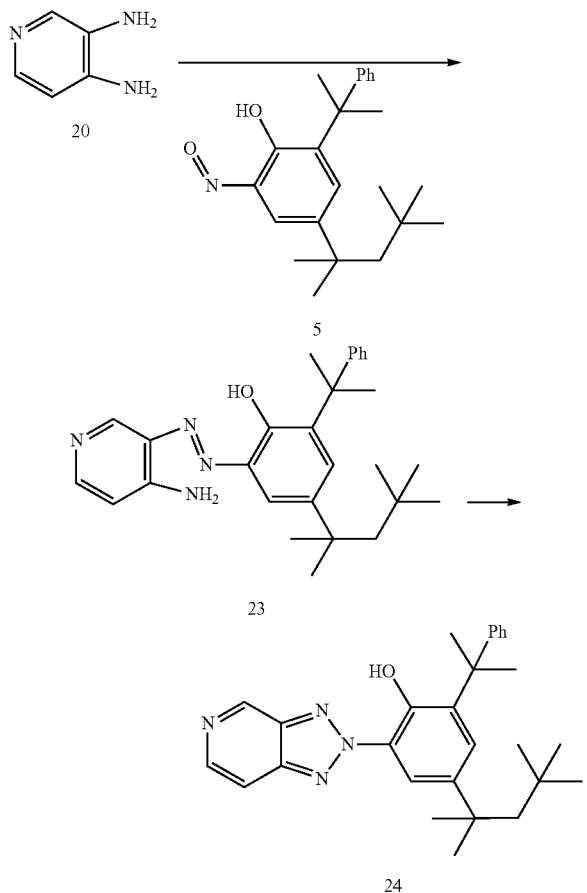

According the procedure given for the preparation of compound 3 in example 1, diamine 20 (0.070 g) is treated with 0.150 g of oxime 5 and 0.150 ml B(OEt)$_3$ to yield 0.150 g (83%) of compound 23.

$^1$H-NMR (CDCl$_3$; 300.13 MHz) in ppm (internal TMS-referenced): 0.83 (s 9H); 1.48 (s, 6H); 1.79 (s, 6H); 1.82 (s, 2H); 6.58 (d, 1H); 6.79 (NH$_2$); 7.19 (m, 1H); 7.28 (m, 4H); 7.60 (s 2H); 8.08 (d, 1H); 8.67 (s, 1H); 12.69 (OH).

$^{13}$C-NMR (CDCl$_3$; 75.47 MHz) in ppm (internal TMS-referenced): 29.64; 31.74; 31.94; 32.46; 38.12; 42.41; 56.84; 111.42; 125.28; 125.55; 127.15; 127.93; 129.17; 136.55; 137.18; 140.11; 145.84; 148.91 (2 C); 149.45; 150.38; 152.95.

According the procedure given in example 2 for the cyclization of compound 6 run 2, 0.100 g of azo-amine 23 are cyclized to yield 0.077 g (77%) of benzotriazole 24.

$^1$H-NMR (CDCl$_3$; 300.13 MHz) in ppm (internal TMS-referenced): 0.86 (s, 9H); 1.55 (s, 6H); 1.83 (s, 6H); 1.89 (s, 2H); 7.20 (m, 1H); 7.30 (m, 4H); 7.73 (d, 1H); 7.79 (broad d, 1H); 8.40 (d, 1H); 8.55 (broad s, 1H); 9.53 (broad s, 1H); 11.09 (OH).

$^{13}$C-NMR (CDCl$_3$; 75.47 MHz) in ppm (internal TMS-referenced): 29.71; 31.77; 31.89; 32.50; 38.51; 42.84; 56.92; 111.05; 117.73; 124.95; 125.32; 125.46; 127.92; 127.97; 138.34; 140.98; 143.09; 144.08 (2 C); 144.89; 146.62; 150.47.

Example 9

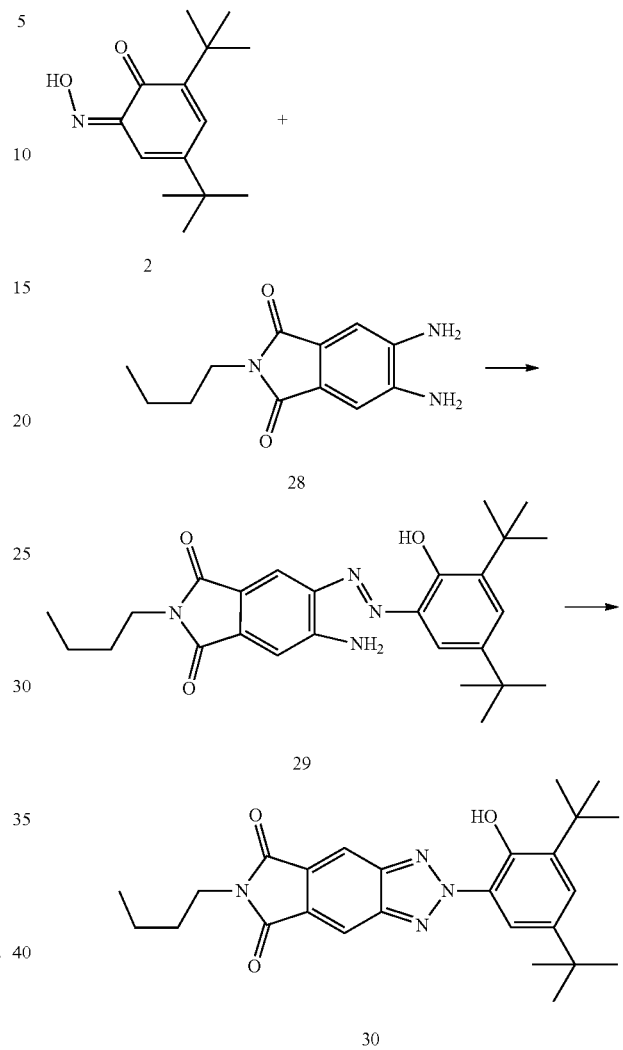

According to the procedure given for the preparation of compound 3 in example 1, diamine 28 (0.100 g) is treated with 0.090 g of oxime 2 and 0.150 ml B(OEt)$_3$ to yield 0.128 g (73%) of compound 29.

$^1$H-NMR (CDCl$_3$; 300.13 MHz) in ppm (internal TMS-referenced): 0.98 (t, 3H); 1.33 (m, 2H); 1.39 (s, 9H); 1.49 (s, 9H); 1.74 (m, 2H); 3.69 (t, 2H); 6.77 (NH$_2$); 7.25 (s, 1H); 7.48 (d, 1H); 7.63 (d, 1H); 8.17 (s, 1H); 12.99 (OH).

$^{13}$C-NMR (CDCl$_3$; 75.47 MHz) in ppm (internal TMS-referenced): 13.65; 20.12; 29.43; 31.38; 31.88; 34.30; 35.34; 37.95; 111.97; 120.04; 123.56; 125.57; 128.78; 134.19; 135.92; 136.65; 138.21; 141.87; 146.69; 150.31; 167.83; 167.86.

According to the procedure given in example 2 for the cyclization of compound 6 run 3, 0.120 g of azo-amine 29 are cyclized to yield 0.101 g (85%) of benzotriazole 30.

$^1$H-NMR (CDCl$_3$; 300.13 MHz) in ppm (internal TMS-referenced): 1.22 (t, 3H); 1.38 (m, 11H); 1.50 (s, 9H); 1.65 (m, 2H); 3.80 (t, 2H); 7.52 (d, 1H); 8.34 (d, 1H); 8.46 (s, 2H); 11.75 (OH).

$^{13}$C-NMR (CDCl$_3$; 75.47 MHz) in ppm (internal TMS-referenced): 13.84; 20.14; 29.55; 30.52; 31.44; 34.65; 35.77;

38.37; 114.71; 116.41; 124.86; 126.57; 130.11; 139.16; 142.31; 144.71; 147.00; 167.09.

Example 10

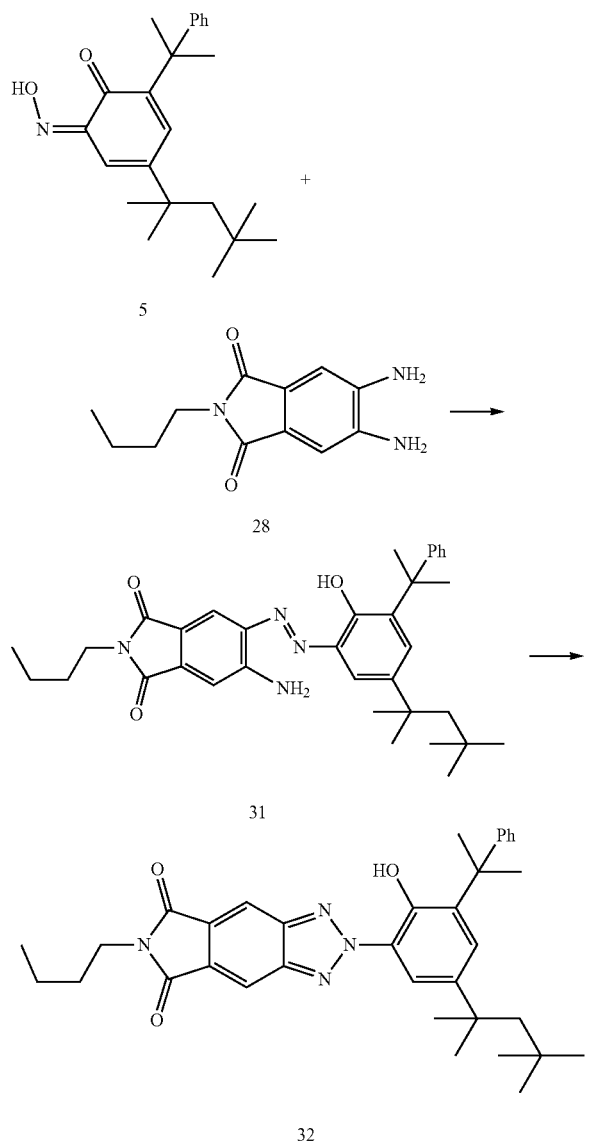

According to the procedure given for the preparation of compound 3 in example 1, diamine 28 (0.145 g) is treated with 0.200 g of oxime 5 and 0.215 ml B(OEt)$_3$ to yield 0.195 g (61%) of compound 31.

$^1$H-NMR (CDCl$_3$; 300.13 MHz) in ppm (internal TMS-referenced): 0.85 (s, 9H); 0.95 (t, 3H); 1.41 (m, 2H); 1.52 (s, 6H); 1.63 (m, 2H); 1.82 (s, 6H); 1.84 (s, 2H); 3.67 (t, 2H); 6.76 (NH$_2$); 7.18 (m, 2H); 7.25 (m, 4H); 7.66 (m, 2H); 8.04 (s, 1H); 12.50 (OH).

$^{13}$C-NMR (CDCl$_3$; 75.47 MHz) in ppm (internal TMS-referenced): 13.68; 20.14; 29.04; 29.73; 31.91; 31.98; 32.49; 37.93; 38.18; 42.40; 56.80; 112.00; 119.78; 123.63; 125.36; 125.63; 126.85; 127.97; 130.05; 134.14; 135.77; 136.86; 137.34; 140.53; 146.74; 149.44; 150.25; 167.72; 167.91.

According the procedure given in example 2 for the cyclization of compound 6 run 3, 0.150 g of azo-amine 31 are cyclized to yield 0.125 g (83%) of benzotriazole 32.

$^1$H-NMR (CDCl$_3$; 300.13 MHz) in ppm (internal TMS-referenced): 0.88 (s, 9H); 0.99 (t, 3H); 1.44 (m, 2H); 1.54 (s, 6H); 1.75 (m, 2H); 1.84 (s, 6H); 1.89 (s, 2H); 3.78 (t, 2H); 7.20 (m, 1H); 7.29 (m, 4H); 7.72 (d, 1H); 8.37 (m, 3H); 11.00 (OH).

$^{13}$C-NMR (CDCl$_3$; 75.47 MHz) in ppm (internal TMS-referenced): 13.64; 20.14; 29.71; 30.52; 31.77; 32.50; 32.72; 38.36; 38.52; 42.48; 56.90; 114.63; 117.50; 124.94; 125.34; 125.43; 127.90; 127.98; 130.07; 138.32; 141.09; 144.67; 146.38; 150.45; 167.06.

Example 11

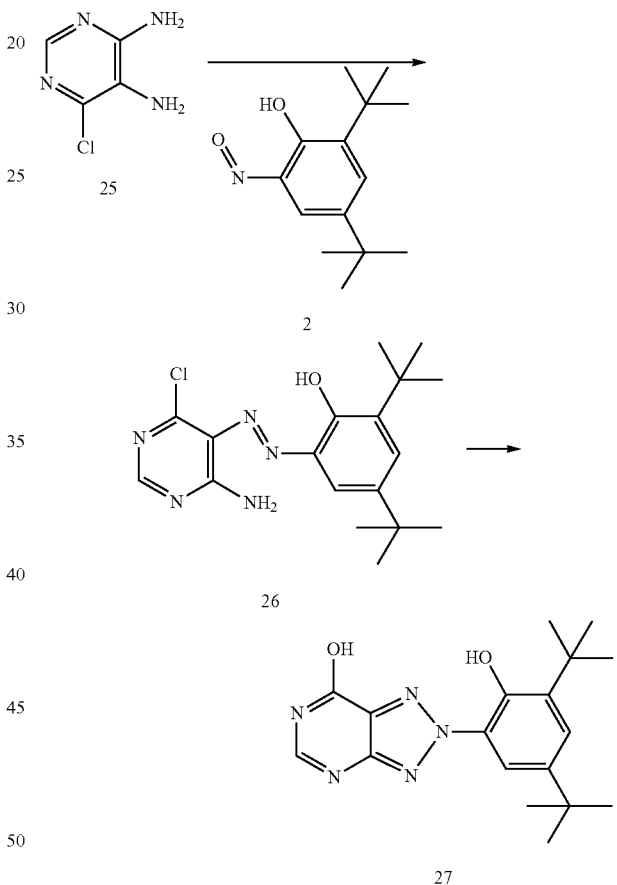

According to the procedure given for the preparation of compound 3 in example 1, diamine 25 (0.200 g) are treated with 0.320 g of oxime 2 and 0.470 ml B(OEt)$_3$ to yield 0.040 g (11%) of compound 26.

$^1$H-NMR (CDCl$_3$; 300.13 MHz) in ppm (internal TMS-referenced): 1.40 (s, 9H); 1.50 (s, 9H); 6.50 (NH); 7.51 (d, 1H); 7.59 (d, 1H); 9.27 (NH); 13.19 (OH).

$^{13}$C-NMR (CDCl$_3$; 75.47 MHz) in ppm (internal TMS-referenced): 29.49; 31.36; 34.29; 35.44; 123.23; 126.76; 129.44; 136.04; 138.70; 141.89; 149.91; 155.01; 157.05; 160.55.

According the procedure given in example 2 for the cyclization of compound 6 run 2, 0.0.40 g of azo-amine 26 are cyclized to yield 0.038 g (95%) of benzotriazole 27.

¹H-NMR (CDCl₃; 300.13 MHz) in ppm (internal TMS-referenced): 1.39 (s, 9H); 1.51 (s, 9H); 7.50 (broad, 1H); 8.23 (broad 2H); 10.79 (OH).

Example 12

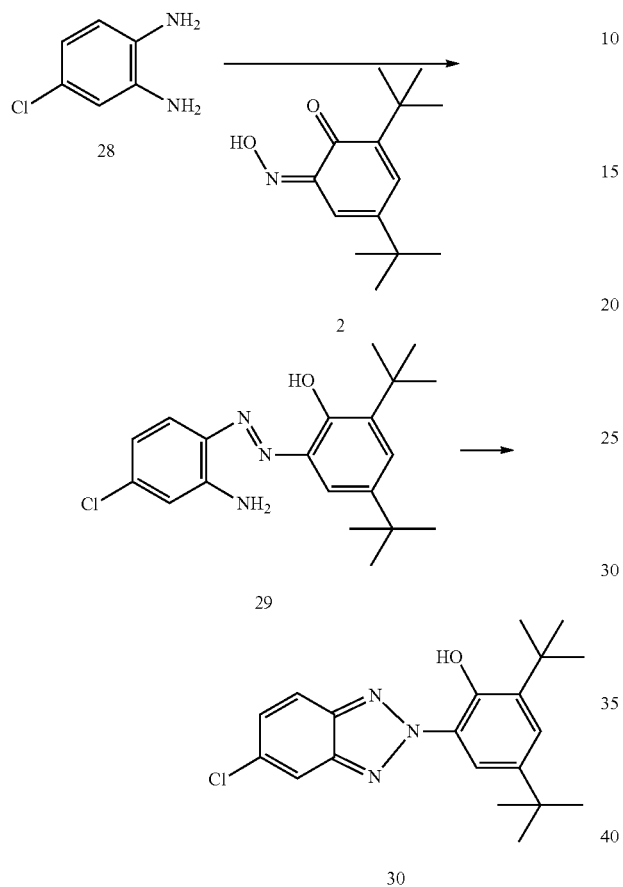

According to the procedure given for the preparation of compound 3 in example 1, diamine 28 (1.500 g) is treated with 2.500 g of oxime 2 and 3.75 ml B(OEt)₃ to yield 2.97 g (80%) of compound 29 as a mixture of isomers (ratio: 61-39).

¹H-NMR (CDCl₃; 300.13 MHz) in ppm (internal TMS-referenced): 1.41 (s, 9H); 1.50 (s, 9H); 6.16 (broad s, NH₂); 6.77 (d, 1H); 6.80 (dd, 1H); 7.42 (d, 1H); 7.57 (d, 1H); 7.61 (dd, 1H); 13.52 (broad s, OH). Main isomer only.

¹³C-NMR (CDCl₃; 75.47 MHz) in ppm (internal TMS-referenced): 29.49; 31.46; 34.27; 35.30; 116.60; 117.95; 125.70; 127.36; 130.36; 132.96; 136.39; 137.15; 137.96; 141.39; 142.31; 149.85.
Main Isomer Only According the procedure given in example 2 for the cyclization of compound 6 run 3, 2.00 g of the isomeric mixture of azo-amine 29 as obtained above is cyclized to yield 1.50 g (76%) of benzotriazole 30.

¹H-NMR (CDCl₃; 300.13 MHz) in ppm (internal TMS-referenced): 1.42 (s, 9H); 1.54 (s, 9H); 7.44 (dd, 1H); 7.48 (d, 1H); 7.90 (d, 1H); 7.96 (d, 1H); 8.29 (d, 1H); 11.55 (broad s, OH).

¹³C-NMR (CDCl₃; 75.47 MHz) in ppm (internal TMS-referenced): 29.57; 31.49; 34.59; 35.71; 116.18; 116.63; 118.76; 125.05; 125.50; 128.99; 133.33; 138.76; 141.17; 141.87; 143.01; 146.17.

Example 13

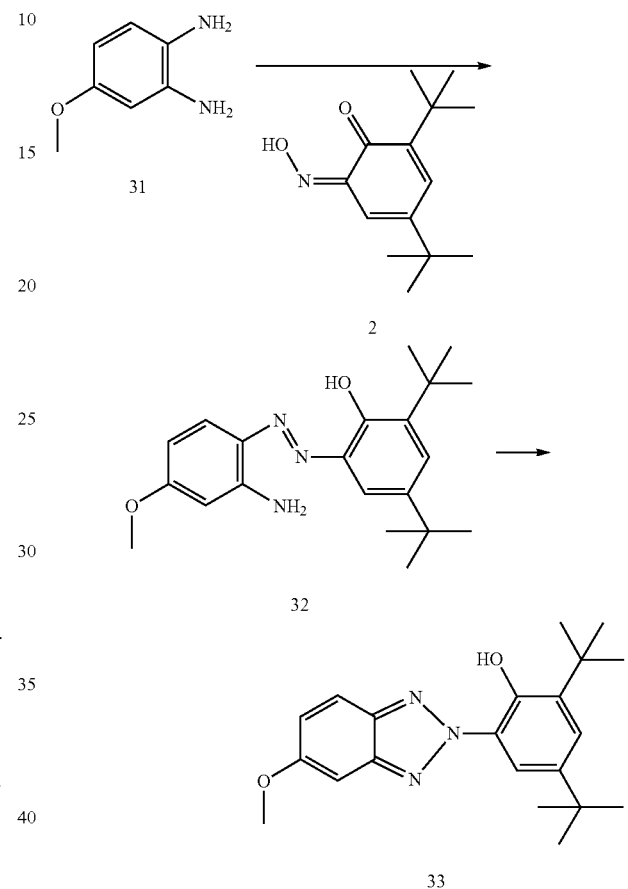

According to the procedure given for the preparation of compound 3 in example 1, diamine 31 as the dihydrogen chloride salt (3.00 g) is treated with 3.30 g of oxime 2 and 4.82 ml B(OEt)₃ to yield 4.20 g (84%) of compound 32 as a mixture of isomers (ratio: 85-15).

¹H-NMR (CDCl₃; 300.13 MHz) in ppm (internal TMS-referenced): 1.40 (s, 9H); 1.51 (s, 9H); 3.86 (s, 3H); 6.21 (d, 1H); 6.32 (broad s, NH₂); 6.45 (dd, 1H); 7.37 (d, 1H); 7.95 (d, 1H); 7.627 (d, 1H); 13.48 (broad s, OH). Main isomer only.

¹³C-NMR (CDCl₃; 75.47 MHz) in ppm (internal TMS-referenced): 29.55; 31.53; 34.26; 35.26; 55.40; 100.04; 105.58; 125.13; 125.95; 129.46; 131.75; 136.26; 137.54; 141.01; 143.50; 149.63; 162.36. Main isomer only According the procedure given in example 2 for the cyclization of compound 6 run 3, 2.70 g of the isomeric mixture of azo-amine 32 as obtained above is cyclized to yield 2.50 g (91%) of benzotriazole 33.

¹H-NMR (CDCl₃; 300.13 MHz) in ppm (internal TMS-referenced): 1.43 (s, 9H); 1.55 (s, 9H); 3.94 (s, 3H); 7.17 (m, 2H); 7.43 (d, 1H); 7.82 (d, 1H); 8.26 (d, 1H); 11.55 (broad s, OH).

$^{13}$C-NMR (CDCl$_3$; 75.47 MHz) in ppm (internal TMS-referenced): 29.60; 31.54; 34.57; 35.67; 55.62; 94.29; 115.80; 118.39; 122.47; 124.54; 125.33; 138.46; 141.48; 143.72; 146.31; 159.59.

Preparation of Starting Oximes 2 and 5:

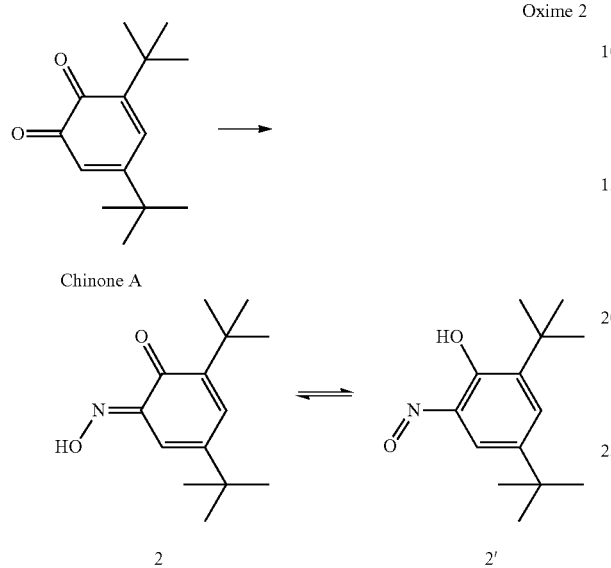

The nitroso-compound 2' which is in a tautomeric equilibrium with the more stable oxime 2 is best obtained from commercial chinone A (V. T. Kasumov et al., Spectrochimica Acta A, 2000, 56, 841: not isolated and no yield given).

In an argon atmosphere, 20.00 g of the ortho-chinone A are dissolved in 450 ml/so-propanol and 24 ml of pyridine. After addition of 6.40 g of hydroxylamine hydrochloride salt, the mixture is heated to reflux for 3 h, cooled down, diluted with diethyl ether and subsequently extracted with 0.5 N hydrochloric acid, sat. hydrogen carbonate solution and brine. The organic phase is dried over sodium sulfate, filtered and evaporated giving 21.90 g (96%) of compound 2/2'. The crude material—without crystallization (96%)—was also conveniently used without significant adverse effects. Due to the tautomeric equilibrium the spectra are not well resolved.

$^1$H-NMR (CDCl$_3$; 300.13 MHz) in ppm (internal TMS-referenced): 1.35 (s, 9H); 1.40 (s, 9H); 5.52 (broad, 1H); 7.80 (broad, 1H).

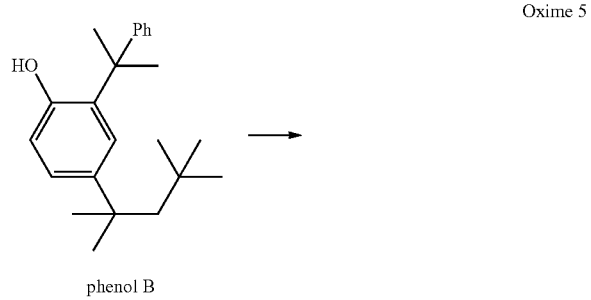

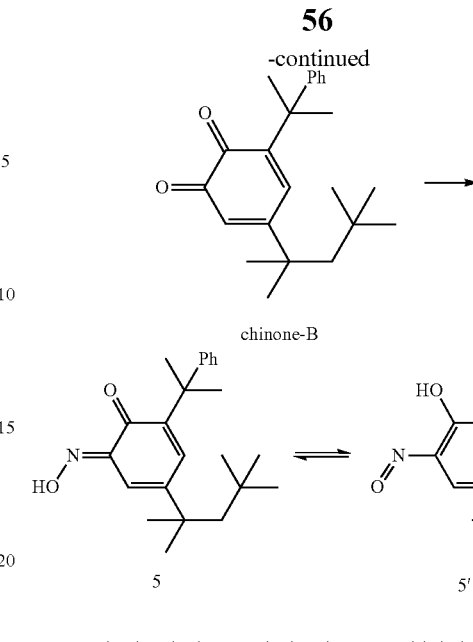

We obtained nitroso derivative 5', which is also in equilibrium with its oxime taumer 5 by the two-step process depicted above, as the ortho-chinone B is currently not available on large scale, commercially, whereas phenol B is produced on a large ton scale.

According a published ortho-oxidation protocol for phenols (M. Uyanik et al. Molecules 2012, 17, 8604 or US2017/0066711) which claims to give directly the ortho-chinone products, 15.8 g of phenol B precursor are dissolved in 200 ml ethyl acetate. This solution is added to a clear—usually stirred for 24 h at room temperature—solution containing 30 g of commercial Oxone®, 6.7 g of potassium carbonate, 72 g of sodium sulfate, 1.6 g of phase transfer catalyst tetra n-butyl ammonium hydrogen sulfate and 0.84 g of active oxidative catalyst sodium 2-iodo-benzenesulfonate in 150 ml ethyl acetate. The reaction mixture is then vigorously stirred at room temperature until all starting phenol is consumed, filtered and extracted with water and brine. Evaporation of solvent gives a residue which is purified over silica gel (eluent: hexane-ethyl acetate 10-2) to yield 10.0 g (61%) of pure novel chinone B as a colorless syrupy mass.

$^1$H-NMR (CDCl$_3$; 300.13 MHz) in ppm (internal TMS-referenced): 0.98 (s, 9H); 1.28 (s, 6H); 1.65 (s, 6H); 1.72 (s, 2H); 6.31 (d, 1H); 7.00 (d, 1H); 7.26 (m, 5H).

$^{13}$C-NMR (CDCl$_3$; 75.47 MHz) in ppm (internal TMS-referenced): 28.55; 28.99; 31.57; 32.56; 40.31; 42.35; 53.23; 123.66; 125.67; 126.18; 128.38; 135.20; 147.19; 148.27; 163.53; 179.58; 180.16.

10.0 g of the chinone B are treated with 2.3 g of hydroxyl amine hydrochloride as described for the oxime 2 to give after work-up 8.8 g (85%) of syrupy chinoxime 5/5'.

$^1$H-NMR (CDCl$_3$; 300.13 MHz) in ppm (internal TMS-referenced): 0.91 (s, 9H); 1.44 (s, 6H); 1.73 (s, 6H); 1.78 (s, 2H); 7.17-7.32 (m, 5H); 7.67 (broad d, 1H); 7.77 (broad, 1H).

Starting Ortho-Diamino-Phthalimide 28:

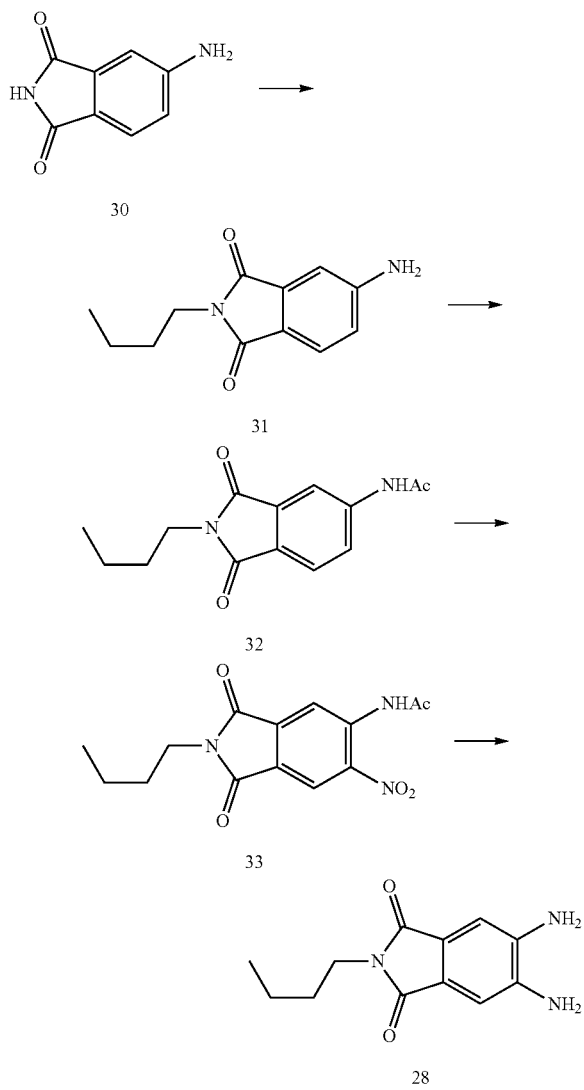

Commercial amino phthalimide 30 is first alkylated according a published protocol (U.S. Pat. No. 3,980,634). 2.50 g of Amino-phthalimide 30 are dissolved in 25 ml of dry dimethylformamide containing 4.25 g of butyl iodide and 0.075 g of 18-crown-6 ether at room temperature. This mixture is then treated portion-wise with 4.45 g of potassium carbonate with vigorous stirring and stirred until all starting compound is consumed. The mixture is filtered, diluted with ethyl acetate and subsequently extracted with water and brine. Evaporation of organic solvent leaves 3.28 g (97%) of the butyl phthalimide 31 which is sufficiently pure for the next step.

$^1$H-NMR (CDCl$_3$; 300.13 MHz) in ppm (internal TMS-referenced): 0.92 (t, 3H); 1.33 (m, 2H); 1.62 (m, 2H); 3.62 (t, 2H); 6.81 (dd, 1H); 7.01 (d, 1H); 7.57 b (d, 1H).

$^{13}$C-NMR (CDCl$_3$; 75.47 MHz) in ppm (internal TMS-referenced): 13.64; 20.07; 30.74; 37.56; 108.43; 117.75; 120.57; 124.92; 134.96; 152.33; 168.69; 168.79.

The amine 31 is intermittently acylated to amide 32 to ensure clean ortho-nitration to compound 33.

3.00 g of intermediate 31 are dissolved at room temperature in a mixture of 20 ml dichloromethane, 3.00 ml acetic anhydride and 4.00 ml of pyridine and stirred at room temperature until the starting amine 31 is consumed. The mixture is then diluted with ethyl acetate and extracted with 1 N hydrogen chloride solution, sat. sodium hydrogen carbonate solution and brine. Evaporation of solvent gives 3.50 g (100%) of the amide 32 as a yellow powder sufficiently pure for the next step.

$^1$H-NMR (CDCl$_3$; 300.13 MHz) in ppm (internal TMS-referenced): 0.90 (t, 3H); 1.29 (m, 2H); 1.60 (m, 2H); 2.19 (s, 3H); 3.64 (broad NH); 3.61 (t, 2H); 7.70 (d, 1H); 7.95 (dd, 1H); 7.98 (s (1H).

$^{13}$C-NMR (CDCl$_3$; 75.47 MHz) in ppm (internal TMS-referenced): 20.02; 22.09; 24.31; 30.50; 37.81; 113.88; 123.65; 124.22; 126.33; 133.43; 144.05; 168.20; 168.42; 169.72.

The N-acetylated phthalimide 32 is subsequently nitrated according published procedures (O. V. Shishkina et al. Rus. J. Gen. Chem. 1997, 67(5), 789). 10.0 g of the acetylated amide 32 are mixed at −10° C. into 15 ml of conc. sulfuric acid (d 1.84) with vigorous stirring. To this mixture are then added dropwise 4.8 ml of conc. nitric acid (d 1.51) and it is further stirred below −5° C. until the starting material is consumed. The mixture is then poured cautiously onto a mixture of ice/ethyl acetate and sodium hydrogen carbonate with vigorous stirring and pH adjusted to 8 by the addition of more sodium hydrogen carbonate. The organic phase is separated and evaporated. The residue is further purified by column chromatography on silica gel (eluent dichloromethane-ethyl acetate 20-1) to give 7.6 g (65%) nitro amide 33.

$^1$H-NMR (CDCl$_3$; 300.13 MHz) in ppm (internal TMS-referenced): 0.95 (t, 3H); 1.36 (m, 2H); 1.67 (m, 2H); 2.38 (s, 3H); 3.72 (t, 2H); 8.65 (s, 1H); 9.29 (s, 1H); 10.61 (NH).

$^{13}$C-NMR (acetone-D$_6$; 75.47 MHz) in ppm (internal TMS-referenced): 13.02; 19.77; 24.20; 30.22; 37.91; 116.90; 120.50; 125.60; 136.75; 139.06; 140.58; 165.76; 166.09; 169.29.

According a published procedure (A. R. Katrizky et al. J. Heterocycl. Chem. 1992, 29, 1519) 8.9 g of the nitro-amide 33 are dissolved in 100 ml acetone and 10 ml water at 40° C. and treated with 10 ml of conc. hydrogen chloride solution until all acetate is cleaved. The mixture is cooled to room temperature and extracted with dichloromethane, the organic phase washed subsequently with dat. Sodium hydrogen carbonate solution and brine. Evaporation yields 9.2 g (95%) of the corresponding nitro-amine as a yellow solid, which is processed further without purification. Hydrogenation of this material following published protocols (Y. A. Liu et al. J. Heterocycl. Chem. 2016, 53, 1430) gives the title diamine (95%) 28.

$^1$H-NMR (acetone-D$_6$; 300.13 MHz) in ppm (internal TMS-referenced): 0.95 (t, 3H); 1.34 (m, 2H); 1.58 (m, 2H); 3.54 (m, 2H); 5.05 (NH$_2$); 7.05 (s, 2H).

$^{13}$C-NMR (acetone-D$_6$; 75.47 MHz) in ppm (internal TMS-referenced): 13.04; 19.77; 30.74; 36.63; 107.97; 123.01; 139.95; 169.20.

The invention claimed is:

1. Process for the preparation of a benzotriazole compound according to the general formula (I):

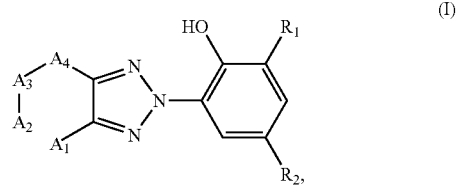

wherein $R_1$ is hydrogen, linear or branched $C_1$-$C_{24}$alkyl, linear or branched $C_2$-$C_{18}$alkenyl, $C_5$-$C_{12}$cycloalkyl, unsubstituted $C_7$-$C_{15}$phenylalkyl, $C_7$-$C_{15}$phenylalkyl with the phenyl moiety substituted once, twice, three times or four times with $C_1$-$C_4$alkyl, unsubstituted phenyl, phenyl substituted once, twice, three times or four times with $C_1$-$C_4$alkyl;

$R_2$ is, independently from $R_1$, linear or branched $C_1$-$C_{24}$alkyl, linear or branched $C_2$-$C_{18}$alkenyl, $C_5$-$C_{12}$cycloalkyl, unsubstituted $C_7$-$C_{15}$phenylalkyl, $C_7$-$C_{15}$phenylalkyl with the phenyl moiety substituted once, twice, three times or four times with $C_1$-$C_4$alkyl, unsubstituted phenyl, phenyl substituted once, twice, or three times with $C_1$-$C_4$alkyl, wherein alkyl is optionally substituted by one or more —OH, —OCO—$R_3$, —OR$_4$, —NCO, —NH$_2$ or combinations thereof, wherein $R_3$ is hydrogen, linear or branched $C_1$-$C_{16}$alkyl, $C_5$-$C_{12}$cycloalkyl, linear or branched $C_3$-$C_6$alkenyl, phenyl, naphthyl or $C_7$-$C_{15}$phenylalkyl and $R_4$ is hydrogen, linear or branched $C_1$-$C_{24}$ alkyl; —OR$_4$, —C(O)OR$_4$, —C(O)NHR$_4$ or —C(O)NR$_4$R$_4$; —SR$_5$, —NHR$_5$, or —N(R$_5$)$_2$, wherein $R_5$ is $C_1$-$C_{20}$alkyl, $C_2$-$C_{20}$hydroxyalkyl; $C_3$-$C_{18}$alkenyl, $C_5$-$C_{12}$cycloalkyl, $C_7$-$C_{15}$phenylalkyl, unsubstituted phenyl, unsubstituted naphthyl, phenyl substituted once or twice with $C_1$-$C_4$alkyl, or naphthyl substituted once or twice with $C_1$-$C_4$alkyl;

—(CH$_2$)$_m$—CO—X$_1$—(Z)$_p$—Y—R$_6$, wherein $X_1$ is —O— or —NR$_7$—, Y is —O— or NR$_8$— or a direct bond, Z is $C_2$-$C_{12}$alkylene, $C_4$-$C_{12}$alkylene interrupted by one to three nitrogen atoms, oxygen atoms or combinations thereof, $C_3$-$C_{12}$alkylene, butenylene, butynylene, cyclohexylene or phenylene, wherein each of which may be additionally substituted by a hydroxyl group; or a group selected from the following list of structures:

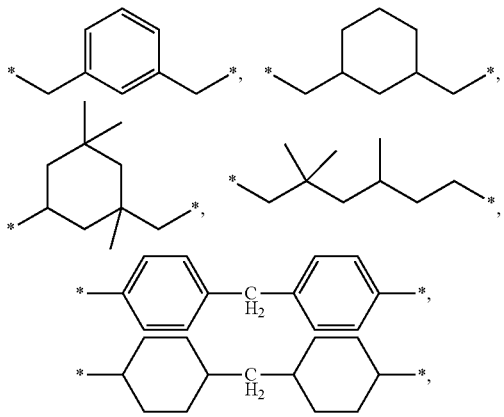

wherein * denotes a bond;
or when Y is a direct bond, Z can additionally also be a direct bond;
m is zero, 1 or 2;
p is 1, or p is also zero when X and Y are —N(R$_7$)— and —N(R$_8$)—, respectively,
$R_6$ is hydrogen, $C_1$-$C_{12}$ alkyl, or —C(O)—C(R$_9$)=C(H)R$_{10}$, or when Y is —N(R$_8$)—, forms together with $R_8$ a group —C(O)—CH=CH—CO—, wherein
$R_9$ is hydrogen or methyl, and $R_{10}$ is hydrogen, methyl or —CO—X$_1$—R$_{11}$, wherein
$R_{11}$ is hydrogen or $C_1$-$C_{12}$ alkyl, $R_7$ and $R_8$ independently of each other are hydrogen, $C_1$-$C_{12}$alkyl, $C_3$-$C_{12}$ alkyl interrupted by 1 to 3 oxygen atoms, cyclohexyl, unsubstituted $C_7$-$C_{15}$phenylalkyl, or $C_7$-$C_{15}$phenylalkyl with the phenyl moiety substituted once, twice, three times or four times with $C_1$-$C_4$alkyl and $R_7$ together with $R_8$ in case where Z is ethylene, also forms ethylene;

$A_1$, $A_2$, $A_3$ and $A_4$ are defined to form a saturated or unsaturated, alicylic or heterocyclic, non-aromatic, aromatic or heteroaromatic ring in formula (I) by being, independently from each other, CH, CH$_2$, CHR$_{12}$, CR$_{12}$, C(R$_{12}$)$_2$, COH, COR$_{12}$, CCO$_2$H, CCO$_2$R$_{12}$, CNH$_2$, CNHR$_{12}$, CN(R$_{12}$)$_2$, N, NR$_{12}$, CO, C(SO$_2$)R$_{12}$ or C-Hal with Hal being F, Cl or Br, with $R_{12}$ being defined independently for $A_1$, $A_2$, $A_3$ and $A_4$ by $R_1$, $R_2$ or $R_1$ with one or more hydrogen atoms in $R_1$ being optionally replaced by halogen;

or $A_1$, $A_2$, $A_3$ and $A_4$ are defined to form a compound according to formula (II) having an additional ring defined by substituents $B_1$, $B_2$, $B_3$ and $B_4$,

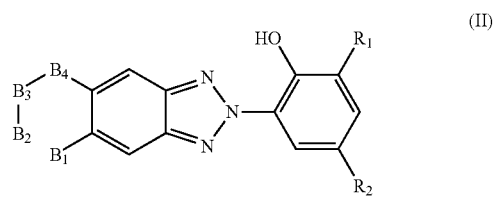

wherein $B_1$, $B_2$, $B_3$ and $B_4$ form an additional five-membered or six-membered, saturated or unsaturated, alicylic or heterocyclic, non-aromatic, aromatic or heteroaromatic ring in formula (II) with $B_1$, $B_2$, $B_3$ and $B_4$ being, independently from each other, absent, CH, CH$_2$, CHR$_{12}$, CR$_{12}$, C(R$_{12}$)$_2$, COH, COR$_{12}$, CCO$_2$H, CCO$_2$R$_{12}$, CNH$_2$, CNHR$_{12}$, CN(R$_{12}$)$_2$, N, NR$_{12}$, or CO, with $R_{12}$ being defined independently for $B_1$, $B_2$, $B_3$ and $B_4$ by $R_1$, $R_2$ or $R_1$ with one or more hydrogen atoms in $R_1$ being optionally replaced by halogen, the process comprising the step of converting the ortho-hydroxydiarylazo compound according to formula (III) to the benzotriazole compound according to formula (I) by oxidative ring closure in the presence of a metal salt,

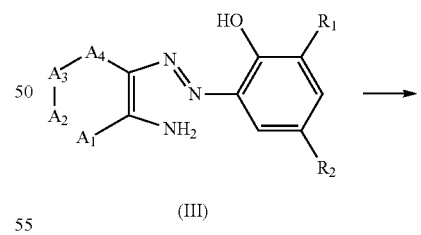

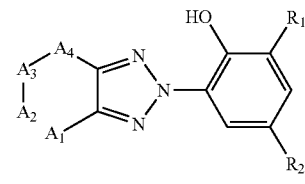

characterized in that the oxidation with metal salt is carried out at a molar ratio of metal salt to diarylazo compound (III) from 0.001 to 4.5;

wherein the process comprises the additional step of preparing the ortho-hydroxydiarylazo compound according to formula (III) by reacting the 1,2-phenylenediamine compound (IV) with an ortho-nitrosophenol compound (V) in the presence of a Lewis acid to obtain the diarylazo compound according to formula (III)

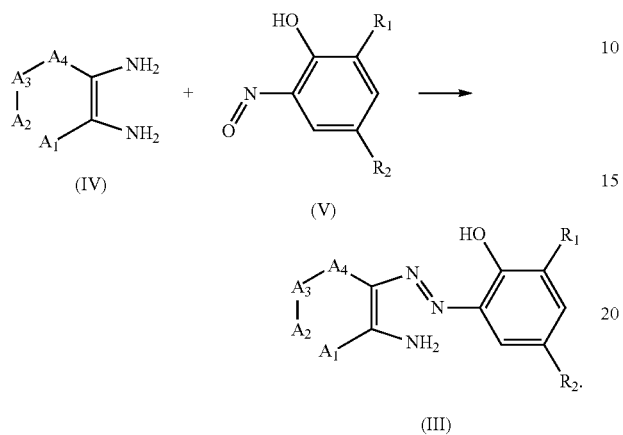

2. The process according to claim 1, wherein reacting the 1,2-phenylenediamine compound (IV) with the ortho-nitrosophenol compound (V) is carried out in the presence of a Lewis acid selected from $B(OR)_3$, $BF_3$, $BF_3$—$OEt_2$, $Al(OR)_3$, $Al_2O_3$, LiOR, LiF, $Si(OR)_4$, and $Ti(OR)_4$, wherein R is linear or branched $C_1$-$C_{18}$alkyl, perfluoro-alkyl, or phenyl, wherein phenyl is optionally substituted once, twice or three times with linear or branched $C_1$-$C_6$ alkyl or fluoride atom; $B(O(O)CR)_3$, $Al(O(O)CR)_3$, LiO(O)CR, or $Ti(O(O)CR)_4$, wherein R is linear or branched $C_1$-$C_{17}$alkyl, perfluoro-alkyl or phenyl, wherein phenyl is optionally substituted once, twice or three times with linear or branched $C_1$-$C_6$ alkyl or fluoride, or mixtures thereof.

3. The process according to claim 2, wherein the Lewis acid is selected from $B(OR)_3$, and LiOR, wherein R is linear or branched $C_1$-$C_{18}$alkyl, perfluoro-alkyl or phenyl, wherein phenyl is optionally substituted once, twice or three times with linear or branched $C_1$-$C_6$ alkyl or fluoride atom; $B(O(O)CR)_3$, $Al(O(O)CR)_3$, and LiO(O)CR, wherein R is linear or branched $C_1$-$C_{17}$alkyl, perfluoro-alkyl or phenyl, wherein phenyl is optionally substituted once, twice or three times with linear or branched $C_1$-$C_6$alkyl or fluoride; and $B(O(O)CR)_3$, wherein R is linear or branched $C_1$-$C_{17}$alkyl or phenyl, wherein phenyl is optionally substituted once, twice or three times with linear or branched $C_1$-$C_6$alkyl or fluoride.

4. The process according to claim 1, wherein the metal salt is selected from a transition metal salt comprising the cation $Cu^{1+/2+}$, $Mn^{(2+)-(7+)}$, $Fe^{2+/3+}$, $Ni^{2+/4+}$, $Ru^{3+}$ or $Co^{2+/3+}$, $Zn^{2+}$.

5. The process according to claim 1, wherein the oxidation with metal salt is carried out under atmospheric conditions.

6. The process according to claim 1, wherein the oxidation is carried out with a sub-stoichiometric amount of metal salt in the presence of an oxygen releasing agent.

7. The process according to claim 1, wherein the oxidation is carried out with a sub-stoichiometric amount of metal salt in the presence of at least one atmosphere of air or oxygen.

8. The process according to claim 1, wherein oxidation is carried out with a metal salt complexed by a ligand, wherein the ligand is selected from the group consisting of $NR_3$, (wherein R is H or linear or branched $C_1$-$C_{17}$alkyl, unsubstituted phenyl, or phenyl substituted once, twice or three times with linear or branched $C_1$-$C_6$alkyl), bidentate amines, and aromatic amines.

9. The process according to claim 1, wherein the counterion in the metal salt is selected from $SO_4^{2-}$; $HSO_4^-$, O(O)CR, wherein R is linear or branched $C_1$-$C_{17}$alkyl, perfluoro-alkyl, unsubstituted phenyl, phenyl substituted once, twice or three times with linear or branched $C_1$-$C_6$alkyl, acetylacetonate (acac), $CN^-$, halides, and mixtures thereof.

10. The process according to claim 1, wherein in the compound according to formula (I),

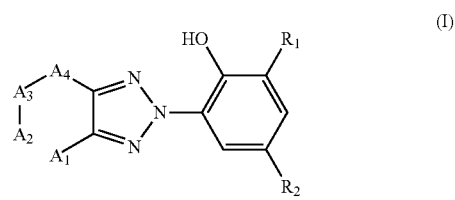

$R_1$ and $R_2$ are defined as in claim 1, and $A_1$, $A_2$, $A_3$ and $A_4$ form another six-membered aromatic ring with $A_1$, $A_2$, $A_3$ and $A_4$ being defined independently from each other by aromatic =C(H)—, aromatic =C($R_{12}$)—, aromatic =C(OH)—, aromatic =C(O$R_{12}$)—, aromatic =C(CO$_2$H)—, aromatic =C((SO$_2$)$R_{12}$)— and aromatic =C(CO$_2R_{12}$)—, wherein $R_{12}$ is defined independently for $A_1$, $A_2$, $A_3$ and $A_4$ by $R_1$, $R_2$ or $R_1$ with one or more hydrogen atoms in $R_1$ being optionally replaced by halogen.

11. The process according to claim 10, wherein the compound is selected from the following list of structures:

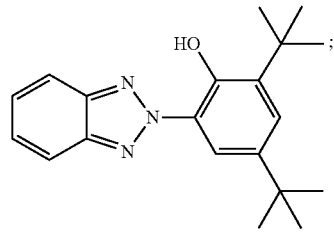

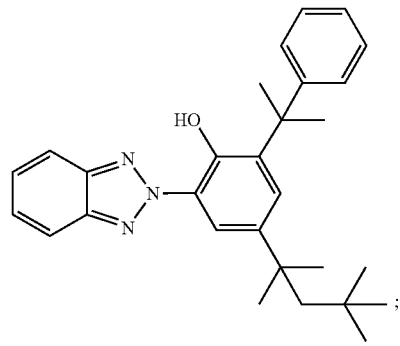

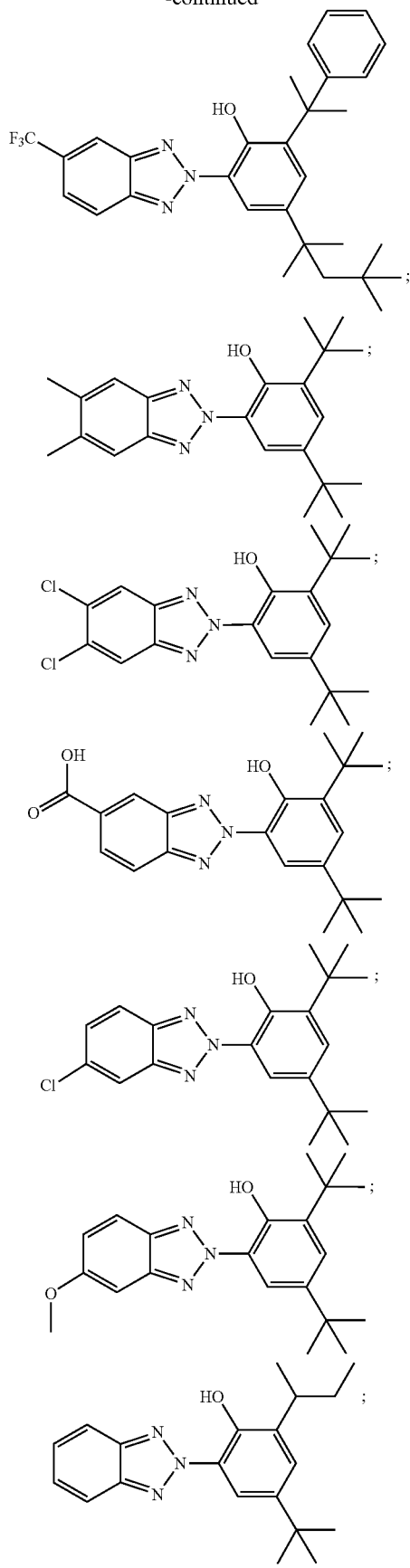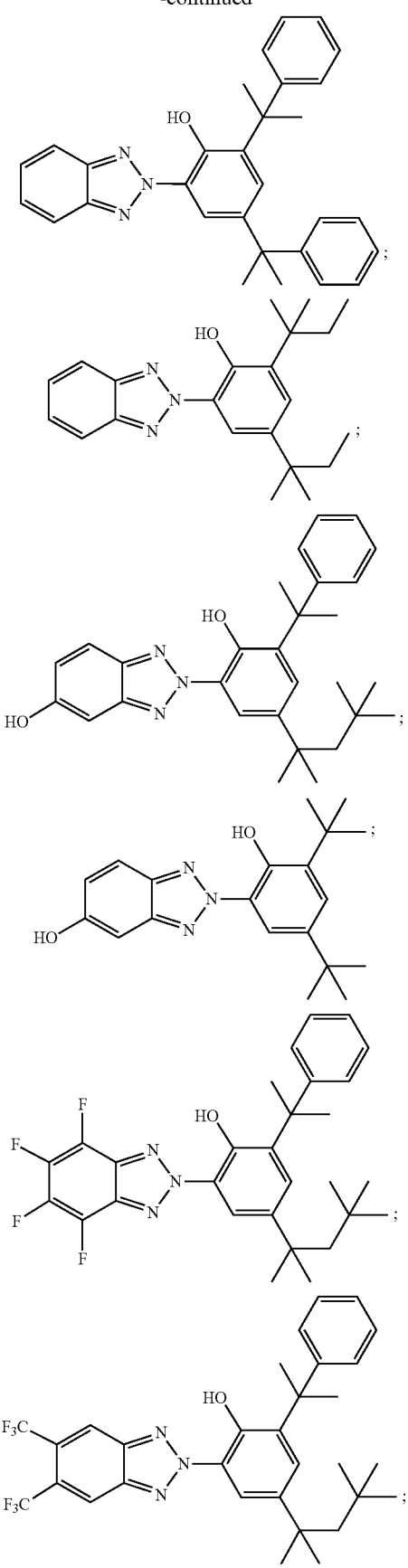

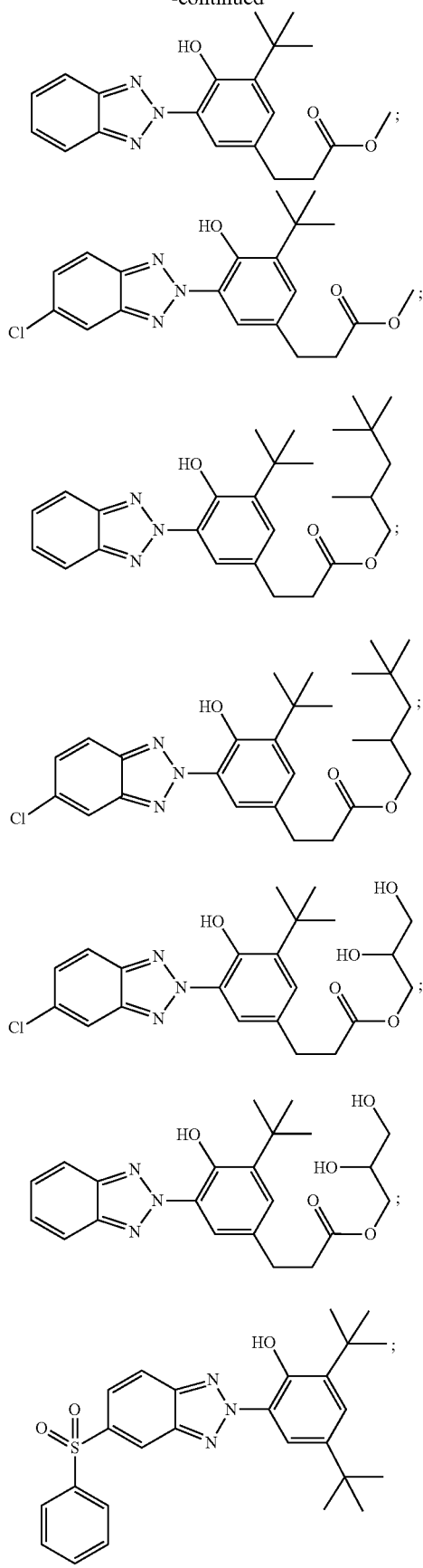

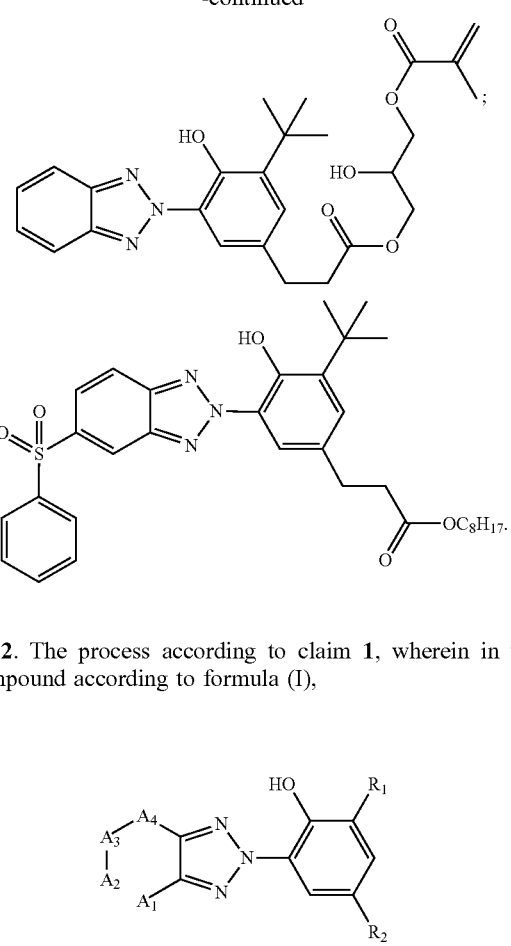

12. The process according to claim 1, wherein in the compound according to formula (I),

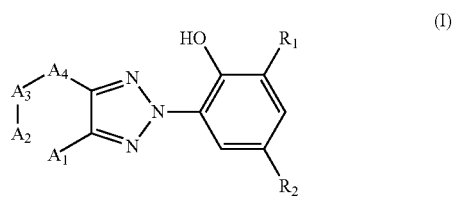

(I)

$R_1$ and $R_2$ are defined as in claim 1, and $A_1, A_2, A_3$ and $A_4$ form another six-membered heteroaromatic or non-aromatic, heterocyclic ring containing one or two additional nitrogen atoms in formula (I) with $A_1, A_2, A_3$ and $A_4$ being defined independently from each other by one or two aromatic nitrogen(s) =N—, or non-aromatic =N—$R_{12}$, together with non-aromatic —C(O)—, aromatic =C(H)—, aromatic =C($R_{12}$)—, aromatic =C(OH)—, aromatic =C(O$R_{12}$)—, aromatic =C(CO$_2$H)—, aromatic =C(($SO_2$)$R_{12}$)— and/or aromatic =C(CO$_2R_{12}$)—, wherein $R_{12}$ is defined independently for $A_1, A_2, A_3$ and $A_4$ by $R_1, R_2$ or $R_1$ with one or more hydrogen atoms in $R_1$ being optionally replaced by halogen.

13. The process according to claim 12, wherein the compound is selected from the following structures:

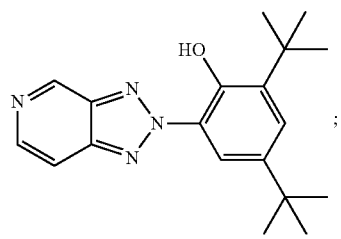

-continued

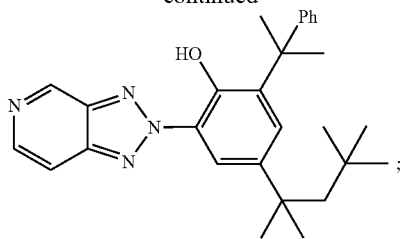

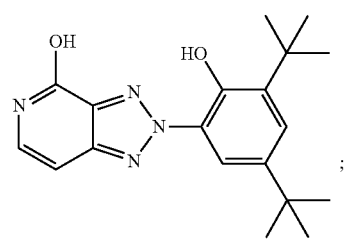

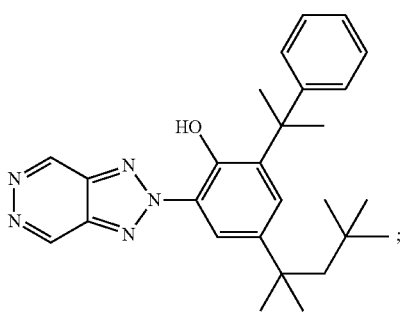

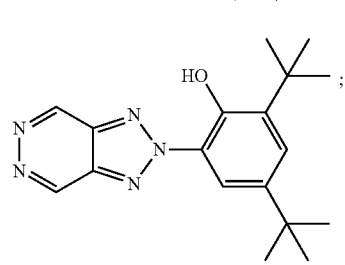

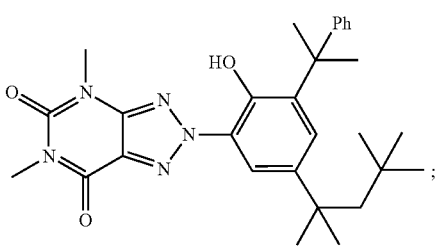

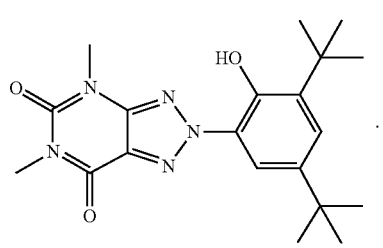

14. The process according to claim 1, wherein the compound according to formula (I) is defined by the following formula (II)

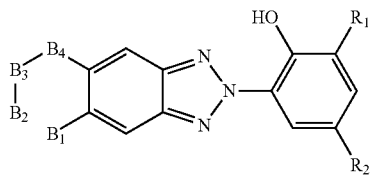

wherein $B_1$, $B_2$, $B_3$ and $B_4$ form an additional five- or six-membered, saturated or unsaturated, alicylic or heterocyclic, non-aromatic, aromatic or heteroaromatic ring in formula (II) by $B_1$, $B_2$, $B_3$ and $B_4$ being, independently from each other, absent, CH, $CH_2$, $CHR_{12}$, $CR_{12}$, $C(R_{12})_2$, COH, $COR_{12}$, $CCO_2H$, $CCO_2R_{12}$, $CNH_2$, $CNHR_{12}$, $CN(R_{12})_2$, N, $NR_{12}$, or CO, with $R_{12}$ being defined independently for $B_1$, $B_2$, $B_3$ and $B_4$ by $R_1$, $R_2$ or $R_1$ with one or more hydrogen atoms in $R_1$ being optionally replaced by halogen.

15. The process according to claim 14, wherein the compound according to formula (II), is defined by the following formula (VI),

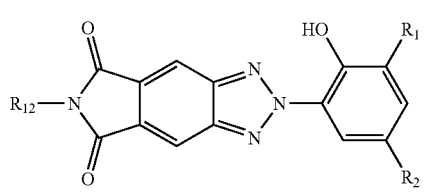

wherein $R_1$ and $R_2$ are defined as in claim 1 and $R_{12}$ is defined by $R_1$, $R_2$ or $R_1$ with one or more hydrogen atoms in $R_1$ being optionally replaced by halogen.

16. The process according to claim 14, wherein the compound according to formula (II) or (VI) is selected from the following structures:

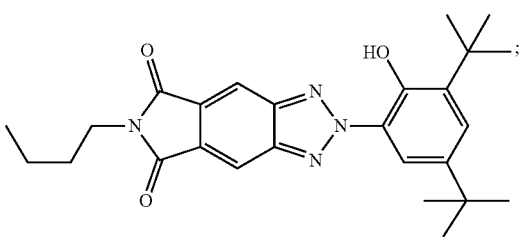

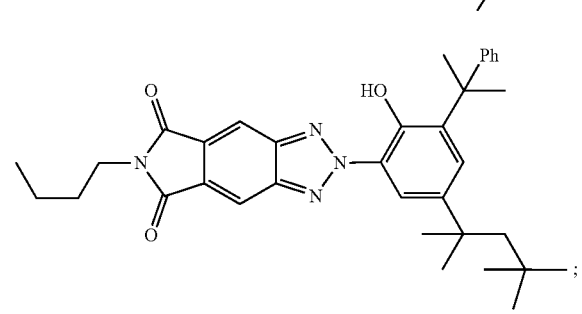

-continued
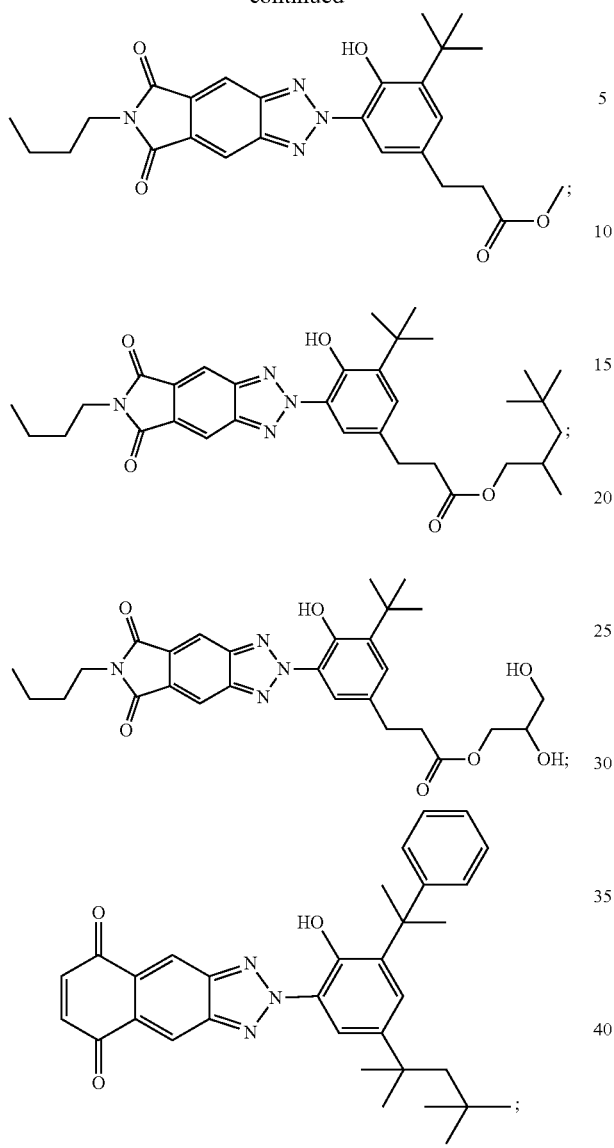
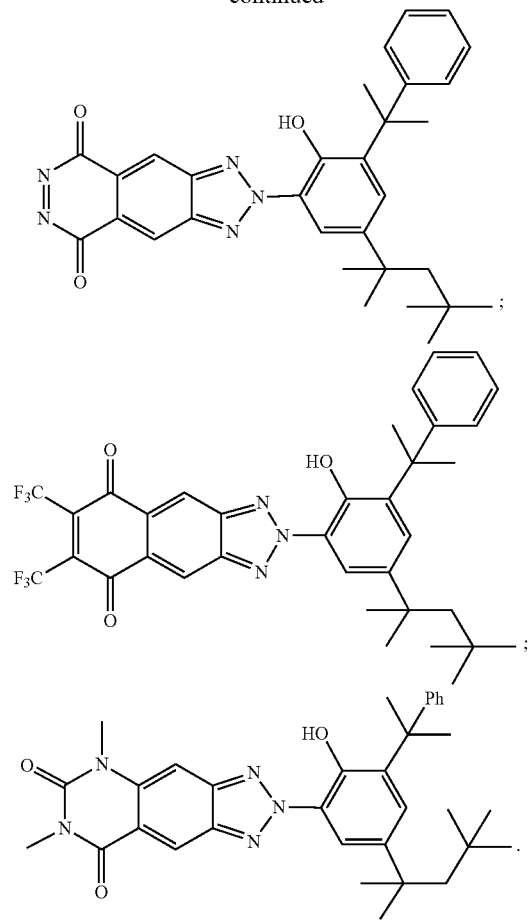
17. The process according to claim 8, wherein the bidentate amine is $R_2N(CH_2)_nNR_2$, wherein R is linear or branched $C_1$-$C_{17}$alkyl, unsubstituted phenyl, phenyl substituted once, twice or three times with $C_1$-$C_6$alkyl, and n is 2 or 3.
18. The process according to claim 8, wherein the aromatic amine is pyridine, pyrimidine, or an N-alkylimidazole.
* * * * *